(12) United States Patent
Rixe et al.

(10) Patent No.: US 10,131,954 B2
(45) Date of Patent: Nov. 20, 2018

(54) METHODS FOR DETECTION AND QUANTIFICATION OF EGFRVIII IN THE PERIPHERAL BLOOD OF GBM PATIENTS

(71) Applicant: University of Cincinnati, Cincinnati, OH (US)

(72) Inventors: Olivier Rixe, Cincinnati, OH (US); El Mustapha Bahassi, West Chester, OH (US)

(73) Assignee: University of Cincinnati, Cincinnati, OH (US)

( * ) Notice: Subject to any disclaimer, the term of this patent is extended or adjusted under 35 U.S.C. 154(b) by 276 days.

(21) Appl. No.: 14/675,400

(22) Filed: Mar. 31, 2015

(65) Prior Publication Data

US 2015/0344955 A1 Dec. 3, 2015

Related U.S. Application Data

(60) Provisional application No. 61/972,461, filed on Mar. 31, 2014.

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 6,225,093 B1 5/2001 Grant et al.
2013/0210645 A1 8/2013 Volgelstein et al.

FOREIGN PATENT DOCUMENTS

WO 2008119562 A1 10/2008

OTHER PUBLICATIONS

Moscatello et al., "Frequent Expression of a Mutant Epidermal Growth Factor Receptor in Multiple Human Tumors," Cancer Research, 1995, vol. 55, pp. 5536-5539.*
Davies et al., "Long-Range PCR," Methods in Molecular Biology, 2002, vol. 187, Chapter 8, pp. 51-55.*
Frederick et al., "Diversity and Frequency of Epidermal Growth Factor Receptor Mutations in Human Glioblastomas," Cancer Research, March, vol. 60, pp. 1383-1387. (Year: 2000).*
Mohammad A. Salkeni et al, Detection of EGFRvIII mutant DNA in the peripheral blood of brain tumor patients; J Neurooncol (2013) 115: 27-35.
Rebecca J. Leary et al, Development of Personalized Tumor Biomarkers Using Massively Parallel Sequencing; Sci Transl Med. Feb. 24, 2010; 2(20): pp. 1-15.
Jill L. Reiter et al, Comparative Genomic Sequence Analysis and Isolation of Human and Mouse Alternative EGFR Transcripts Encoding Truncated Receptor Isoforms; Genomics 71, 1-20 (2001).
Lori Frederick et al, Analysis of genomic rearrangements associated with EGFRvIII expression suggests involvement of Alu repeat elements; Neuro-Oncology Jul. 2000, pp. 159-163.
Lori Frederick et al, Diversity and Frequency of Epidermal Growth Factor Receptor Mutations in Human Glioblastomas, Cancer Research 60, 1383-1387, Mar. 1, 2000.

\* cited by examiner

*Primary Examiner* — Young J Kim
(74) *Attorney, Agent, or Firm* — Dinsmore & Shohl LLP

(57) ABSTRACT

Methods and kits for detection and quantification of EGFRvIII in the peripheral blood for monitoring the therapy of a GBM patients.

10 Claims, 10 Drawing Sheets

Specification includes a Sequence Listing.

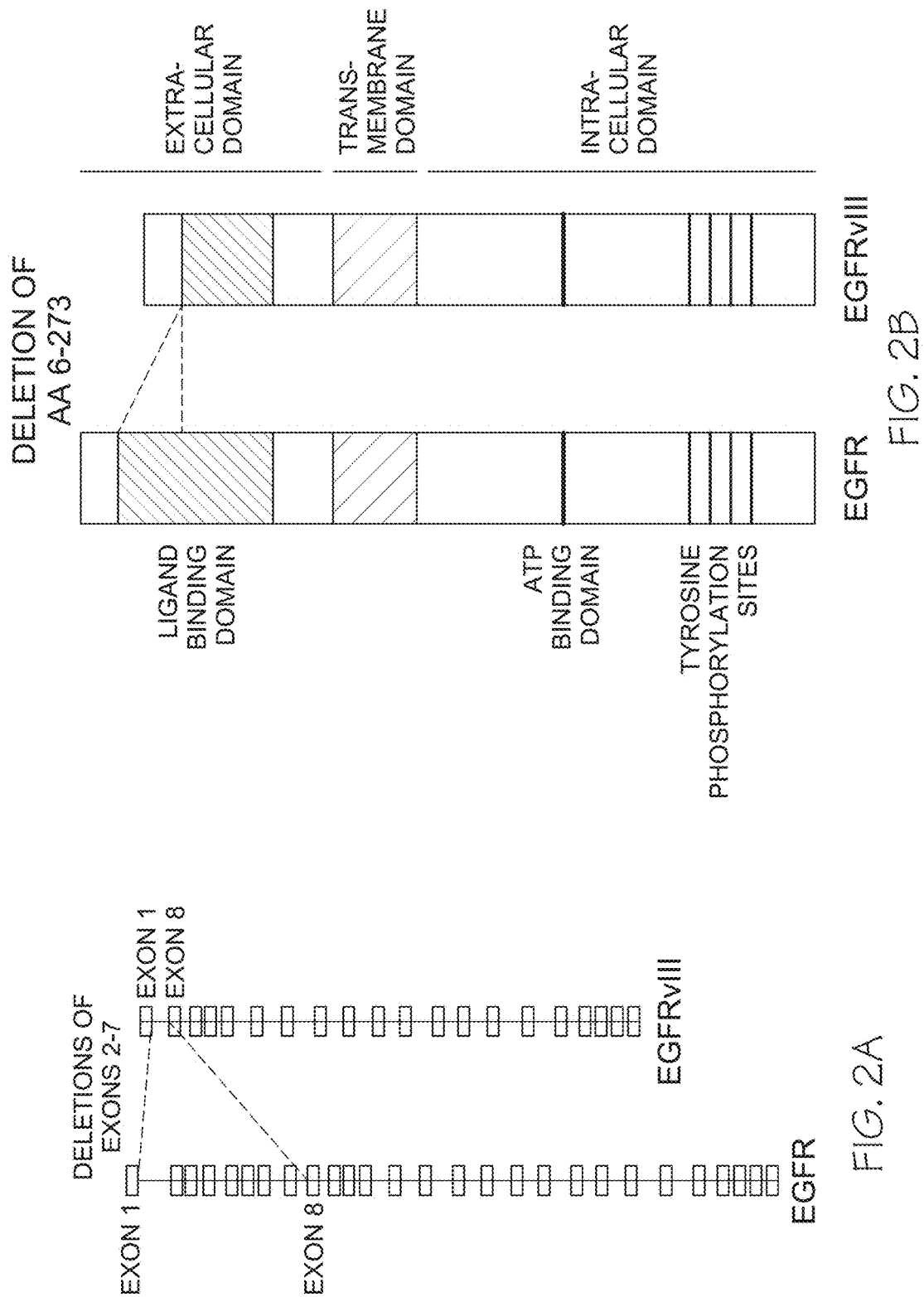

SEQUENCE LISTING

```
<160> NUMBER OF SEQ ID NOS: 35

<210> SEQ ID NO 1
<211> LENGTH: 24
<212> TYPE: DNA
<213> ORGANISM: Homo sapien
<220> FEATURE:
<221> NAME/KEY: misc_feature
<223> OTHER INFORMATION: EGFR exon 1 forward primer (9449-9472)

<400> SEQUENCE: 1
gtcgggctct ggaggaaaag aaag                                              24

<210> SEQ ID NO 2
<211> LENGTH: 24
<212> TYPE: DNA
<213> ORGANISM: Homo sapiens
<220> FEATURE:
<221> NAME/KEY: misc_feature
<223> OTHER INFORMATION: EGFR exon 8 reverse primer (145985-146008)

<400> SEQUENCE: 2
cttcctccat ctcatagctg tcgg                                              24

<210> SEQ ID NO 3
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 1) -
      (12373-12396)

<400> SEQUENCE: 3
gagtcgaatt cccaactgag ggag                                              24

<210> SEQ ID NO 4
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 2) -
      (22461-22484)

<400> SEQUENCE: 4
gtggaggcta aatgggcctt aagg                                              24

<210> SEQ ID NO 5
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 3) -
      (32458-32481)

<400> SEQUENCE: 5
ctgattgaac cttcccagag ctgg                                              24
```

```
<210> SEQ ID NO 6
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 4) -
      (39336-39359)

<400> SEQUENCE: 6
gtatctgccc agaaagctct accg                                          24

<210> SEQ ID NO 7
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 5) -
      (42376-42399)

<400> SEQUENCE: 7
ctgccttgca tgagacacac attc                                          24

<210> SEQ ID NO 8
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 6) -
      (52517-52540)

<400> SEQUENCE: 8
cccccatgta cccctttctt aacc                                          24

<210> SEQ ID NO 9
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 7) -
      (72411-72434)

<400> SEQUENCE: 9
ctacatgccc ctccctttcc tttc                                          24

<210> SEQ ID NO 10
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 8) -
      (82388-82411)

<400> SEQUENCE: 10
gtatttgaga agcccaggag tgcc                                          24

<210> SEQ ID NO 11
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 9) -
```

(92309-92332)

<400> SEQUENCE: 11
gacccctact ggaaagattc ccac                                          24

<210> SEQ ID NO 12
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 10) -
      (102263-102286)

<400> SEQUENCE: 12
ccagcttaga cagcagttct gcag                                          24

<210> SEQ ID NO 13
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 11) -
      (112426-112449)

<400> SEQUENCE: 13
gcctcacatc gttagtgttc cctc                                          24

<210> SEQ ID NO 14
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 12) -
      (122310-122333)

<400> SEQUENCE: 14
catcttgggc tagggtgga tatg                                           24

<210> SEQ ID NO 15
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 1) -
      (18526-18549)

<400> SEQUENCE: 15
ccttaaggac aggcaaaggt gtcc                                          24

<210> SEQ ID NO 16
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 2) -
      (27420-27443)

<400> SEQUENCE: 16 ctgacccta aggagcctgt aatc                                           24

<210> SEQ ID NO 17
<211> LENGTH: 24

```
<212> TYPE: DNA
<213> ORGANISM: Homo sapiens
<220> FEATURE:
<221> NAME/KEY: misc_feature
<223> OTHER INFORMATION: EGFR (Set B forward primers - 3) -
      (38416-38439)

<400> SEQUENCE: 17
ccctgctcag aatgtaggcc ttac                                               24

<210> SEQ ID NO 18
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 4) -
      (58623-58646)

<400> SEQUENCE: 18
gaagattgct tgtgtctgcg tgtc                                               24

<210> SEQ ID NO 19
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 5) -
      (68243-68266)

<400> SEQUENCE: 19
gtgttcctgt cctggggtat ttgg                                               24

<210> SEQ ID NO 20
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 6) -
      (78406-78429)

<400> SEQUENCE: 20
cccatgaaag agtgcacagt ccag                                               24

<210> SEQ ID NO 21
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 7) -
      (88182-88205)

<400> SEQUENCE: 21
cctctcatac agaccccaga gttg                                               24

<210> SEQ ID NO 22
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 8) -
      (98393-98416)

<400> SEQUENCE: 22
```

```
tgttcggaac tgtccatgtt cacg                                          24
```

<210> SEQ ID NO 23
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 9) -
      (108003-10826)

<400> SEQUENCE: 23

```
tgatgctggg aagactggac ttag                                          24
```

<210> SEQ ID NO 24
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 10) -
      (118642-118665)

<400> SEQUENCE: 24

```
tacgacgtgt gttctgtgac tcac                                          24
```

<210> SEQ ID NO 25
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 11) -
      (128343-128366)

<400> SEQUENCE: 25

```
gaagtcctaa ctcatagggc ctgc                                          24
```

<210> SEQ ID NO 26
<211> LENGTH: 177998
<212> TYPE: DNA
<213> ORGANISM: Homo sapiens
<220> FEATURE:
<221> NAME/KEY: misc_feature
<223> OTHER INFORMATION: Homo sapiens PAC clone RP5-1091E12 from
      7p11.2-p21, complete sequence, GenBank: AC009977 version
      AC006977.3

<400> SEQUENCE: 26

```
ttcttttag cacagaataa caatccattg tccacatgta ccatggttta tttatccact     60
catccacatg aagacatctt agttgattct aagttaggga agttatgaat aaagctgtta   120
taaatattca tgagcagatt tatgtggaca acagtgttca actcatttgg gtaagtatca   180
aggagagaaa tcattggatc atatggtaag agtatgtaca cttttatagg aaactgctaa   240
gctgcattcc taagtggctg taccattgtg ccttcccatc agcaatgaat gagacttcct   300
attgttccac atcctcatca gaatttggtg ttgtcactga tctgaatttt ttccattgta   360
acagatgtgt agtggtatct cactgttgtt ttaatttgca atttcctaat gacatatgat   420
gttgaacatc ttttttatatg cttacttgcc atcagtgtat cctctgatga ggtgtttgtg   480
tagggctttg gcccattttt aaatcaggtt atttatcctc ttattattaa cttttaagag   540
tttagttctt tgcatatttt ggataacaat cctttatcac atatttcttt tgcaaatttt   600
tctccagtat atggcttgtc ttcttctcct ggcattgtcc ttctcagagc agaagttttt   660
```

```
aattttaata aactccagct tataaattat ttatttcatg gattgtgcct ttggttttgt      720
acttaaaaag tcattgtcat acctaaggtc atctaggttt tctcctacgt tatctcctag      780
gtgttttata gttttgcatt ttacatttat atgtatgatc agttttgagt taatttttat      840
gaagtgtgta aggtttgtat ctacattcat tttttgcatg tggatgtcca tttgttccag      900
caatatttgt tgaaaagact atacttgctc tattgtattg tgtttctttt ttgtcaaaga      960
tcaattgact aaatttatgt gcgtcagttt ctgatctctc tggtccattg atatatttgt     1020
ctattctttc accaatacca catagtctag actactgtag ttgtatatgt cttgaagtca     1080
ggtagtgttg atcctccaat tttgttctcc aatattgagt tggctattgt gggtcttttg     1140
cttgcccata gaatcaatta gtcaatattt acaaaataac ttgctcgaac tttgactggg     1200
attaatctat aaatcaagtt gggaataagt gacattttga cattatggag tctttctgac     1260
catgaacaca aactattgat ccatttattt agttatttga tatcttttcac cagagttttt     1320 ttgttttttt cttatagatc ttatacatat tttcttatat tcatacctca gtattccatt     1380
tcagggtgtt aatgtaaatg gtaatgtgtt tttaatttca aattccctta gttctttgct     1440
ggtatatagg aaagtgattg cttttgtat gttaacgttg tatcctgctc acttgctata     1500
actgcttatt agttccagga gctttttat tgtttctttt ggattttcta agagacaatt     1560
acattatcag tgaacaaaca cgatttattt cttccctccc aatcagtatt catttattt     1620 atttattgtg tgttattgca ttagctagga cttctaatac aatgttgaaa agcattggtg     1680
aaaggaaaca tccttgcttt gttcctgatt ttagctatag gttttgtag ctgttctta     1740 ttaagttgag gatatccttc tctattctta gtttgctgag aatttttatc atgaataggt     1800
gtaggatttt gcctaatgtt ttcttctgta tctattgata tgatcatgta attttctt     1860 atctattgat atgatctgtt gatgtgatga actacattaa ttgagttttc aaatgttgaa     1920
ccagtcttgc atatctggaa taaatcggag ttggtcatca tgtataactt tgttacactt     1980
tgttgcattt gattttgtaa tatttttctg agaatttta catctatgtt cataaaagat     2040
atcggtctac agttttcttt cctttcttgt aatatctctg tctggttttg ctattaaggt     2100
aattctggct tcacaaaatt aattatggag tcttccctct acttctagtt tctggaagag     2160
attgtagaga atggatgtaa tttctttctt aaatgtttga cgaaaatcag cactgatctc     2220
atctgggctt ggtgctttct gttttggaag gttattaatt atttattcaa tttctatagt     2280
ggatataggc ctatattgat tggcaatttc ttcttgtatg acttttggta cattctattt     2340
caaggaattg gttcatttca tgtaggttgt taaattcgtg ggtatagctg ttcataatat     2400
tcatttatta tccttcaat gttcatgaga tcagtagtga tgttccttct ttcatttctg     2460
atattcataa tttgtgtatt ctctctttgt ttccttagcct ggtgagaggc ttataaattt     2520
tattgatttt ttgaagaatc acttttggt tttgctgatt ttcttgctgg gattataggc     2580
gtgagccacc acactcttgc tcattttttc tattttgtt ttccacactt tttctgcctc     2640
tgtggatttt acacagcatt ttgtataatt cgatttcctc tttttagcat agcaattatt     2700
ttagtcttta actttttaaa atcagttgcc ctagattttt ttctcccaac attttgggag     2760
gccaagggga gaggatcact tcaagccagg agtttgagac cagcctgagc aacatagcaa     2820
ggcactatct atacaaacat aatttaaaa agtccaggca ttagctagga ctgtgcctgt     2880
agtcccagct actcaggagg ctgagatgag aagatcaccg gagcctagaa atttgaggct     2940
gcagtgggct gtgatcatgt cacttcactc ctgcctagaa gacagttaga ccctgcctct     3000
aaaataaaca agcaaataaa taaaaagaaa ggaagaaaag aagagcaagg gcagcaaata     3060
```

```
gaaaatagta ataaatatgg tagctattaa tccaactatg tcaataatta ccttaaatgt   3120
tagtggtcta aatatactgc aatggactga atgtttatgt ctcctcaaaa tgtatatgat   3180
gaaatgtaag ctcccaaaat gatgttatca ggggagagtg ttttttgggag gggattatgt   3240 catgagggtg gaggccttac aaatggggtt agtgctataa aagagaccac agagagctgc   3300
cttggtcctt ctgccatgtg agggcactgt gaaattatgg ccatctatga agaagtgggc   3360
ccttattaga catcaaatct gcaaatacct tgatcttgaa tttcccagcc tccagaacta   3420
tgggaaataa atttctgttg tttacaagta aatcatttta tgttatttg ttacagaagc   3480 ccaaaaagat gaagacatac accagatcac tccattctct tcttgcttgc atggtttctg   3540
aggatacgtt ggatgtaatt ctaatattct ctataggtat tttctttatg ctcctctac   3600 aggtaaggtg ttttttccct ttggcttcat ttaagaattt ttcgttaacc tttgattttc   3660
tgaagtgtga atatgttatg cctaggtatc atttgtttgt ttgggttttc ttggcatata   3720
tcttcctgat gttctctgaa cttcagaat ctgtgatttg ttgtctgaca ttaatttgga   3780
ggaatttttg gtattattgc tttaaatatt gcttctgctc cttttctct ttctttgact   3840 tacagtattc ccattacatg taattatctc acagttcttg aaagttttgt tttgttcttt   3900
ttgttagtcg tttttctttc tgtttttcag ttttggcagt ttctgtttac gtatcttcaa   3960
tctcagaaat tctttcctca agcatgttca gcccactaat gtgtacttca aaagtattct   4020
acatttcttt tacagtgttt ttgatctcta gaatttttaa attctttctt aaaactttca   4080
tctctcagga attcaagact agcctgggca acatagtgaa actctatctc tacaaaacat   4140
tagccaggta tggtgatgca tgcctgtagt cagagctact caggaggcta aggtgggagg   4200
atcacctgag cctgggaagt tgaggttgca gtgagccaag gtcacgccac tgcactctgg   4260
attgggcaac agagccagac cctgtctcaa aaaaagaaa aattccatgg ctctgcttac   4320
attatccatc tgatcttaca tgttgcctat ttttttccatt aaaactccta gcctattaat   4380
catagttttt ttataattaa tactccgatg tgataatgtc ttagtccaat tactgtggtt   4440
ataacagaat gccacaaact gggtgattta taaacaaaag aagctgattt aggctgattt   4500
agaggctggg gagtccaaga gcttggtgct agcatctgat gagtgtcttc ttgcttcatc   4560
ataacatggg agagggcatc acgtgtgaag agagcttact cttataacat agccactccc   4620
acaagaatta acccaccgcc atgagagcca tgtgaattca ttcatgagga cagcgggtta   4680
agtttccaat atatggactt ttcggggaca cattcaaacc acagcagtta gttgtaacgt   4740
tcgtgtcatg tctcattctg gttctgatgc ttgtgcagtc tcttcaaact gcgtctttgc   4800
cttttagtgt gccttgcaat gtggaaatga tatactgggt aagaggagct gtagtaaaga   4860
ggcttctagt gacgtagtga caagctgtgg ggagagggag tgttgcacag tcctgccgca   4920
tgtcacagtc ttccagtgag cctgtgtccc tggactgtga acttcatgct gcttctcag   4980 cttccccagc cccttagatg gtacagaact gttggagggg ggtggagttg tatatttccc   5040
ttgctctggg taggtcaccc tctgataaaa caccaggtta ggcctctggt gaaataattt   5100
ctcctgaggg cagaccttct attaataata gaatgttcca acctatttca aaatggttcc   5160
tcttctcctt ccactgccag aagcataatg agattttccc cctaatattc gtggtaagga   5220
cctagcagag ctccaggagg taacactctc aagtgtctca tactaccctg caccatgact   5280
gggctctgct ggagttctta atttgcagaa ctgcccacac tgagcctccc gcaatttctc   5340
aattacaggg caaactttcc cagccggcac tgggtccttg gaggtttctg tctgctggtt   5400
```

```
tcttcctctg gaggttgtgc ttctgtgttt gcctgtctct ccaatttggg gggcagtggt    5460
ttgcccaatg acctcaattc tctgaaagag ctaagaagag gtgttaattt ttcggtttgc    5520
tcagctttct acttgttgct agaatggagc gccaatagtg cctcctatag tgacatgtaa    5580
ccctcaactc tagagatgat gaagcatact aatgacaaag gagaaatgct tcagcagttt    5640
tctgtcagca cattacccct tgaaaaagct gcttcttcca cattctgcaa gagatgggtc    5700
tcaactcaga gctcaaggca aatgacttcc ttcaaggaga aggaataaac agtctcagaa    5760
accatgaaag cctgccccca ggagtgtccc tgaacctcag caggggccac acttaccttg    5820
cagaaatagg tgaggcatgc tcctggtaca aaatcccaat ggtacagaag gacaaattga    5880
aaaacaagtc tccctctaaa cccctgaccc cgagctacct agttctcctc cctagaggca    5940
aagctgttac cagattcttg tatctcctta acatatatcc ttagaagagc tgtcaagtga    6000
acacatgttt aagtgaaaac ctattttaga agtgcatttt cttaaggaac tttaggggttg   6060 gaaggaacct gtgtcagtcc ttaattcaca acctccatta gtacttattg ttcttgcaca    6120
aaaatctttc tcaaaaaagc cctttccact ctgacatagc ttattctact tttacttagc    6180
tccaataact tataaaacat attttgaaa gtctaaaatc tgccactatg ttttttttc      6240 ctaatcaatc tttactttga cctctaagcc agagaaaaca ggtggtcaaa tgccttttgc    6300
ctaagatgga acttagaata tttgaagacc tcagatcttc accctgccaa ataacgtgtt    6360
tctcctcccc tttcacagag catttggttt taggaaaattc agagccacat tccttataga   6420
caagactaaa ctcttattca acatactcag aaacttcttc taagaggata accactcatc    6480
agaggaaaaa agtttctcat gtacagctgg caaagggatg gaaccatctg tgttattaaa    6540
attgacagac gcttatgaga tttattaagg gaaatactag agtcttagta catacttgct    6600
aatatagcat acatgaaggc tttatctata attttttttgg ccaagcagaa attttggtat   6660 tactcacccct aacaaatttc caagacatta tgaaatagaa ttttaggtcc tgacatcacc   6720
atttgtctca ggttttgaag cgttgctgga caagagggggt aaaacacggc tctgccttgg   6780
attcaaagtt ggcctctcat actagcaagt ataccttggt atcctggtca cttctcccgg    6840
ccacagcatc acattgctat aaaaggcaga tacaagtatt aaccagctca caggttatca    6900
gataagctta gtctgaccaa tgcttaacac agcaactggg ccactattgt cattcctgtg    6960
gtggtggcac acacacccag cctctgtccg ggccatggtc taggaccacc ctccacagag    7020
gctgtgagct agagccctaa ctgtgcaggg ccctaactat gccaggctac ttatctctct    7080
taagaggact tcattagtgc ctgctcggcc atacagtttt ttacttacca agtaacacag    7140
ttatcagcac actccaggta ctagccaagg actacaaaat caacgtgaat gtcagctttt    7200
gtatcaaaag ctcaaaggag aaactcaaac tttacataga tgtcccatga agatgttcag    7260
caaacccatt cttctctgtt ccctggaatc catcccagta ttgtgctatg tgtgtgtcta    7320
gtaattcttt acaaaaagct ctgtttcttg tgatgctatc agatcacatt gaagaatata    7380
caagccgtac tatgaaggct gttgtctcat atagtcctaa cgtagtgaga actgatgttc    7440
ttacatgctg tcttttttggg cactcaaaga aattcctgta cagtcttaca aatcagttgt    7500
agcttaaatt gatttgtgtt gtgacttgta cacacaggtc acattccctt gacagaaaat    7560
atagtttaaa accaaatttg cagcccttgt taagtgaatg cacaggactt tattgtattc    7620
aggtctttta ttgtaagact cactcctgtc ttcattttat gttccactgt tgtgcttccc    7680
atttgccttt ctctagtttt gttttctgtg tttctacgga ctgctctcag cccaggtgtg    7740
caggaagcac acacatgcct gcagagcctt catggcctct gcattcaggg catgacttca    7800
```

```
acgcacagtg gctgtactga tttgttaaaa caaaggaaca gattacttct cctaattcac    7860
agggaagttc caggttgtgc gggcagtgag cagacctgtg tctgtctgcg cttgccctgg    7920
tgaaaaaccc caccgttcag gctgcagggt gcgagaccca ggcacaaaca ttttgctgga    7980
tgaggaggaa agatgtaagg ttgctcccct tcagagacac caaagggcag gtctgtagct    8040
tcacttactt caggattgtg atttttgaca gagccgagag atcagggttg ttgaaccagg    8100
cctgaaggtc ctagtgaatc tcgtgaagag aggaggggtc tggctgtaac atggacctag    8160
aggacatttt tactgcagga gaaggaacag tggggatggg gtggacttgc caaaggaata    8220
tagctcaagt tcctgcagcc caaaaaagct cagtttcttt tggccaaagc ttccgcgagt    8280
ttccctggca tttctcctgc gggagctaca ggggcagtgg gacacttagc ctctctaaaa    8340
gcacctccac ggctgtttgt gtcaagcctt tattccaaga gcttcacttt tgcgaagtaa    8400
tgtgcttcac acattggctt caaagtaccc atggctggtt gcaataaaca ttaaggaggc    8460
ctgtctctgc acccggagtt gggtgccctc atttcagatg atttcgaggg tgcttgacaa    8520
gatctgaagg accctcggac tttagagcac cacctcggac gcctggcacc cctgccgcgc    8580
gggcacggcg acctcctcag ctgccaggcc agcctctgat ccccgagagg gtcccgtagt    8640
gctgcagggg aggtggggac ccgaataaag gagcagtttc cccgtcggtg ccattatccg    8700
acgctggctc taaggctcgg ccagtctgtc taaagctggt acaagtttgc tttgtaaaac    8760
aaaagaaggg aaggggggaa ggggaccctg gcacagattt ggctcgacct ggacataggc    8820
tgggcctgca agtccgcggg gacegggtcc agaggggcag tgctgggaac gcccctctcg    8880
gaaattaact cctcagggca cccgctcccc tcccatgcgc cgccccactc ccgccggaga    8940
ctaggtcccg cggggccac cgctgtccac cgcctccggc ggccgctggc cttgggtccc    9000
cgctgctggt tctcctccct cctcctcgca ttctcctcct cctctgctcc tcccgatccc    9060
tcctccgccg cctggtccct cctcctcccg ccctgcctcc ccgcgcctcg gcccgcgcga    9120
gctagacgtc cgggcagccc ccggcgcagc gcggccgcag cagcctccgc ccccgcacg    9180 gtgtgagcgc ccgacgcggc cgaggcggcc ggagtcccga gctagccccg gcggccgccg    9240
ccgcccagac cggacgacag gccacctcgt cggcgtccgc ccgagtcccc gcctcgccgc    9300
caacgccaca accaccgcgc acggcccccct gactccgtcc agtattgatc gggagagccg    9360
gagcgagctc ttcggggagc agcgatgcga ccctccggga cggccgggc agcgctcctg    9420 gcgctgctgg ctgcgctctg cccggcgagt cgggctctgg aggaaaagaa aggtaagggc    9480
gtgtctcgcc ggctcccgcg ccgccccgg atcgcgcccc ggaccccgca gcccgcccaa    9540
ccgcgcaccg gcgcaccggc tcggcgcccg cgccccgcc cgtcctttcc tgtttccttg    9600
agatcagctg cgccgccgac cgggaccgcg ggaggaacgg gacgtttcgt tcttcggccg    9660
ggagagtctg gggcgggcgg aggaggagac gcgtgggaca ccgggctgca ggccaggcgg    9720
ggaacggccg ccgggacctc cggcgccccg aaccgctccc aactttcttc cctcactttc    9780
cccgcccagc tgcgcaggat cggcgtcagt gggcgaaagc cgggtgctgg tgggcgcctg    9840
gggccggggt cccgcacgtg cgccccgcgc tgtcttccca gggcgcgacg gggtcctggc    9900
gcgcacccga ggggcgggcg ctgcccaccc gccgagactg cactgtttag ggaagctgag    9960
gaaggaaccc aaaaatacag cctcccctcg gaccccgcgg gacaggcggc tttctgagag    10020
gacctccccg cctccgccct ccgcgcaggt ctcaaactga agccggcgcc cgccagcctg    10080
gccccggccc ctctccaggt ccccgcgatc ctcgttcccc agtgtggagt cgcagcctcg    10140
```

```
acctgggagc tgggagaact cgtctaccac cacctgcggc tcccggggag gggtggtgct   10200
ggcggcggtt agtttcctcg ttggcaaaag gcaggtgggg tccgacccgc cccttgggcg   10260
cagaccccgg ccgctcgcct cgcccggtgc gccctcgtct tgcctatcca agagtgcccc   10320
ccacctcccg gggaccccag ctccctcctg ggcgcccgcg ccgaaagccc caggctctcc   10380
ttcgatggcc gcctcgcgga gacgtccggg tctgctccac ctgcagccct tcggtcgcgc   10440
ctgggcttcg cggtggagcg ggacgcggct gtccggccac tgcagggggg gatcgcggga   10500
ctcttgagcg gaagccccgg aagcagagct catcctggcc aacaccatgg tgtttcaaaa   10560
tggggctcac agcaaacttc tcctcaaaac ccggagactt tctttcttgg atgtctcttt   10620
ttgctgtttg aagaatttga gccaaccaaa atattaaacc tgtcttacac acacacacac   10680
acacacacac acacacacac cggattgctg tccctggttc aagtgtgcca agtgtgcaga   10740
cagaacatga gcgagtctgg cttcgtgact accgaccata aacccacttg acaggggaaa   10800
catgccttgg aaggtttaat tgcacaattc aaccttgag ctgcgcgggt tccaagagcc   10860
aggcccgtac ttgctgttga tgtcattggc ttggggagtt ggggtttggt gcccagcgcg   10920
gtcgttgggg gaggggcaag gcatagaaca gtggttccca gaccttgctg cacattggaa   10980
ttacctggga ttaaaaaaaa aaaaatcaaa acaaaaacca gtgtctggct cccgccccca   11040
gacattctga tttaattggc atggggcaag acctggactt gggatttttt ttaatgctct   11100
tcatgtgatc tgttgggcag ccagatttgg ggatcactag acggaagaag gattgttaaa   11160
gtctccggag atgttacttg ccaatgctaa gagctctttg aggacatctg gaattgttac   11220
aatattgcca aatataggaa agagggaaaa ggtagagtgt gattccaata ataaaggatt   11280
ccgcttttca ttgaaggaac tggtggaaag gtttcttctc tgctgagcct gcaggcccgt   11340
cctgcctgcc tggggtgccc gggagacgcg ggcctgctcc ggagactgct gactgccggt   11400
cctgttagtc aggtgtcagc cctgtctctg ccgaagagac tcttctcttt attttaaatt   11460
aaaccctcag agcaccacca aagcatcact tttctccctc cattggtgtt ctcattcttt   11520
gatgttactt gtttgaacac cactattagt agttggagat ttgttcctga gaaaaatata   11580
aataccactt aatttgcctg tttgtcccgc attcactcaa aacagaatgc tcctgaagac   11640
aagagagaga gtaggagaac agacgctatt ccattacagt aacataaaag actggatttt   11700
caggggcaaa ttattaaaat aggagatgag ctcttttaac agaaatttgt ttaaggcctg   11760
tgtctatcaa attcagtgga ttttattcaa gatgcacttt gtttagtggg agttttgttt   11820
ggttctggga catgctaact tctagacttg ctgctcttag aggtaatgac tgccagacac   11880
catttcatga gtcctaatcc ccacattaag cataagaggt gcacactctc ctcctatggg   11940
ggaaactgag gtacgaagaa ctaaagtgac tttcccacag ctggtgggag gcagacggga   12000
aattcacacc aggggcttcc aactccagat ccctctctca acttccaaac tccactgcct   12060
tgtccgagtt ctggtttcag gagatccaaa tcaggtgtgt gcaaatgtct aatgtcagag   12120
ctggcaaggg gaaagggccc agggagccgg ctcatgacga tgagcctgtc tgaagcttca   12180
acgcgggctg tccggcagtc tgcattcctg ccgagttcct cagccctctg ttgggtcacc   12240
ttccatagag gcagcttagt cctcagttca gtgagcatgg agtggagact gcttgagggg   12300
tgctgagcaa agccctgcct cttacaggat gaaggtgctc tccagaaggg acactggaaa   12360
gtattccaag gcgagtcgaa ttcccaactg agggagcttt gtggaaataa gcccgcccag   12420
ccccacttct ggagacgttc ccattcagta ggtccgagct gtcttaaaga gaaaccaaag   12480
tggggatatt aatggtatcc aaagtgagat ctaccccacc ctccctcctc aaaggaggtc   12540
```

-continued

```
agatcaagaa agcccaagcc cggcctggca attgggacct ttcttctcac tccagcccag    12600
ggtgaaggtg gacaagtcac tttgacccct caggcttctg agctgttgtt tctgaattca    12660
gtgaatattt actgagtgca tagaatatgc tagatattct gggctaaagg ttgaagggggg   12720 ggtgagtttt aagggtttct gctcttgctt ccagattgct ttcaaatctg gaaaggacac    12780
cagtggtttg tgtgttagac ccacactgcc gtagcacaga atacaagaaa ctggctgaga    12840
gctccaatag gcttttaaca gtaatttctg gcttcacgta tttagtttca taactcatga    12900 ttttcaaaa acttctggtt tgaagacacc gattgccgaa agtccattgt gctgcataat     12960
tacacttggt ccacgtgaca gcactaacat gttctgaaat gttttagaa gtagtctcag     13020 caaagatgaa ggattcctcc ctgtttgaaa agaaaatatt ctttgttttt tctttgatct    13080
aagctctaag actagcagct agcatctgaa acttttttga cgagagtgac aaaccaactc    13140
taatattaaa ggcaattgat gattatgggc actgaaggga aggtaacccc aggctggtgc    13200
cccggaatag ggatgggtca caatgttgag gacatttcgc ctgttgcaga acccacctgc    13260
aacacagtgt ggcccttgcc atgtgacttg tgtgtgtgcc tgtgtgtctg tgtgtgcgtg    13320
ttttaatttt gacttcataa gtactctagt tatgagctta tttaacattg ggttttacta    13380 atagggggtat gtgttgagaa aatttcaaag ttttagaata tggttcaccc acatgttgct   13440
tccctgtaaa tataattttt aaaccagat tctgggccgg gcatggtggc tcacctctat     13500
aatcccaaaa cgttgggagg ccgaggcagg cgaatcatga gccaggagt ttgagaccag     13560 gctgaccaac acggtgaaac ccagtctcta ctaaaaatac aaaaaaaatt agctgggcgt    13620
ggtggcaggt gcctgtaatc ccagctactc aggaggctga ggcaggagaa ttgcttgaac    13680
ccaggaggca gaggttgcag tgagccaaga tcgcaccatt gcactccagc ccgcgcgaca    13740
gtgtgagact ccatctcaaa aaaaaaaaa aaaaaacaga ttctgttcct cagatccatt     13800
ccatttttgt tttccttat cacttatgga catttgaaat tatggtaata acattgtta      13860 gtctcagtta attattactg gtttattctt gaaccactaa tccatagaga atagagtgta    13920
aatcttaact tgttcctgta ggccatcccc attaaacatc atagtgtttt ctcattcgtt    13980 cttttcgtt ttcctcctac aggaatgaat tttctaagaa aattccagca gttggctctt     14040
tggacgacat ctctagattg tcctccattg ggcccatagg cacaagctgg ccagtttgaa    14100
tttgggcaag aatccaggca ttggaactta ttcaaataac tagtttgcct gtaattttca    14160
ctttttcaga gtcatctgat aaagcttct tgctacacat ttagatagat acactcaatc     14220
cagttgtcta gaaagttccc tgagccagct gggagcagga ggggtagttg gggccaggaa    14280
tattgggggt gtgtttactg agcccctaga aagtaagtgc tagatttgac atttcaatcc    14340
ctgaaggccc tgaagttcag tatcaaatga ctggtcctgt ggactgagca tctgtgaatt    14400
gcatatgctt agagtaaatt ttactcctac cagtttcagc agcttgcttt agcaagcagt    14460
atggaaacac taacatgggg gagtagaatt tctctctctg atccaagttt tatctcattc    14520
tggtgggttt tcaaggagag actcggagtc caagtgtcct ttctgaatat atctggaact    14580
tctcattaac aaaagactca agttataatt taggggacaa ggcacccaat gagaatgcct    14640
tgcaggcagc cctaagtaca cctgcaatta caccattact agcgcggcag cacacatggc    14700
cctgacttag tttaaataat tacgtaagtc aaccatgatt gttttgcccctt tgcatagaag  14760 ggcaagtatt ggtacctgtt acaacttagg cttttttttc tttatgtttg agccatgatg    14820
agtgatttac actgttgcat ccatatgttg agatgtaaga ataaattaga cttggtaatt    14880
```

```
gcccttaagt gtctggaagt caactgggga aagagagcta gagataataa gtgtgaaaca   14940
atgtcacaga atcaatgacg gaactcttcc caggacaaag gatgactttt gagttcagtc   15000
tttgccttta attctacatg gggaggagag cacgtttagc cacaaatgga agggattact   15060
catttgagct atttggttat atgattattt ccccagagaa taggatgtgc agggcattac   15120
acaagcagtg ccaatagcag caaagttctt gagagtgcta gtaattcaaa tggcaggaag   15180
agaaggaata aatggtaagg ctacctacag ttcacagaga gctccatcct cactgtggct   15240
ttggattttg tcctgtgtga aagagaagtg actgtgaact gacatgctgt gtttggtgtt   15300
ttagaaagat ggctgcagca gcggtttggg gaatggactg caggagtggc attggaaaca   15360
ggaaggttca tgactattgc cagagacaga ggatgaagca ggagcaagga agattcagga   15420
caggggactc cggggctgat caggaggcag aactggttga taagtatatg tagcagcata   15480
agaaagaaag aatcccagat tgacacccag gcttctcact tggaagcctg gatagatact   15540
gaatgcaatc acaaaggctg ggaagtcaat gggactgcag ggaagggaag ggaagggagg   15600
agaagaggaa gggcaggagg gtccaatatc aatattcagc ttttagatgt gttgagcttg   15660
aagtgctcag atggagaagt ccaggaggca gtagaatacg gtggtccaga gcacaggaga   15720
gcaatgtggc ttgagttgtc atttgctcac atatttccgt gtcagttact tgtcttagat   15780
cacagaacaa gttctcctct cacagtttcc tggctccacc tgtctcatgc tcaccgtcag   15840
catcgaaatt gagccacacc agggttctg gataccagct tctctctagg tgaggctgct    15900
atagtcagca gctgattagt tgcagttatc agcaactggt aatataatat attgtgcata   15960
taagtgtacc agaagtcatg tttatatatt gctgcaaata ctcggaatgg ggatctcttg   16020
ttccctgctt aagaccacat cacattactt ggttttgtac gctagtggct gaaccaaaaa   16080
aagtaggaga tgattttttt tcttttttct aaagcagta gcttttgaac cttgaccatg    16140 cttttctaacc agctgagggg cttttgaaaa agagggtgcc ttactgtgcc ccagaccagg   16200
acaatcagta tttctgggga atggagcctg cacacacac atttcttaaa gctcccttgg    16260
caattctgag gagtggatta catgttgtat gtagctcgta acgaaagaaa tcttgtcttt   16320
gctctcagac ccccatttct tactcatctc atgagctcct tcgagatcca gaaacagttg   16380
catatttcat tagtaaatca gttccagagt cacattttat ttcacaagtt agtccattaa   16440
aagtttcctg cagtgaggaa atagccagaa agaacactcc accctcctc cttttttataa    16500 ctatagggtc tggctcgaca gagcaggagc atcgccatct tggacaagcc cctcattcta   16560
aagttcacct taataaaaaa ctgcctaaat tcaaactgca tcagcctaat ggctaaggtc   16620
agcatgacca taaaccacaa ataacatctc caaccggaaa cattcgaaac tcctcctcga   16680
ccagagacat gctagtcccg agataacccc cctccagcag ggaagatgcc agtctcggga   16740
taacctctct ctggccggaa agatgcctgc cccaagataa acttgcctcc tcccagagat   16800
attccaaccc tgccataaaa cttctccctc aaacaggaac attccaaaat tctgataatc   16860
tccctcaccc taaaaccaat atatactcct agtctgtaag agaaagcgct cttgaccaaa   16920
attcaccagg agtgcctccc aggttttaac taaagaaaac ctctctttaa ctgccaaaaa   16980
aaaaagggaa aaaaaaaag cttctctgcag tggctttcag cgggcccagc atggcagcag   17040
cacctgagaa cctgttggag atgcacactc ttggacccca ccctggcctc tgagtaagac   17100
actggaaggg caggcccgg tctgtgcaca caagtcctca gggagattct gactgatgca    17160
tgccagattt tgagaactgc tgatatactc caggcacatc gcatgctggg atctagatac   17220
accaagggaa caaataaact gcacttgtcc tctgaggacc gacttacctt ttggaagggc   17280
```

```
tgagaaagag agacacatac aagatcactc cctgtaatgc aatgttttat aacagatgtg   17340
atttgggatt tcagtgggag cccaaaagag ggactgacta attcagcctc tgtgacaagg   17400
ggagtttctc agaaacagaa tgcttagctg ggcctccagg cacagggaca ggaatgagga   17460
aatacttgta ggccctgtgc tccttcagca aaaccctcag tttcttgtta tttttataaa   17520
tgcaaacatc ttattaaagt agatgctaag gcattagaat ttcctgcttt attttttctaa  17580 atgaccatga ggaaacctgg aatgtcaaag ataaagtgca acacattctg catttaaaaa   17640
ttaaaatgat cctttttaaa agtagcaacc agatgtgaaa aattggactg gagtccaggt   17700
tatagttgat agctttaact ttctccccaa cagcaacagc acaattttcc ctaaaatgtg   17760
ttatgaataa gtaaaatgac tacttcacat cctttaactc ttcctacaga aatctaagag   17820
agaaatgaaa caaagtttg cacagttcta gacacgataa atacatgtga atcacacaa    17880 ctcagaaaat gtcccttaaa ttaattgagc cattggtact tgtgaattag aagagacatc   17940
tatgttctga tccactgttg aaagctgtac aatgttacct atttatttgc agacatcctt   18000
tggaaacaaa taggtagatt tgcaacaaat aaagagtgga gtacagctgc tgacattacc   18060
ttgtatattc atgcctttat gtaaaaaaaa aaaaaaaat atatatatat atatatatat   18120
atatatatat atacacacac acacacatat ggaggtaaag accactgctt gctttgcagt   18180
tgttttaaga gcattcatga aggattttat tttataagca gaaatgtgat atctgacgat   18240
tttaccacta catgcttgca ggccagtgca cagcagatga cgtcatgatt gttttagcag   18300
tcctatcgtt ttacttatga tgtcattaca acccctttgct aaaatttctt tcctttactc  18360
caggttttgg ataaaattga tgcattgcac atagtctctc tgataagaca aactggcatt   18420
tgtatgtgaa aaactgtgca tgttttagtg tctctgctga tactcaaatt atccattatt   18480
ttagtgctgg aataaaaaca aaccacttag tgaatttgtg caggtcctta aggacaggca   18540
aaggtgtcct gagattttct gatcattgta taccaaattt tagaaacttt ttcaaaaaca   18600
tttttttaat ttcaaaaacc tggttttgtt tatttaccag caatcattga atacctgaaa   18660
gctttcagga gattttatta caatggtttc tattcactta caaaattatc tcctagttca   18720
ttctcataca ctgtaagcca ttgtaaatgc ttcaaattgt gccgaacaag ataaactaga   18780
caaactattt taagtttgtt ctagtgctaa cttgcaagat ctaatggctc caactagatt   18840
tttaaaataa agtatatttt aatatattat tagaaagtta agcaattatc tgtttatagg   18900
taacaaaaac cctggaaccc caatgtcaga tgtcatccac ttttgattaa gtccaaacat   18960
atgacagata aacaaaagat ggttggctgg gctcagtggc tcatgcctgt aatctcagca   19020
ctttcagagg ccgaggcggg cggatcacaa ggtcaggagt ttgagacttg cctgaccaac   19080
atggtgaaac ccgcctctac taaaaataca aaaaaacag ctgggtgcgg tggcacgtgc    19140
ctgtagtccc agctactcag gaggctgagg caggagaatc acttaaacct ggaaggcagg   19200
ggttgcagtg agctgagatc acaccactac actccagcct aggcgacaga gcaagactca   19260
gtcaaaaaac aaaaaaaaag tggtcattgg agaattattg tgtcacctgt tgttttttaa   19320
tgtactaatt ttgagaggct tttaaataga gtgcactata gaacttttc ttggcttcaa    19380 tttgctacaa tgttaataga gaatcagaaa ccttatcctt atagatgttt cttgattttt   19440
ttaatttctg gtgacattta tgagtgagaa tagtgtattg ccctgttttc tttcttactc   19500
ccctttcttc ttccttcctt gcttctttc ttcttccctt ccttctttct cttcctcgct    19560
ccttcttttt tacaagctgt tatgaattag ccttcacaga gaaagaaaaa tttttataaa   19620
```

```
taactggaaa tgaaactttg caaaggactg cagatgaaaa actttgtcaa atgactgtaa    19680
aaatatacta tataattttc aaaagttaga aagtaccaaa cacactcagt attcatggtt    19740
atacaagtat gcatacacat gtattgctcc ctgaaaagtg gtgttgttaa gggagttttt    19800
cttagtacgc ggcttaacat atttttttct gtaatttgtt gttagttata atggggagag    19860
aaaacaggtt agagtctccc ctctcagttt caccttccat aaaacagcta aactagacga    19920
tcgtcagact ccttccagct gaaaacatct gtaaaattaa aaacaaatct aaatgtatgc    19980
aagatatgta tttaaacatg ctggtaataa gtgtgctgtc cctataattt agatgctaaa    20040
acattgatgt cataataata acaacacctc gcatttgtac agcacctcat agtttacaca    20100
atgccttaac attcttctct ctcagcctcc tacaaccca caggattggg atagctttcc     20160
agattgggag gtgagggacc caggctcaga gcgattctgc tgttgtccgt aatcaccagg    20220
ctggtgatca gtgggcactg ggtgctctcc tgctacacag cactgtctct caacatgcag    20280
gtcaaggtta cttattcctc cttcaagacg tcattgggtt ttttagctat ggatgcccca    20340
tcacttttag ttctatttgt gaatcaaagg ctaaataaag tattcctcaa aatttgttat    20400
acttctgtta ctaatgctta atgtccctca caatttctgt atatttctgt gtatttctgc    20460
tctgttttgg ttccttccc aggtttcttt tttgttatga agtagttttt agactcaagt     20520
ctcttctgta tgtgttataa ctgcccattc cataagatac agggcagtga atttgtgagc    20580
cttgaaaata tttactttag aaatgagaag tatgactttt caacgttgtg tcatcaactt    20640
ctgtaaattt tccagaccta taaatacttg cagaaaaaaa atgaaaggag aaggcaactt    20700
gatttagcag ttgggtcagt tagcaatgcc tatggcaagc tgtagtaatt cccttacata    20760
gatttgtaag actcatttct atgatttaaa tgaaggcata cacttaacct ctttagggtg    20820
tgaaacagct tttacaaaaa gagacaaact taagaaacag tgtggccctc caagagtgtt    20880
cattttccat atcataccat ttgtaataag ctattctggc tgggatttac ttgcaagcat    20940
tggctttttaa gaagagatgg tttcacacat caaattattc acttggaggc actttctggg   21000
ttgaaggaat ggaatggaga gtgcggcagt gagtagatct ctcagtgacg gtgatgtgcc    21060
tctcccagaa gaaatttcaa aatgcagtgt tcattttcct ccacaagaaa ggaagaaact    21120
gttttgttat tgtttattcc taacatagtg gaaacttttc agtactctgg cagaaatttc    21180
ccaaaagcaa ttttctattt catgattata aagtagcaaa ggaaaaagtc ctgcactcca    21240
gctgagcaat ggatctccag ttgttatcta ggtgctgcag gtttagagag gattgccagg    21300
agaacacatc gattttttcag gcctgtgatg acgtatctct tgttgaataa gtaaacccctt   21360
ccagtaaaca gacagttagt atattgattt cagggtggct ttagccactg aacctgtaag    21420
tcttgcaaag gttacttggg caaaagcatc attattttac cttcagtcaa caaaaatcta    21480
cctggccaag gcagaacaga aagttcagca atttgatgaa gtgggacaac atgaagaatc    21540
aggtgagttg cctactttttt cacttcactt tccaccttta gagattcttg tttagatgca    21600
gagtagtgac gtgcctggtg tcagggagag agttgaatga gaaaagtccc agaagggcag    21660
aagacttggg tgattatctg agtccatctt tccttatcac atgacagagt tcttgaagtc    21720
ttggctagga attctaggct tttagattct tgggcaatg gctactaaat gttcataatg     21780
ttgctcagtt gcaaaacaa gacattcaaa ctatagccag ggagataagt agtcacgaac     21840
tcaaggccta aattctgctg atggagccga tgagaattgg gtgctaaggc aaagagagtt    21900
gccaatatta tattcttcgg ggttttttgt tttattcgc attttggaaa aggaaaatat      21960
tagcattcct ctgacttaat attgagaaga cattgggcac tcttttttcct cccacacttg    22020
```

```
tcttctttca ctaggtgaca agggaagagg tagcatgagg tggtggtcac aggtgagagg   22080
ggctgttgtg agcacaggca tgttgactgc acattggtca cctagtagaa gttttgcagg   22140
cttggtgact tctgaacact gttttcaagg ttgatttta gttgagagaa cctctaggta   22200
ccacgtaatg ttattaacag tagtactgat ctcacaatcg ccctatgtcc cattcacaag   22260
atgttctgcc aagccataaa aggcccagtt aagtttaaga gaagtctcaa agtaacagaa   22320
tgataactaa ttaataccca gtgatttga aatgtagaca tcaaacatac caattcagtg   22380
gtatcatcct tagaggcaga cagaggatga ttaaatcatt cagcccatct ctgtctgagg   22440
acgcagctta gcacagcatg gtggaggcta atgggcctt aagggaaaaa atgatatctg   22500
aagatgcaat ttatttcaaa aagagtttgc tcccgtgaat tttcactctc tatgtagaac   22560
ggcaccagca cacactttc ctgagccttt gcatgtgtgg caggcagcgg cctggcatcc   22620
tggggaactg aatgaggacg cagatgaccc ggacgtgttc acagtttgac acatctgact   22680
cccagatcag ggacagctag ctttgctggc tggttaagtt gatgattcca tctttgcctg   22740
gttctctgac tgtctcatgc tttctgttat tactattttg cagcagatat ttctgctcat   22800
ttttcaatca tatatgcatc ctggatggca tagagttgat tctcctaaca aatcagtgtc   22860
cctttgtatt ttttctggc cataagatag aatatatatg tcatttatta aaaatggaga   22920
aaatgttcag gagtttcttg actcagagag ggaaaaggga tactcagggc acttttcag   22980 ccaggaattt actacctttg cagggtaaag gggactcacc acgctggaag tcaaaataag   23040
ccaccagtgc caagtgttca aagcccttag aatcacaatg ctcttaaagc aaagtcttca   23100
acaatgcttg aaaacttcca ctggttctca gtatgtccaa aattgtcatg tctatgaatg   23160
attttctcaa tctgaaaatt tttatagcag gctaaagaat gagataggtc agtgtgattc   23220
tagaactaat cattaacatt caatagatga ctatttatt ctagaaaag cagcaacttt   23280 ctatttactc tctatttga gggtaaattc tctgtaagta gaaaaagcaa aatgtggaca   23340
tgggactaac atatgaatat acaaagcaaa tgtaccgaaa aaatcttaag acctgccttg   23400
tggtgttttt tgttttgttt tgttttcatt aaagtgactt gttagcctct tgctcctgt   23460 gaagcacagg gaggtgacgt gatgtgcaca gggcagactc tgccatatgc cctggccttg   23520
aactcagggc cccctgggga ctgcagggga tgctggccat gctgagcaat gcctgtgggt   23580
gtcagtttcc tcatctgcag aatgaggta ggcctggtgc ttatttcata gggtcgcaga   23640
ggggattcag tgacagggtg gtgtagaggc tggagcgtgc cccatgtgtg cacgacagcc   23700
ttccaactag gggaggcggg cctgggctct caccagagag cctgtgttct ccatggctac   23760
atgactttgc cccagacgtc cttcccgtgg tctggaccct gggaagtcgc caagagccag   23820
acaggagaaa ggctccactt ggctctcctc ttttggtgacc atcccttgcc tccatggcgg   23880
gactctcagg tgacatccca ccaaccctca ctttgcttcc ctggtgggtc tcactttccc   23940
tcaagagtgt tgcttttttg tttcctgcat agtcctgggc cagttttgat aaccctcttc   24000
atttcacttc agaaaccctg atgatttctt cctgtgctct ttttaccttaa ggacttttac   24060 tatgacgact gtgactggcc catttcttgt ttttttctc ttgctctgct ttctccccca   24120
tcatcactaa agcagacatg gcaatgatgg ccatgcacac tttccaaggg tccagctgta   24180
gatcttcatg gttccccagg tgcctggacc atcttgtgag gagggaggca aacacaccct   24240
gcctggagca cttggcccctt tcggcaatgt tttggcttcc tcaagtgaga aaagaatgga   24300
tttgtattcc ccctctgcat tattgttttt gttttgtttg tttgttttgt tttgtattga   24360
```

```
gacagagtct cacttttttc cccaggctgg agtgcagtgg cccgacctcg gctcactgca   24420
acctccacct tccgggttca agtgattctc ctgtctcagc ccctgagta gctgggacta   24480 caggtgcccg ccaccacacc tgactaattt ttgtatgttt tgtagagaca gggtttcacc   24540
atgttggcca ggtgcccatt attatttgat ctggaattaa ctgagctact gcaggaattg   24600
cttgattcac tgatgactgg tgttgagcca gtacacaccc acacccaagg actgtgactg   24660
tcttctgagg tccatcctca gaaattcctg tctcttcacc tagtgtgtaa taaggcctgc   24720
gcgtgttata tggaactgta aaaaatgcgc caaccatctg tccttcctct ttatctgatt   24780
acttatcatt gttctctaag ttgcaagtta atagactgat cataaattaa tgcatgctgg   24840
agacttgctg tttcctacta gcagcatata aaagttattt ttaaagttgt tttaaatctg   24900
tgagtaaaaa taaattgctt tgctgcaaga aacaccaaac atggaaaagc taacggttca   24960
aagttaataa tttatcttat ggacatcact agtggcatag ttgctttaaa cagtgagagg   25020
atttaataga tatttgattt gcaagtggga tgaaggtgg tctaacctttt gtcctgtgtt   25080 taccttccat gagatcctag aggttgtaca gcacagtagt ggcatgtgac acacttgaga   25140
gtgcctgttc tgtttggaaa cctggaaact atgaagggaa gtggccttcg agcttaacac   25200
ataagacttg ggaggcaaaa cctttttattc tctttaaata ttcactttag gataagcatt   25260
tttttaggtg ttaggaacag ggaaaactgt gtggttagga aggaagaaag aagaaagtta   25320
actgttgtac attccctagg taatgttttt aagcattgtt attcactttc aaaacacatt   25380
ttatttattt ggacttaata ttttgatctt atttttttcaa tttctttttaa tttaacagac   25440 aggatgagtt ttttttatagt tgtattactt agaaaattata ctaaaaatgg ccgagtgtgg   25500
tggctcacac ctgtaatccc agcactttgg gaggccaagg caggtggatc acttggatca   25560
cttgaggttg ggagttcaag accagcctgg ccaacatagc aaaacccgt cttcactaaa   25620 aaaaaaaac aaaaaaaaaa ctagccacgc atggtggcag gtgtgcctgt aaccctatct   25680
actagggaga ctgagacata agaatcactt gaatccagga agcagaggtt gcagtgagca   25740
gagattgcac cactgcactt cagcctgggt gacagagcaa gactctgtct cggaaaaaaa   25800
aaaaaaaaag gataaagaaa tcatactaaa aacaaaacag aatgctgacc accttataga   25860
aatagaaata gtggtttgct gtgatagcaa atttttcttgt taacttttta ttttttaaaga   25920 attgcacatt cacaggaagt tgcaaaaaat ctactgggag gtcctatccc ccttcccca   25980 acctcctcca gtagtaacat cttagtagca aagttttgta tatttatttt gatatcatta   26040
tctaagtttg acatcattat ctaatattaa cctaagccaa aagcccacta ttttaattat   26100
ctagtgatgc agtgttatag aactcatagc ctttcacagc attattgga agttaatttt   26160 cttaagtgaa atgtttttgg tctttaaggt ttggaggcca tggaggcatg aggagaaatg   26220
ggatgaggga gagagagcta agatagataa agacagagat ggggagatcc actgattcgt   26280
tgaacaaacc agatacttcc ttatagtttt tggattaact tacatgagct aagtttatat   26340
tctgttcaga tcacaagtgg tcaagtttgt gtgtgtgtgg gggggggggg gtgggtgtgt   26400
gtgtgtacca ctctacccat cctatattta ttgtcctgta tttggtctgt tctgccttct   26460
ttattttcag gataggtgtc ctaaatgagg gtctttggaa agctggtgag gccatgttgc   26520
ccgtttcagg tgttccgtgc tcaaatgtat tcatttcttg aaaaattcag ggagtgcaca   26580
cttttgtaca ttttcctatg tgtatatgat accattatat aaatcttaaa aatatatatg   26640
gttcacctga atcccagcc atttggtaga gaagatagaa aacctacaga ggaggctaag   26700
attttattag aaaattcagc ttctcgacgg aggtattggc tttaaagtca aggcaatgca   26760
```

```
tctattctttt cttttgatat aactagctaa aagatctctt aaattcaaag tggccctcat    26820
cttactgtta ctgcaattta ctcttaatta caaattatat aaaaataggt tttgaaatac    26880
tgtagcgaca aagtaacata cctctgctcc attacacaga taaaacctct aaggaacacc    26940
tcctctctta acaggcatta accaactgca gaaactgcag aaggacaggg ctatttggga    27000
ataacacagc tcccttcctt gtctgttccc tcccattgtc aggcttctgt ggagccatat    27060
tcagagcaac ataggagggg ggaagagaaa atcaaccct tggtgaagga aagctcccaa     27120
ttcacagagc aaacatgggt actcttgttt gtgggagctc ccagggcctc ccagctcacc    27180
gagcattctg agccctgatc cttacactaa ttgtattatg caaccataaa tgatgtctgc    27240
tgtaccagcg gggacagttt attttaatag attggtataa cttggcagaa tcttatctgc    27300
atgtttcatc ttggattttt agctcaattc aactcaatag gcatgtgtca aatgtctact    27360
gcagactgag cactgaaaag ctgctgggta cagggttaca tggatagaaa acgtagcctc    27420 tgaccctaa ggagcctgta atccagatcc ccattctttc catcccattc tcccaagcaa     27480
gaatttacct aatgtggttt gcgagaattt aagagctgga aaggtggtca cgagaagccg    27540
gaatgggttc gctaaaatgt gtctatatga ttaagcataa cgtagctttg cagcactctt    27600
cacagcttcc tcagagcctt ccgcacgcgg tgtctcattt gaatacttgt gtgaggatag    27660
cctcataccc ctcagtgagc tcttcatgga gtgatgcagt agacagcaag cctcacactt    27720
ctatgctcac ggaagaccaa atttgccttg aaaaatcttt atagtctctt cacatttcta    27780
agttgacatc aaaaatcggt taccataaaa tcctaatagt tgaagagatg taatttcaat    27840
tatttggtaa acctgacctt cattgtcaaa gcaattagtc aactcagatt tactttctcc    27900
cagataatag attctgactt cttttttttct gattaaaaaa cttaacaccct tcctcaggag   27960 atctatctca gttctgaatg ctgattctaa ctaagaagga tatttggcta catgctggga    28020
agaggggtac tgaggcacgc cgcgattcca ctccagcatt tccagttagt cgggtgcctc    28080
tgcactcccg gtgttccggc gcccagttag ttgtgtactc tgggctgtcc ctatactgga    28140
gtcctaaaac acttacgact gcagataggg ggaggttttt caaaaccttg gtctgaaaag    28200
ccatagaagg gagataggaa agcgggggggg tggagccaca gtacattcag gtggatccgt    28260
ttttggaaat agtacaaact ggaggtgaaa ccctggaaat tgatctgtcg ttcacatgct    28320
tcatgccgag tccttgtgga cccacagaga cacactcgcc ccagtttgaa ggctgctaac    28380
ttgattctga ggacaccagt gaggtggtag tgtgcaaatg atgtgtgagg aaactttgga    28440
ggagtctcac cctgcctgga gcacgtggcc cctaaaacag cgcagcctcc caaagacaga    28500
agatgtggac tagtgagaag ccaggtatgg tgactgctgc tggatgaagc ttgtcccacc    28560
agaggctcgc ttgtttcatt gagcacctac tgtgtgcttg tgggatgcaa acacacgtgt    28620
ggtccctgcc ctcaggttaa taggcagggg tggaacagtt atgaaactgc tctaaagtca    28680
ttttctcaaa ctgggagtga caaatgtatc cacttggaaa agattgagaa ttttataaga    28740
tttttaaatt tttgtttatt cacattgagg agaatctaaa ttcttttgaa cttatgtata    28800
gatttcacca ttttatagta ataaatcagt cctcctgtgt gtgtgtgtgt atgtgtgtgt    28860
gtgtgtatgt aaacctcacc ttgcaatatt attattttaa atagccactt gcatcttaag    28920
gaaattaaga ggacaaaaga aaagctgctg ttttgtatgt atccacatat ttaccagctg    28980
cttccctgcc ggcaggtgct ctggttctgc actgcctgtt gtcccttgcc tgaaaatggt    29040
tgcctccaat attttgctca gttttctgat tgtttacagt ggcagaggag ggtagatctg    29100
```

| | | | | | |
|---|---|---|---|---|---|
| gtaccagtta | gtaattgcca | gaggtggaag | tctgtggatg | aaatttgtat | aacatggaac 29160 |
| gttagttcca | cagttaatgc | tactcaattg | gaacccatgg | aaattatttt | ttggtgaaaa 29220 |
| gggcccatgc | gttatgaaat | ttgagatcca | tcactttaag | tgaatgtagg | ccctggatac 29280 |
| agtgggagct | cagaagagca | aatcagttgg | tcaccttgct | caacgtattt | tactaagggc 29340 |
| atcagtaagg | ctttctatga | cctgctcctt | caatgcttgg | ttgacatttg | gggagcaaag 29400 |
| ataaactaag | gattctaagt | tctgtcctgt | gatgctgtaa | ggggaatctc | aaacctctag 29460 |
| gtggaggagt | gcagagatga | ccaggatggt | ggaagcctgc | aggagagctg | aacacctgaa 29520 |
| gacacccagt | gggaagacca | ggacctttaa | cgcccatatc | tgctgctcaa | gactggcaga 29580 |
| gagaagaggg | tttgtgatga | gaaaaggtgg | tgaaaggcac | aaggaggcac | agagcatgtc 29640 |
| aggtcccata | tcccaaaagg | aatgtgcttg | ggtgagggag | agctcctcca | tggctggagg 29700 |
| cattcagaga | ccaggcagtc | gcttgtgggt | ttgtgattag | agtgaggttc | ttttataaag 29760 |
| ggagtgagaa | gagaaggtct | gtggatactt | gagtgtatcg | gtaattaaga | aataaattgt 29820 |
| gtacatccca | tttctttcca | cattttcctg | ggctgtcaca | gtggctgcaa | agaaagcagt 29880 |
| ccgtgaactg | aactgtgatc | ccagacaggc | aagcacacca | ggaatctctt | ctcagctgtt 29940 |
| gataatgagg | gagcgctggg | gagagaaatg | gggtcctctt | tgagtttcct | ctgtgccgat 30000 |
| acctttctct | ttgttaaaac | agctaattaa | acactgaagc | agtatagctc | tcttactata 30060 |
| cactggtagt | catagttctc | ttactgttct | cttcactgac | agttctctta | ctatacactg 30120 |
| atggtgacgc | agaaattcag | aattccccgc | atgtgtcccg | gtttgaaagc | cactgtgctt 30180 |
| tgctgtggat | taggatcaga | cagttgagtc | ttgttccaac | aaggaaagtt | gcttattgga 30240 |
| aagtttgct | gcagggagcc | ttgagttctg | catcaggctt | ggaagtgggc | tctgtggagg 30300 |
| tcagaaggag | gatcccccac | ccgcagcctc | aagaaaaata | tgaaaagtgg | attatgcctc 30360 |
| tgtagctata | ttgcctataa | acttctgca | gaatgacagt | attcatatcc | tacatttttt 30420 |
| caaagcgata | ttaatcctga | gacctgcagc | taaagtcaag | tagaatttag | ggataattaa 30480 |
| taggaggaag | gtggggttgg | aagatctgca | tgattatagt | cctctgatat | aactggaaaa 30540 |
| ttctttccat | tagcaaggag | ctttggttaa | tataaaatgg | acagattaaa | cctaggcaat 30600 |
| ttatttact | cattgctgta | tttttatttc | agagctggtt | gaaaatatta | caaagtaata 30660 |
| ttttaaagtg | cttatctaaa | ctcttactct | gcattttatc | attgggttat | gaaatgactg 30720 |
| gggaaagact | tttcttgctt | ttatttctca | gtgtctactt | ataaacatgt | tttttgaact 30780 |
| actgttttg | tgacaacatg | ccttttttccc | agaaaatctc | aggttaacat | taaataggca 30840 |
| ctggatgttt | atctgatctt | gtttatagaa | acacaagaaa | attttaaccct | tgtatatact 30900 |
| ttactcaatt | aactaggtaa | gaggtcattg | aaacatttag | aattccactc | tacatttcaa 30960 |
| taattatcag | gtgaaagcta | ctgcatctac | atcagaagat | gtttgtaatt | tatttaagaa 31020 |
| taaaattagc | tatgcaagaa | atagtatgtg | gagtcctatg | tggaaatcac | agaaaccctg 31080 |
| acaacttgat | gatctttccg | caagctaaaa | atatcactct | ggatcacagc | agtagaggac 31140 |
| tctgtaaatt | taatctgtgt | gtctcctgta | aataagtgca | ttagcagtac | acaggtggtg 31200 |
| tcagagtcag | tgatgatgga | tagaaattct | acataaaatc | caggctcagt | ggctcatgcc 31260 |
| tttaatccca | gcactttggg | agtctgaggc | gggtggatca | cctgaggtca | ggagttcgag 31320 |
| accagcctgg | ccaacatggc | aaaacctcgt | ctctactaaa | aatacaaaaa | ttagctggat 31380 |
| gatggcacat | gcctgtaatc | ccagctattc | gggaggcgga | ggcaggagaa | tctcttgaac 31440 |
| ctgggaggta | gaggttgcag | tgagccgaga | tcacgccatt | gcactccagc | ctgggcaaaa 31500 |

```
gagcgacact ccatcgcaaa aaaaaaagaa gtaagaagtt ttacataaaa acgtggagtg   31560
agcccaaggt gccatttatc cagcccatac acatcgtacc atgtacagag tggacaccag   31620
ataaatacat tgactgcatg ccacaaacat atatatgtag gcaccgttgc attcaaatac   31680
acatctgcag ccctaacaca tctttatttg ctaacgagca tcaatgtatt taaaaacaaa   31740
catgtttaaa ctagtgaatg attagattat aatgatctta attcataagt tttctcattg   31800
gccttttgta tacttcaatt gtaataccta gaaaaacagt tatgtccaaa ggagtgaata   31860
ggccttatct gaaacaggtg agcgtgacaa gtgttttctt acttatttta cttttcagat   31920
aattcatcct taaagtacat tagttttaaaa gtactgttta aggaaacagt acttggatta   31980
aaacttgaat cattgttaag gaaaactata ccttaacttc atgtaatcac aattaaacct   32040
cttcatatag aaggatctaa gaattttctg cagcattcac cagcaccaaa aagctcagag   32100
acatatattt ctttctctgt atatgtattt taaattcaag ttagtataaa ttgacaggca   32160
ggtcagagta atatatgatc ttctgagtcc ccttagtaat taaaagaaat gattattttt   32220
gcatgaaata tgataaagtg attttaagtg cctgataaaa agtcttaacc atgacaacca   32280
ttaaagatta catcaaagaa aaataagttt gactttcatt taccttggaa acagctatta   32340
actggtaacc tcaagaaaca ccatgaagag tcagtttgct ccacacatgt cttgtaaaag   32400
tcaaataact ggtggttatc cagtaatgac aagaggtaga agttacatcc ttgctgtctg   32460
attgaacctt cccagagctg gcacaaggct gggaagacca taggtgctaa atgaggaact   32520
acttaaagaa agaaaatgga atttcacgga caagaaaatc catgtccatt tggttctgtg   32580
acccacatcc tttgtatcct atgctttttt acacttggta catggttgca agattgcccc   32640
tgttttctac ttatagttcc atgcagcatg gatgtgggaa aaagtctcct ctgcaaaggg   32700
ggttaatgca ggtcactcta cgtatgtgca cgaggtcgtt ataaagctcg aaaatatggg   32760
ctcaccaacc aggtgatttt tttaattatc caaccagaag acataacata tagggggaatc   32820 aaaagaaatc tctgagtaaa ataatgataa caggtcaaac tttgcggtcc cacgtgaggc   32880
tggagatgcg tattgtcttg actttgcatc tacaagttta acaaatgatg ctttctcagt   32940
ttacctctgg aaatggaaat tagcattgca aatgacttca tgaggaggta gaagctatct   33000
gtgaatttcc tttcgctgtg tttacgatag actctcacgt ctagatgtgt catgtattat   33060
gttaaattgg tatgtcttga agttataaag cacagccctc tataagtata tatattccac   33120
ctctttcaaa tcggatggta cctatccttc aaactgctat ttaatgactg tctgctatgt   33180
tcaaggcact gctctcaatg ttaatacttg atgagatcgg gcgcgttcaa ggtggcatgg   33240
ccgtagactc aatgttagta tctgaaatat ggcctacgag ctgagttgtg aatcaagtta   33300
atagattttc ggaatgttaa ggtctaaacc agtagctctt aactgagaca atcctgtcct   33360
catctcacct gggagacatc tggcaatgtt tggagaacct tttggttgtc acactgggggc   33420 atctagtgag tagaggtcag ggatggtggt aaacaagttt ttttgtttgt ttgttttgtt   33480
tttgagacag agtctcactt tgtcacccag gctggagtgc agtggtgtga tctcagctca   33540
ctgcaacctc tgcctcctag gttcaagcaa ttcttatgcc tcagcctccc aagtagtagc   33600
tgggattaca ggtgtgcacc actacactca gctaattttt gcattttag tagagacggg   33660 gttttgccat gttggctagg ttggtctcga actcctggcc tcaagagaac cgccccttc    33720 ttggcctccc aatatgccgg gattacaggt gtgagccacc gtgcccaggc taacattctt   33780
taatgcatag gacagccccc accatacaga ggaatccca gcccagaatg ttaatagttc    33840
```

```
taaggttgag aaacccaagg ttaagccaag tcaacttatc tatcttcttt aaaattgcat    33900
aagaatgcag tcctgttctt cattcctctt gctttgcagt taatgatcct ttgcctggac    33960
tttctaagtg cccagaagag caacagccag catgcaggat ggcattcctg accagttgca    34020
cttggcctag cattccaacc tcacctgcct cagcttgttc aacctgaaaa cctaccaagt    34080
gaaagcaaga gccacgtgaa gacgccttag ttatatgcac ccacccagac acttgctcag    34140
aaaggaatca gtggggccct ggccttagaa actggctcct tcactgctgt agaaacaaca    34200
taaatttaac ataaaacacg tgcttttctt ttttcttctt acttttcct gtcttggcaa     34260 tgcaaggatg ccattaggta aagaaatcct tcaccacact aatcctgcag agccagaaga    34320
gaaaccagct tgttctaacc cagctttgtc atggagagaa ggcagctgct ccagtctgaa    34380
ctattctttc ttttggtagc agcctgccca agggtgaaag tgtgtttaat agtttgaatt    34440
acacaagtga acagtaaatg tatgcctgtt tctgctttat gggactttga aataatgttg    34500
tttgtgccaa ggttttagat tactatacct aacaacctag aaaagaaat gaaaggaag     34560 ccttctgcca ggcagaggtc actacgggcc tggagctggg cacctgactc agcagctgcc    34620
cagatcccca gagctgagaa gtcaccatgc atttgtggtg cttcgagcga gttaccagag    34680
tcctggaaca gagcagcaca cctgcggggt gtccccttgg catttgggca gggcaggtga    34740
ccaagggtct tgttggaact gaagtccagc ttgaaaagca aatctggttg tgagctagag    34800
tccagtaaca cttgtttccc gccgccccc gcataactcg tgtgtcctaa aatacaataa     34860
tttcttgaac ttcagtcact tatgcctata agcgggcata caacaggggc acaataaatg    34920
tttgttaagt gaatgaattc tttcagaact agatgggatc ttagtccaac tctcttattt    34980
aacgaggtcc acagaggttc tgcgattgtc taagaaagaa ggctgtgttc atggcctttg    35040
ttgtttacgt ggccctgtga ttctcttggc tccgtgaaag tcctgatgca gacattccgg    35100
ccatctagaa aggcatgcag acaagccatc cagctggcat gatcctgagt ccagctttct    35160 ttaaagagc ttccaaaact gcttaagctt tgactgcaca aaacctgcat cacctccagt     35220
tgagaaactc aagagaataa gtaagttatg gagttggaga ccccagctta actactagtt    35280
ttaaaatagt gaaatcaaca ttttcaaatc tttgacttca ctaagattta ataaagttta    35340
ttaatcatat attatgagtt attgctctct ctttatgtct gtaatgcagt tgctcctctc    35400
tgtataaatt aataagtttt agagatccaa aatgagaatt ttaaaataaa ttacgtatat    35460
tttaatcaag tttaatttga ctatatccag ctaaacaatt gattgaactt cacttgcttt    35520 tctatgcacag gttttttgtt cttagtaaaa gaccccagtt ttctcacttg tgaacagaag    35580
gggttagact tcatgacagc taaggttcct tccgtctcta acaaaagtgg cctgaagaga    35640
ggcttctaga ctatactcac ggtgggttct tgggacctca gagtcagctc catcacttaa    35700
gtggctgtgt gattgagtgg agacacctca atctctttgt gcctcagttt cctcacctgt    35760
cgagtgtcaa catgatggca cctaaagctg ttgagacttc agaaaggtaa tgtgtgaaaa    35820
gtgaaaagtg cctggcatcc aggaagtact caataaatac caactatttt attgctgcag    35880
ctgttcttat agatgtgatt tctagaacat tgccttctaa tagggtagcc atgggccaca    35940
attgttggct gttcggtgtt tcacatatgg ttagtccaaa ctaagatgtg ttgtgagtct    36000
caaatacaca ctggattgtg aagacttagg acaaggaaaa caatgttaat aaaatctcat    36060
tgataacttt taaattaatt acatgttgaa atgaaaatat ttgggacata ttgagttaaa    36120
taaaacagga gattaatttc ttctgttttct ttctactttt tttattagtg tggctactca    36180
aaaatgtgac attatgtatg catctcgtat tacatttcta ttggacagca gcgctctaga    36240
```

```
cagtactatg ggtagtatct gtggggaggt tctcagaaac atgtcgcatg ctcttttaga    36300
accttaaagt attcctagtc tcctctactt ccagcccttg gctcttgggc ctcagtcttt    36360
ttacttttgc ggctgtgttt ctctgaaggc ttggcattag tagattgaaa agaataacca    36420
tctagggaaa tgtgaattca gtttcttttct gacattctgc tctctacaag gggatattat    36480
gtacacataa acctacttcc aaaataatga agtgaggcct aattccttac tcttcagaga    36540
gcccactgtg gaagtgtcac tgaccttgtg tatgggctgc ccttcatggc tctgggagtc    36600
attataaagg gcagcatttg gcgtggtgcg tcctaagcca gtgtttctcg gctctgttcc    36660
ttagacatgt gttagtgtta atagatgttc ttggaaaaaa aaaaaaaaaa cagcattctg    36720
aggtcaaaca tgctcagaaa gcttggaatc tgcactacgc ttctcgtaca catttcatat    36780
taaagatttt ggaaagtcct gcaatacaga gccctgtcta atattgccac aacccacaat    36840
tgctcaaatg taaatagatt tgagtttatt cacattcaga tcacctctta aggccccacc    36900
tcccaatgct gtcacaatgg caattagatt tccacatgag ttttggaagg gacattcaga    36960
ccacagcagg ggaaagcagg gtacttgctg ctttgcaagt gtgtccacat ctaattaata    37020
gtacagttct tactcttggt gtgtccggtg atattaaaaa ttaatgtgcc ttatttagat    37080
aagtaacata aaaatcacaa aatgtatgcc ttagatttat atgtatttat aactagtcta    37140
tttcctgaaa acagttgaga caccttgtaa aagttaccgg tacgataggg ccattccaac    37200
aaagctgtaa agtggtgata acacagtcat aaagaagagg agatagctct gggagaaaag    37260
gtggcccaga aaccagctct gagcctcatg gctgcaggca aggtctgcag gttcctggtc    37320
ctgattgcag gccatttgct gccttgagtg gtggttacac aaggccagcc ctgggggtat    37380
cacccagaac acctagtaca cgaatttcag tttagaggac gaagcattac tggagtattg    37440
ttatgcagga aaacttttttc ctaaaaatgc cctgaaaaga gagtagccta atgcattcaa    37500
tcaaaatgtt tttaagtgga aaacatattg tgtgtacttg atctggcctg ctgcttttaa    37560
aagattaaaa ctgggactgg gcatggtggc tcacacctgt aatcccagca ctttgggagg    37620
cagaggcagg tggatcacct gaggtcaaga gttggagacc agcctgacca agatggtgaa    37680
accccatgcc tactaaaaat gcaaaaagtt agccaggctt ggtggcgcat gccggtaatc    37740
ccagctagtt gaggggctga ggcaggggaa tcacttgaac ctgggagccg gaggttgcag    37800
tgagctgaga tcgcatcatt gtactccagc ctgggcaaca agagtgaaac tccatctcga    37860
aaacaaacaa acaaacaaaa aaacactggg gccaaagaac tctgtgtgct gtatcaccta    37920
accacatttc atgacacggc tagagaagaa tcatgcaaat aaaaatttcc aacatgttcg    37980
taaactggga aagtatttca ctggggagtg agcagaaaag taatactata acctctatat    38040
ctagacaaat gtgaattcag tttcacatat aaatatataa gtgaaaaaat atataaatat    38100
aaataatatg aaataatggt tatctcacca ctttctacat cttttgtgaa tattttatag    38160
tgctcaaata tattagtgca ctagtatatg tacattacat taaataacta atcatttatt    38220
aggaggatgt gcttgttttt tgctaataaa gatgataata aaaaaatcct tagaccccccc   38280 ctcggtttgt tttcagttag gaattaggga tatttataag aatatcttta aatgacacat    38340
gccttgctct gggacgaggc atctgcatgg gtgacacata tgtgttgtgt gtacaggctc    38400
ccagcatttc cagggccctg ctcagaatgt aggccttact gattcttaca gagttacaag    38460
cgctggtgag gttggcgaag tttaggtaaa cacagctggg aatgccccat ggcctctggg    38520
tgactttgga catcactgaa ctttacccctt agagatgcat acctgcatct tttttaccct    38580
```

```
gatagggcct tccatgatgc tttcaaagtg tttttgtctg cttttcggtt aatagacttt   38640
cacagtagcc aattgaatat attggttaaa tgcatctctt tatacacaga ctggattcaa   38700
actgaggttg tgtctctccc tggctgtgtg acgttgggta tgatccaagt gtcagattac   38760
tcaacttcaa aatgaggaca gagcctttcc cttctagggc tgccaggaac attgaatgag   38820
agagtgctgg cagcttagta caggtgttca ttgctcttgt atggtactgt ctgtggcacg   38880
gctagataaa atacagtagc cactgattca aatttcaact gaggagtaaa ataaactgaa   38940
taacttagaa aagttttctt cttttgaatg actctaagaa tttaaggagc atgtgagtgt   39000
tgatggctct aaaagggtaa cagagcccaa ctagctcagt tctcagcatg aaaatagtca   39060
tatggcacag actcagtgga gtgggtgcac ttcaataact ggaagcacag atgccctaca   39120
gcagcatcaa agatggcact ctaaactact ttcaatcctt taaataaat ggaaacgcac   39180 atttagtatg catatgacaa cacgaaggac ttcgattttg ctgatgcaat acagttttac   39240 aggattttt atactcaaat tagtaaaatt ctgtattgca tccaaattat aaattataat   39300
atcatctaga ttggacatag gaataacgac cactggtatc tgcccagaaa gctctaccgc   39360
ctgtttataa gctcctgcag gagacacaaa aagaagagaa tttgaatata acttgaaatg   39420
accgtaatct cctgccccaa ctcatttcat taccaaaccg cctctttctt cattatttct   39480
cctgaagcac aaatctatag agaactcagc tgccagtctc tcccactgca ctcagcagtg   39540
aaagggttag gcctaggctt ttcaaacaga ccagtgcttg tatcagccct taaacatctc   39600
tggagaagga aatgggatcc ttcttttggta attcattttt gacagttggg gattaggtgt   39660
tctgtatctg gggggccttg ctgtcttctc tcctcctcct cccactgcag accctctcct   39720
cccctcccct ctccagctct ctgatgactg cttcatgctc cttccacctg aggactgcca   39780
gcacagccta ttgcaggaac agccaatgag gggctggctg tgctctttta tttataaaat   39840
tataaactca agcaaaatct agactatgtg tccccaagat cagaggagca caaatccctt   39900
gcttacagat tgcatgggggg gcacattctt taaaattggt ccctgatcta gactctagcc   39960
tgagaatcat cttttaagttc agaatttcca ctcatgacct cacatctgtg ggctcccaca   40020
ttgtcttcca aaacacacat ggcatctggc atcaccttca cccccaccct cagagcctca   40080
tctccctgca ggtagatagt caaggcaacc tcttcactct tctgccaagc ctcctctcct   40140
cagctcttcc cttcctctct cttttttgaaa atatttttaa ttgtggcaaa atatacacaa   40200
cataaaattt accatcttaa tcatgtataa aagtggagtt cagtggcatt aaatacattc   40260
acgttgttct atagccataa acaccattca tctccagagc tcctttcatc ttgcaaagct   40320
gaaactctgt ccccattaag caatggctct gttttcctcc gttccccag ccctggcca   40380 ccatcctcag ttttctgtct ctgtgagttt gattactcta agcacctctt ataagtggat   40440
catacaatgt atctgtcttt ttgtgactgg cttgtttcac tttccataat gtcttcaagg   40500
ttcatccacg ttgcagcata tggcagaaca tctgtccatt tccaggctga atggtactct   40560
tttgtacgtg tggaccacat ttcatttatc cattcatcca cgggagggca cttgggttgc   40620
ttctgctttt tagctattgt gaataacgct gctatgaaca tagctgtatg cctttgtctt   40680
ttaaagccca aatctgatca agtcactccc cagcttaaaa ccttccactg ctccccagca   40740
gtgggataaa ggccagtctc ccctgtaggt ctctcccgcc agccctgctc agtcttcttg   40800
cttgtcatcc ttggctaggc cttgcattgc catagccctc tgcctctgtt cacgctctct   40860
catcttggag catgagcctt ccatcatctc taccagatga actctcattt cttctttcaa   40920
aaaataaaaa acccaaaaaa cccagagatc ccaactgtcc tggtgtctgc atagtctgca   40980
```

```
gcacacgccc cctccatggc ccttcctcca taagcagaat cactcctcac tgttcctgca   41040
gcacctcctg tgtgcccaca cagctgtcct gcggtgggct gtgtgtgtga gtgtgccccc   41100
tctaggacct gagctccttc tggagggtgg gcacagcatc cattcattct gggaatcctg   41160
gtcggcacca tgctagaact tctgcaagtg agtgcctttg gtgctggccc atgggagagc   41220
tgttggtaag gcatactttt gcagattcca gttgctgctg aggttgttgc tctttgcaca   41280
agtttcttct agtcaccagt gaagtgacat gtgtggcagg catggcccag ggaggctttt   41340
tcataaagaa gaggttgaat ctttgggggct gtggtttgaa tatgtccctc aagcttatgt   41400
gttgaaaact taatcccaaa tgcaatagtg ttaggaggtg gggcctaatc acaggtgatt   41460
aggtcataag gctctgccct catggatggc ttaacatgtt tagtgaggca gtgggttagc   41520
tattgtgaga gtgggcttgt tagaaaattg agtgcagccc cctcttgctt gctggctacc   41580
atgctctctt gcttttctgc cttctgccgt ggggtgacac agcaagaaga ccctccccag   41640
atgctggcac catgccctgg gactttccag ccttcagaac cacgagccag acaaatttct   41700 tttcttttata aattacccag tctgtggtat tctgttatag aaacacaaaa tggactaaga   41760
caatcttctt tcatcaagtt agggtaccaa cctttaaaga ctgccagtcc aaggttaaag   41820 gaaactttc aagagcagtc caaacatgat ctggccctca gctactctcc agggtcatgc   41880
caccctatca cccactggct cacacagacg ctgaccactg cttagtttct caaactgaag   41940
ttttcctcct cagagctttt gcaaaacctt ttctttgcct ggaaaactcc ccccacaaat   42000
ctttagttgt aggttccttc tcatcttgca gaattattag tttgctcttc aaatagtctc   42060
tccagctaga ctatcaactc caggagggca gagttcttct tcgcttcctt cacccatgtg   42120
cccactgagt ccagaactgt atagcagttt gattgaaaaa atccacaggg tggaggatga   42180
gaggaccctg gatcccagcc tcacagcctc ttacttcacc tgtgtgattt tggtcaagtc   42240
ctttattctt cctgggcttt agttttccct tatctaaaat atgagaaaag ttcccctctc   42300
ctgggtattc tgggagactc atgtaaaagg cactgagcca gtgcagcaca tctatgacca   42360
ggaagggtca gcttcctgcc ttgcatgaga cacacattcc cttcttcatg cacagttatt   42420
catgagttaa atatgtattg agaagtgggt tctcaggaga tgatgcatcc acagcattgt   42480
ttgtatgcct ctgtctttga tgtccctgcc tgagtcgccc actttagagc ccttctgttc   42540
ttcagaaacc agacttttct ttcaatagtt tcagtaatca atcgatcaat caatcaacca   42600
atcaacagtg ataataatca tgagtgagcc cctgcccgtg ctggctgtgt cctgctgaag   42660
gcacactaag tgctgccctt cccagaagcc tcaggaagct tgcgaagctc aggtgcatgg   42720
atgcctggtg gaatgaggaa gggatgcagc caggtagaga aatgccctgc catcacttgc   42780
atcagcatct gtgaagagct ggccaggctt ttgctcacag tggttgacac agtcaaggag   42840
caagggcccc gtaggagagg ggagtcaagg gctccgggtg ggaatggagc tggggctga   42900 tgctggcttc tggagcactg taatgtgact gagaaaggtg aaggagccgt tctgaaaaag   42960
aagaaggcag gagctcgcac agctcttgac tcatcttgac ttcttttttcc tgcttcatcc   43020 aagcaggtcg actctctcgt gatctcagag acagagtgaa gtcatgagtg ggaggggagc   43080
acagaaaata agaccttgat tcccagcatt gggagactcc ctgctcccct gagtctcgga   43140
aaatagcacc cttcaaatgt tttagggatc cagatttgat gaagagatgt tattttggct   43200
tttagattct taggagagat ttgtctttct caggtcagga agaaaatgct gcccgctgca   43260
cattcttcgg gacagactct tttaattatt actagtttaa tgtatgtttt gcttagttaa   43320
```

```
ggaaaacccc tgtggtttct tgacgtgctt cagtattcta actcacagct gattcagttc    43380 aggggctgg  ggagatgtcc tcgacctctg gaaaggaggg tgcatctcta gaaataaggc    43440
taagtatgcc actgacactg tctgcataaa cgtgtgtgat ctcaggtcca aaggatgggg    43500
cctggtctaa gccagggacg tgggaaatca ttttcctgtg gcaacttgtg aagaccattc    43560
tgtgaccttg gtgtctctgg gccttctctt agattttcta agttggctag tcagtggagc    43620
tgccatccct cctttgccca tgttctactc ccagagttcc tccaagaaat tgcggagcaa    43680
tgcctgtttc atgagagctg agtttgctgt gtcttccact tagaaacaac actgtggacc    43740
aggaggacac acagctccca gggccatcac cacacaaagt gaaggctggt gaatccgagg    43800
cttctagccc ttgccgggcc aggcccgcag cactccgctc cccaacccag ccgctgcttt    43860
gtcgcaggaa cctcagcagg gcagggtgtt tcctaggagg acatccgatt cccagccatt    43920
cctttcagtg aatcacctga gctcacattc ttttttcttt tattttgaa gctcttagcc     43980 aatctgcttc gcgatgaacc agttttgctt gaagcagaca aacccgattg tcaggagaca    44040
gtgatgattt cttcagtctc tgaggaagag ttttcatttt ccccaattcg caaaaaagt     44100 caggtccctc cctccctccc tctccgtaga atattttcca tgtgtgttaa caatggctga    44160
gcgtggtaga tgccaggaat ttctgtcaac cctcaaagag gaaagccctg cctaatggtc    44220
tgcccgttct tgttcactcc ctgccccagg ctccccaccc gccttctttc tggaaggtat    44280
aaaggctcct gcttatacct ggcactgcac gcttcgctcc ctctgatctc ctgactgtca    44340
tgcccagtgt ctcagcctat cattctacct ctaactcgac cttgagtgac cttgagcaag    44400
tttctcagga ttccacctcc aagtcactct ccctttggga tatgcagcac taagttaagc    44460
ttgcctggaa aacatcactt gaagctggaa accactttt aacacagcgg gaaaagctat      44520
ttgttcagac aggagtgggg tgggtctggg cagagcactg ctctaacttg gccatgccgt    44580
ggcagcagct cctttaatgc cacttttttcc tggcgcgccc gcgggcctg gagctcagaa     44640 agaggggaac gctccctcgt ctctcaacag ttgctccaga caggtcagca aacatggaat    44700
tcagaatgtt cattaaacac tggctgtgtc ttttgtgttc aaaagcaaga cactctctct    44760
gaaccatggc cccacagaga gtgcagaatg tgtgaaacct gccgggaagg tctggacccc    44820
ttgcggggca gtgggcagca ccgtgcctcc gttcacacca ctcacatggc tgtgcctctg    44880
cttccttctg gcatggctgc ttcttcctca ggtctcaacc atctccctca gatgctcttt    44940
cccatgtttg tggctacagg tccccgtgac ctgcagaggc agagcactca ccagcagccc    45000
agcctcgttg cgcacccatg tttgcatttg caggccctag aaccactcca agctccgtgt    45060
ggcgagatgc accctcctgc ccttcactgg ggagctgccc tcctgttcac agcggcacct    45120
gagtcacaca tctggagcca tcctggactg cctcatttcc ccgatggggg gtttccctga    45180
cttcatccat cctgtctttt gggtcccat  aataactgac atgggtcggc ccgtaccagc    45240
ccctgtgaga agggctttaa ctgccttccc accccctgct catcttagag tctctctata    45300
gtgctgctga aagaatctct aaatcagtgg ttctcaacct cagccgcaca ttgagaatca    45360
cctgggaccc ttaaaaaaat cttaactctt ggtccaagaa ttctattaca atcggtctgg    45420 gatgggccc tacaggtatt ttttaaagc tctccagttg gtaatgcata gctagagttg       45480
agtatcgctg ttcaacgtg cagatctggt catgttacca gccttttagg tggtcttctt      45540
tggctttctc tatctaaagt tcaaaaccga acatgtgcgc attcagtgca cccatttttca    45600 actgtgcatt aacacattca gcccaccagc aagatttatg aacctttc tgctgttgta      45660 tataacatat catatgcata atggcatagg ttattgtttt cttcaaaata tatgagatgt     45720
```

```
gagtccttct acgaactgac tcacactgat tgcccaactt cctctctcga ggtctcatcc    45780
tctttccctg cagccgtctc cctcttgcac gcacacacac acacacacac cacacacaca    45840
cacacaccac acacaccagg gtcgatgcca tctaccctgg acttcatctt gaactccttc    45900
gagtgtgagt cattactcct tgtgcacct ctgctttctc ttctcaagat gttcacctgc     45960
ttgaggtcag ttccttgagc gtcttccact tgccatgttc accacagtgc tcaacatgcc    46020
tgaatgcatg gatggcgact tctcagatcc tcagtctcct catctgggta ataaggcatt    46080
gggttggcgg gtccatctgg tttcttccag ctctgagagt gcatttgctc tgtgattcat    46140
tcgttccaca acacttcacc aattaaagag agggtacaaa aggtgaacat ccttggctcc    46200
cagcagatgc tcctcaaaac ctgaaaaatc agataggtga gggaagattg aatgaaaggc    46260
ctcttatgat tctgcagcaa ttttggtggt taagaactc tatggaaaaa tcatcagtat     46320
ttctggaatt gaagtaaaat ggatagtgag cctctgtgta tgtgaaggcc cgcatctgga    46380
acatgaaaga acctgtctga tgtgttctag tcaggaaagc aggtagccaa tactatttat    46440
agaatttaca gaaactgaag attttgtttc tactgatttt caaaatagta ttatgtctga    46500 ttttttttcct cagaaatata cttcctgctc ttctcaacaa actcatttga aaatatgatt    46560
agaacatgat agaattttac tcatttgcca actgcggttc ccatttcaca tattgttaga    46620
attctgcatg gtggctttgc cctttaacca ctaactgata aatgatgtag ttagcttta     46680 aatgtgtgga aaatataat ttcaggttca accataggtc agaagtacac gtgttttgtt     46740
agtctatttg tctctcagtc atctcatgga aaattctcag cttttggtat ggaaataatt    46800
ttcttgaagg caatatttgt tgagtgactg acggaatgaa aaacgccagt tgcgtaagtg    46860
tgaaaaagat ctgggtgttt tcattggatc caaattccac atgagccaac acagcgtgg     46920 tgtggaggct ggagcacatt aataagaaca gtgtcctaaa ttcaggaggt aatgctctgc    46980
ccatgccctg tgcagctcag acggtgtgtg cagtgcagta tgtaacccag gcacatttc     47040 aggggcccac agggagctgc agcttgtaag gtggagtgca gccaacagag cagagagtca    47100
gaatccccgc agagtggttg aaggcacaag gatgcgcagc aaggaagaca gacttatagg    47160
tggtgcgact gccatcctct ggtactgaag gtgctatcat ggagggaggg aagtagattg    47220
accctcctgg ctccagagta cggaactcag acaaacggtc agaagcttac agggaggcca    47280
attttggatc aactttaaga agaattttt aaaagctaga gcaatcctaa aatgaatt       47340 gctctttata aagttgcgaa tgcctcaccc tggaattgct taagcaaagt tgggacgggc    47400
agttgtgagt aatctccttt ccaatccata cccgcaatca ccagaaacgt ggacttccct    47460
gacactgagc acctcttaat taagcatctc ataagtgaac aaaacccagc ccttcaaaga    47520
agtcacttta tttatgtgtg ggtctgcagc ttggatttct tgataatgtt aaataaaact    47580
ccatctactc ttccacaaac acttcaagaa acctaagact tttggccaga gtaacaccga    47640
ggtttgagag aaaggatatg tgtgtgagag gtgtggtttc attagaacat attatttgac    47700
ttcatgttga atcaacactt ttgtgcaaaa tgcagttta ccagcctctt tccttgtttt      47760
ggtcacataa tttaacttaa cattctcggt acttgatttt ctaacataaa atgggattga    47820 gagggaatt ttgaagttcc catggtctgt cctctacatt ctgacagctc attatctctg     47880
cggtattgtt ctcacatta agtgaggtta gcggaggcag aggcctctca ggcctgaaga     47940
tagcctctgt tttcagggaa atactagact gtgagatctg tgacactgaa gcactaagtt    48000
catctcacaa aagcaacgtg ctcttttaa atggttgatc aaagttactt tcaaaggaa      48060
```

```
gtgttagttt tgttattag ccgaaacaag agctgcttta atgtagtata tttaaaatca    48120
tatctcaatt aagatgttat tcaaatacta tttgacccac caatctcatt actggatata    48180
tacccaaagg aatagaaatc attctattat aaaaacacat ggctgggcac agtggctcac    48240
gcctgtaatc ccagcatttt gggaggccga ggcgggtgga tcacgaggtc aggagttcaa    48300
gaccagcctg gccaagatgg tgaaaccctca tctctactaa aaatacaaaa attagccagg    48360
cgcggtggca ggcacctgta atcccagcta ctcggaaggc tgaggcagga aaattgcttg    48420
aacgcgggag gcggagtttg cagtgaacag agatgaagcc actgcacttt agcctaggtg    48480
acagagcgag actctgtctc aaaaaaaaaa aaagaaccac ttgcatatac actattcaca    48540
atagcaaaga cgtggaatca acctaaatgc ccatcggtga tagactgcat aaagaaaatg    48600
tggtacatat ataccacgaa atactatgca gccataaaaa agaacaagat catgtccttt    48660
gcggggacat ggatggaact gcaggtcatt atccttagca aacgaataag aaaagaaaac    48720
aaaataccgc atgttatcac ttataagtgg gaggtaaatg atgagaacac aaggatacac    48780
tggggcctac ttgagggtag agggttgaag ggagagaagc agaaaaaata actattgggg    48840
tactaggctt agtaccaggg tgacaaaata atctgtacaa caaactacta tgacacaagt    48900
ttacctgttt aacatacctg cacatgtacc cctgaactta aaaaaatttt taaaaagatg    48960
ctatgcaata aaattctcaa ttaagaattt aacttggtaa atgttcattt aatgatctaa    49020
aaatatgtgt ctggatggct ctagcaaaaa aataaataat aagtttctca gagatggtaa    49080
ggctgaaata aatggggaaa aatctgaatt gtaatccttt ttctgttgga cctggtgttg    49140
gggtttcaca cttgtgggtg aatgtgggcc tcctgtgagc accagcacaa aagactaaac    49200
tgaacaaaag attaaatgtc acctctaaaa ttctgtgcaa caagacttcc agccacagaa    49260
tgtgcaactc agatttccaa gtaaaaacac accaggaagc agatcttaga tctctgttat    49320
ctccttggca ccagctggta ttcatcctca atgctagcta gagttgaaat aaagagtgaa    49380
agaactttct ctttttattac ttaataaact tcctttttttg agctgtttta ggcttacaga    49440
aaaattgagt ggcagtttca gggagttcca gcacggcccc tgtttctttc tcatggtccc    49500
tgcaggtttc ccctattatt aacgtctgtc attagcatgg cacatttgtt acaattaatg    49560
agccaatatt gatacattat tcactaaagc ccacaggttg cgttaggggt cattcttggt    49620
ggtgtacgtt cttcaggtct ggacaaatct ataatgacat gcattcacca ttactatatc    49680
acgcagagtc gtctcctggc cctacaagtc ccctccttcc ccacctgctc actcctcctt    49740 cccacccctcc ccaaactgtg gcaaccattt aacttttgac tgaatggatt tattcttatt    49800
ctgccttatt gtatgtacac catatttttaa taagataaaa taatagtcta tagtagactt    49860
ctgtaaatac tcaatgaata aatacttgca tgaatgcagg aaaaatcaat cagtcttgca    49920
ggatttctta tgcgttacat cgtccttata agaaagcagt cattctcacc gagatgtgct    49980
gagcagatac tggacatgtt ctgacccaga taagggctgg gtggaagtag ggctggagac    50040
acagagaccc agtgccaact tccaggacct cggaagaact gaaggcagag aggtcctctc    50100
agtgtggact gggcctctgc tggcagccac cagcgggcac agagctgatg tgtgttatgc    50160
cacgtgggga aaacctacag acgattctga gaaaggctca cagggacacc ctctgcccct    50220
aaaagaacaa tttaactcta atttatttct gtcactctgc attttctgac ctttcccaag    50280
tgtacagttt tatatgcatt taactgccaa attgtcatgt gagattatat ggttatattt    50340
cattaatata ttctagtttg ttcagctgtt cttactgggt gaatttgtgt ggtttcctga    50400
catttttgtt tttagtagtg cctcagtagt tttatacata attacgtttc ccttctggat    50460
```

```
tatttcctta gtatctagtt caagaagtga aatcgctgga ttcttgtggt aaattttga    50520 atttcacagt ataatgctga ttttctcaaa gtctcacatt ctaagaaagt ataatgaggc    50580
aaaacaaaca acaaacatct taagttgatt ttttcctagc atcttttcct tccatctttg    50640
cttgtagaat ctagactatt tcatgaaccc aagatataat cagtatcctt cttcagtatg    50700
gccaaagtga gtttctcatt attttacctc cccttcagga aatgactttt catcttgtgt    50760
tttgggagcc atagatggtt ctgggcagga aactggcttt ggatagaccc agcatgtaga    50820
tggctatttg gccttgctcc cagtataacg atgcagttcc ctgtgaaagg gtatgagtag    50880
gttttggggc tctggatacc gtgtggcctg aagagacaag ggctcaatgc caactctgcc    50940
tgtttccaac tgtgtaacca tgtgagcgtc aaaaatcatg gacgtgctct ggttaacact    51000
gagtgggagc tcaacaaatt attatttta attgttactt ggacatggcc aagttgacta    51060
cactttatgt tctgctacct gccagtctga aagtgacgcc acagaaggtg aaccgcatgt    51120
tgggagatgc tcctcatctg cttaaatgag gtgcaaacac agcccatgcg cctgctcttc    51180
atgactgtat ctgtaccagc aatatttgta ttggcaaatc acatgcccca gtgggaacta    51240
cttaagggga attcaatgga tttcattcct tttatgtaat tggccactta gtaatagacg    51300
tgtaggtctc ttgtgtggat aaggattctg ccttttatgt aagatatgtg ttgcaattca    51360
gctttcaggt cccagccccg ggaaggctcc aggccttcac aaactggccc acccacgaga    51420
aggaaagcaa ttgtccaaat gtgggtagct tttcttccca ctgttgtcag ctgcttccaa    51480
ttagccccca tatacataat cccagtttgt gtctgtatca gtacaattct cccatgtcaa    51540
tgtgaatttt aagccacaga gggaaagggg acagagaata tgctttcatt cagctctcct    51600
cgtctcacac ctcttgccct gcatgcattt ctttgctctg attaaacgag cattttataa    51660
gccacatttg ctgtgtgaaa ggcaaagtct tccctcccac ggatgacggt ctccagggat    51720
gtgtgtgtgt gtgtgtgtgt gtgtgtgtgt gtgtgagaa gagagagaga gagagagaga    51780
ctgtaaacat atatctctgt gaaacttcat tttccatatg tgaattttg gaaccgagac    51840 aaatggaact tagctaaaag atgggaaagg tagactgact ctgacttaat ctacttaacc    51900
taccaggcaa tttataactt gatggcctaa ttttgcagc acccagaagc aagcctgttt    51960
cagcacggca aaggctcagc tgctaagtgg gcagcattgt tggaggtgag cagcttaggc    52020
tgactgttca tcaaaggacc aagcgcttga ggttcgctca tcgctggagg ccagagtggg    52080
gagggccatt taactgctca aggccatgga actctactgt cagtttcagg gaaatttggg    52140
accctggagc acaaaccaaa actccaatta accaggagag gaactcgatc cccaggagat    52200
aagtgaagag taagaagtct atctttagaa acaagagatg tccaaggcta gaaagatggg    52260
gaaggagggt ggaactgttc tggaagtggg tctcaatctc agcaccagca gctctcaaga    52320
ctttctagag aaggaaactt catttctgaa ttaaaattag tcttcaatga catggcaggg    52380
atttcggcac actctcttgc gtcataggcc actgtgttgg aggcaggagt gttggctttg    52440
gaggcataga gattaaaatt agagtaacac gtgagcactg aaaaggttaa acagtagaga    52500
catggaggac tcccgacccc catgtaccc tttcttaacc ctttaattaa gatcacagcc    52560
ctagaaatag cttgcaaaat aattaactac tgatcattta taccttagtg cttctgtgag    52620
catgttttct ctttcattgc tgctcatctg catggaaaaa tgtgcatggg tttctgaata    52680
taactccatg gtgcttgctt ccattatatt tgtgccattt ggatcataac tgataagcaa    52740
ccaaagagtc ccatattact gcacgttccc atcgctattt tatgtgaagg tggtcctggg    52800
```

```
ggctgttctg aattctcagt ttcctttttt cccctcccca gttctttgaa aatatcagaa    52860
acggacttgt ggcatctttg aaaagctact taaaatgtgc tgctgtgctc tgaacttgaa    52920
aatgtgcttt taatacaaag tttgtgcagc ccttgctgct catacgagat gaatcttacc    52980
atgtggtgga tgcccgtctc atgccaggca ctgtgctcta agcccattgg tttatttcag    53040
tgcttgaaat tggctttcga gagaggcacc acggttccct ttttacagga gaggaaacac    53100
cagaggatca gagatggaga gtctttctcc acaaactcac agaccccaaa ggcaagctca    53160
gggttgtcag cttccaaagt ctgcctgctc caggacctca tgttgcatct ccattctctt    53220
cactgagggt caaatggaaa gaacacatgg gggtcaagtt tcagaaaata agagaaatga    53280
agaaatatgt gcccggaagc aagaacgacc gacctcatta aactggctcc cttcacctcc    53340
tctcacatct ttttctgcct tttggccaag ttttctctcc cccgcatttc tccttgatc     53400
tcgtttgaat cctcttccct ggtgaagtca tttaggttca ggctcttatt ttactttggt    53460
ccataattta gatcgaacca catgtgctga tgtgattgaa acgatgtgga attctctgga    53520
cagagataga attatggagg ggttagtgtg tgtgtttaag attaaaagac caggtgtatg    53580
ggaggaaata taatgaacaa aaatagtat tttaaatgaa tactaaactt gcactcatgg      53640
aaaaagttct cttcccatga ggttctcgca aagcatttta ccatcagcac acgcagtttt    53700
tctcagtttt ctgagatggg gccatcttga atccaacaga caacacacag catcagccag    53760
actaacacaa aggacgtcat gggcatggac gtaaatactg gtgtcaacac taggtctgca    53820
cctcgagagg agtggagcaa aaggatggag tggcagatga aggtatgctg ttcagaaagg    53880
aggcagaaat gaaaggaaga ccatcagtgc gctccacagc ttgaggaccg tcctggaggg    53940
caaatgccag ctgctcactt ctgaaaagaa aaattccagt gaaatgagta cagtcattct    54000
taggattact cacttgatac tgtgtatgtc tcttcttggc ttctcatctc cacacaaaac    54060
cctcaggtgg taaaaatcta attaaaaaaa ttatataaag tcttgtagat ttattagcct    54120
gaacataata gatttttttt aagcacgtta agtcttccat ggactaaaag aaaacttgta    54180
aacctaagag aacctctatt tttgatatac aaaataatac atttccttaa actatgatct    54240
tgatactaga atttaattaa aaaaataccct gcagtttata tgcaaagtta tagattaatg    54300
cttaaaaata ggttgtatgt agtatccaca ggtcatgttt gactgtcaaa tagatgtaat    54360
tttaattcat aataattgtg tcgtgttctt ccccactaga agccaattat gcaagcttca    54420
ccattcacac atggaaaata atttaatgga gtactcattg caatttcact tatccagaat    54480
tggctgttgt tctcagagca gcttgtgttg ccttgttaag gagaatatgt tagtatccag    54540
acatccagaa aggatccttt actgtttcag agtccatttt ccccacttttt gaaatacaca    54600
cacaaacacc cattcatgca aaccaaacag agattgtaaa gtgattccac tgacatttat    54660
gcacttcttt tttctctttg gttcttcaaa ctctcagtca gtgcgcattt actcttaatt    54720
tagatacggt ttaaacctaa ttagaaacca gaagctcttg tatttccaca aaggattatg    54780
acagccccaa gaaaagatag tgaaaccatt atataacaag ataaaggctt cttaacaata    54840
caaggatgga ttttctcatt gatcttagcc ttctgaattt tagaaattgc catttcaaag    54900
tctaaaacaa aggaaaatca gggaataaaa gaatggtaag tagacacaaa cctactggct    54960
ccatcatttc tgttttagca aataacctgc cacatatacc aatagcccaa gagatgggca    55020
tgtccctgca tttcctggtc aaggtgacaa cactgcgtcc tcctggaaga ggtctgccac    55080
tcaccatacc acaaaccaaa tataataaaa tcagaaggca cactatagtg aattttttag    55140
aggcatgtat tgaaaagcat ctcaaaaagc attctcgaag cttccagaag tcaactcaag    55200
```

```
ttatctgaaa agtgacactt ttgatgattg ctcgcttaat actgggagag ccagatgaag    55260
attcctcccc acttcctcag atgtgcaact ctggaatttc ttagtgttac tggagattcc    55320
tgctgcattc tgggccttta atgcataaac actgagatgt tctaaggaaa ttactcccta    55380
gggaggagag gggtggacga ggagtaagct ttgctggtga ctcatgcgct gtgtggaaac    55440
tccctgcaca agtgagctgc gcagggtgag tctaaagggt taatgcactt tcaaaagcct    55500
ctaatttgtt attccagaag agtaatttac tcactagaag tatctgggtg gctactaaca    55560
catttgtgtc tttaaaaaga tcagttttat tttaagatta aaaatataaa gcaagagctg    55620
gaaagtcact aaaaactgac agccagtttc ccattttcaa gagtatttat taaaaggttc    55680
tggttgcaga aggaataaga aatggcttga gatcatgaca cagtgaatca tgttgtaaac    55740
atgttagcta tggctgtgaa ttcaaccagc gatgagttca agcgtcccca gaaggtgttg    55800
ggggaattag ggacatggct gtgtttcccc agagaaaagt ggccatttta ctttccctct    55860
tcactaacat gcttttgaca tgcatggcag agctgaaggc aaggggaagg ggacaacata    55920
gtaagtgact aagtggcttt tttttttttt ttttttgccaa gtgaagctga gtcatatggc    55980
ctctgtcatt ccaaaactat tctctacggc tgcattcctt tcgctcttgc cttcctttag    56040
aaccctggag aaggcctcct gaagcctggc cctattatgt atcctgacaa agataaactt    56100
ttccaaaaag ctgcatgttg tttctagcac agttttttcct cgcagtgact acgtgatgaa    56160
agtaccatgc agaggaggtg tctgactgag gcgttcgtgg tgtgtgacag agtcccctgc    56220
acaggacagc cgcactcccc tcttgcgtcc tttcctccca tgtttgcaaa gcctcttttcc    56280 ctgtcagcag ggggtgttct ggcagttgac atttctgaaa actacagcct acatttttaa    56340
aaaatccagt aagtgaaaac taaaaaatta ataccgtggt cataatagtg tggcatttga    56400
taactaatga ggcactgtcg tgccagctat tattttcaga catttacagt cctttttttaa    56460 atacaaagaa atatttggtg tgaaatgttc cccgggagct ggtgcaagca gaggcgacag    56520
ggcaagggag cttgggttgt agcctcgaat tcctccggcc agggctaccg tcagcctgcg    56580
gcacacaagt aaatcaaata taaaaccaaa atttctgtaa gcaaatcagt ttctaactca    56640
ctgtaacgaa ttatctttcg cacatcacag aggcatctct tttcactgtc gagtttggtt    56700
tgcttggtta caaaagggc agttcaaaag ctttggttgc tattgtgaaa gtcagctgaa    56760
ttccttccac cgtgctgggg tggggtgggg ttcacgcagg ttctcttttg tcaccagggg    56820
tgctgtggat tcacaagtaa gcaagaggct cctcaggtca agcctctggc tgctccctga    56880
ggtcagctgc ctagcttctc ctcctctgag atagacggga acaaagtctt tgatgtgtgc    56940
atttctcaag cttgacaatg atacagctac ataaaaaccc atgatttcat atagatattc    57000
caaaacgtaa aagtaaaccat tgcatccaca gagacatgga attacagaac tggatgctga    57060
gctggtcact tgggaggcag gcgtccttgc cattggttta tgcctcagcc ccaccatgca    57120
gtggctggcc aggtgaccta ggccagtcct gcatcctcgg ctcctcacct gcctggtggg    57180
acagtgacat ctctcctgca gcactgctgt cagggtgagg gaggtagggc gcagtttcag    57240
aaaaccattg ggctgcacct gcgtgagcac agctgcagga gcaaaagtca gaaaggtcag    57300
caaaggattt caggagcaaa ggtcagaaga aaccctcaag gtggttgtgt ctgcaggaaa    57360
gtgctgtcgt ctcctgcaat gctttcaaga ctattcagaa gcacagtgtg aagggagagc    57420
cggagcccat ggggaaatga ctccagagtg ttccacgtgt tggaaggcat ctgttggaaa    57480
acggacattc aagcaaatag ttgcctgcat agacaacgca gaatgactgg gaaagcccca    57540
```

```
acaagttacc tactggtaaa tgaggtgaga agcttaaagt gagaacccca ttgctgcctc    57600
tttttcactt taaaaacatt taagttttga attatggtaa aatacacgta agatttacta    57660
ctgtaaccat ttttaagtgt acggttcagt agtgttaagt atattcacat tgctaaggaa    57720
ccaatctgct acttttgttt attaattttt tcctgagggg aaatattttt aaattttaaa    57780
atatttaatt gacaaataaa aattgtgtat attcaaggtg tagaacatga tttcatatgc    57840
acgtacattg tatactcatt accacaatca aagaaattaa cacatccaac ccacccatag    57900
ttgccattgt gtgtgcgcgg atgtgcgtgt atgtgtgtgt atgtgtgcac gtgtgcgcct    57960
gtgtgtgtct gtgtgtctct gtgtatacgt gtgtgtacat gtgtgtacgt gtgtgttcct    58020
gtgtatgtgt gtctgcgcac gtgtgtatgc atgtatatgg gtatgtgtgt acgtgtgtac    58080
gtgtgtgtgc atgtgtgtat atgtgtgtct gtgggcacag gtgtgcctgt gtgtatgtgt    58140
atatgtgtat gtgtgtacat gtatgtacgc gtgtgcatac gtgtgtgtgt gtgcacaggt    58200
gtgtatgtgt gtgcctgtgt gtgtgtgtgc atgtgtggtg gggacactaa aaatctctca    58260 tcacctttt agtcaaaaga acagttgttt tggtttggct cttctgtttt aaaatatcag    58320
aacaataata atttcccaca gacaaaatcc tcaatcctca ccatccttct atttcctata    58380
ttcatcataa acttcatgct tgatgttgaa attgttttct gaaatagag aatacaaaga    58440 ggagatttta aaatgtcagt ggcagcccca cactccttt taatcttatt tcctgatatc    58500
ttgagtttac ttggacgtag agttttcctt gactatggtt atttctggta gtagcagctc    58560
cagattaggc aatggttttc ttcagagata gcttagagtg agccccagaa caaggtcaat    58620
gcgaagattg cttgtgtctg cgtgtccagg gcacagtgat cctcatcact agccgggggg    58680
ctccgtgagg atctgctcct ggtcgtttct gttctgtatc ttctctgcag cccttactga    58740
agccgttacc aactggcaca attcaattcc tactgtaccc atcatgcaca gatggctgaa    58800
gtattgagaa cgctccagtg accgggaggc aatagtctgt ccacatctaa gaacacactt    58860 ggaataaccct tagagaagag agagagagag agaatgcatg gttagtaggt tatcaaactc    58920
ctatgacttt tcacaggaaa agccctcatc cacaccaact ttaggaatgt gtagaaagaa    58980
gggtcaggga caggggtgag tggtgggcag agcagttgga gggcacaggg aaaaggcatc    59040
tggtcatgta tttggagtag gaggtcttgc tttactattg aattgcaggg acactttggg    59100
aacagtgttc acttcttttt gcaaccattt cttcagagaa aagtcatgat actcaagtct    59160
tcttacaaag cagtttgagg ctttgagtac cagactgatt acagagatga gtatgaagca    59220
ttattgtagt attttaagt gaaattcact aaatgcaaat aaacctagca aatgctctat    59280
ggttaatttt tttctaaaat tcagataatt aagacaattc attctcctga aactgctgtt    59340
catgtaaaaa ggaattttat cgaggtggcc cttgagtgcc aaacagcctg tcctcagctg    59400
caaaatgagt cgttgatgat cctccagcaa gggatacttt ttagctcgtg tggtgattgc    59460
tgcacacggg atatgtgcag caagtatctg ctgagctaat aataaacagc tcagacagaa    59520
aagacagtgg gcacaaggtc atgcttaaaa agacccctg ttctactgca tcccagctcc    59580
ccaccatggg gcctcacagg ccctggtgac caagcacatc agacctggtt cttgctcagt    59640
cctgggagcc acagaaccca gcacgtactt taccccaag accagactcc agcttggctt    59700
ttgtcctcct ctccaggatt ggtgacctcc taggtcgtga agctgtgatg agcaaagaca    59760
cactcctctc cattctccca acttcaggtc cctttgacag tgtcagcagg catttaaata    59820
gcagaccacc cacagcaggg ctggtagatg cagtgaactc aggaagatgc ctgcatagac    59880
tctagtgtta aagacagaat ccttacaagg aaccccata gttacctaac tgctgtctcc    59940
```

```
agtggtcata gaagtgtgat aacccactaa tcatcattct ctgtctctct gtctttctca   60000
tacacactta cacacacata cacacaacct tgttgcttaa ttttcagaga gtctactttc   60060
agaaaagcct tcaggaatac atcatgtaca aaactgagaa attacctgaa gtatctttaa   60120
atttagtaaa aagttgcatt gttttttgaa catcacactt gaaagtaca tgaatacaaa    60180 catacttagg aaaaaagct ttaattaatt taaaaggag aacaatgcta tatgctgtat     60240
cccacctttc tctgaatgtt acattttctc ccctatccca ggctgcatct aagaaaactc   60300
agagggaata tgctatctat cttttccgag caatgaaagc tctgggtttt ttccttgctt   60360
ttcagggcac aatacttctc tttcttcctg gttagacagg ataagttctg agtcccctgg   60420
tatcatcagc ttacttcttc tctgttaaat attcacaaaa aatcactaac tttcatgcct   60480
cagcaaacct ccactgccta aaatatagtg aggtcattca tcttcggaca aattgcccca   60540
actacggtgg gaaaagaacc aatgtgttgg actatttatc taattttttgt ttagttcggg  60600 gatacaaata aatgcataga tacatacaaa catgcgtaca taatagcagc agcagcctgt   60660
gaaacattga caagacctgg agttggaaga ggactttgcc atcctccagt ccaacagttg   60720
cctgtcacag attagacgac tgggatgtgc gcaggcgatt atttgcaaac ggccctgagt   60780
cccccagttt atgtcttaat tcgcagccag ggctgattgt agaagcaaat ttgcaaacat   60840
gtgcaagaag aaatcacaca tcctagagct tggatttcct cgtttcttgc tatttctatc   60900
cgtagacaga accattgctg agctgttaaa tttgtctcct tcccctatac cagtcttgaa   60960
aaaggaaagg aagtggagca agaaaaaga aattaataaa gccggcagat cctaggagaa   61020
tcttatttaa tccaagcttt gtaaagtttt gctttattcc atggcaacat gggtatacac   61080
atcccaccgg ctgtttcagt ggctcagagc aggtaaggcc tgtgccaaac gccgctagca   61140
ggaggaacaa cgtggagaca gccccagagg tggaacgttg gcccttctgt ggctccggtg   61200
tctcaggacc tccctaaagc ccagccctga cactgagcaa gtttccacca ctgttaggaa   61260
gaagtagaaa ggaatttgga gggttggtgt tactgttcaa gagctggaag gcttctgccc   61320
ccattcccat tccattaatt gcgtgaggta gagaactcat agaagatagg aacacatatg   61380
ctgatttcca aaattgcctt tgtatatttt cacgtgaaga ctttaggggc aaaagaaaag   61440
aagcaagcat tttgaatatg tgtttcaatt tgccttctgt tatataaaat tgtattttgc   61500
ctattctttt ttcattattc ggaaccttca agaaataaat taagttctct caaaaatgtg   61560 tttttgaaa agaggactaa aacagatggc ctggctgtgt taaacacagg gaccagacca    61620
gcacccacct ctccacctgc cctgccttca ctggcagaat tgtgatccat catgttctct   61680
gttcaatgtc atcatcccctt tcagagcatg ggtctcttcc tttctaggca gtcttaccag  61740
gatgcatggg tgtgcctgcg taggcacacg cacagctccc aaggactcta aaaaagata   61800 ttttctgct tatatactaa taatatgtta gagatttatg tttcaaatta gtacagaatc    61860
acatggttct ctccaaatta tatttgagag agaaagaata gaacaaaatt tattttacaa   61920
aaatactcag tacatttagg gcatatacaa agatgttcca gaatgtagct tatctcttta   61980
aagacaatta acacagtttc tgggcaaggc aaggcaaaat attcagtaac ttagcaacac   62040
caacagaaga cagccaatat tgcagcacat ttttctcttg gattgggtca gagagtactg   62100
cagagaaaat ggagtagaga gacctgaaat actttcgcac acactgtggt cagtgcagcg   62160
tccactgtgt gccacagtaa tactagaaac tccctggtta ggccttggaa tccagctctc   62220
atttcgtatg tgacctgcag ggaagtaagt taaatgcaca cgttttatca agttcaaatg   62280
```

```
caaacttaat tttaaatgta tgcaacatca gtttaagcgt tgtagctatt actagcaatt   62340
gtacctatta ctagtctgta ctctgcacaa ctttggagta tactgcctac tcaaggtgga   62400
ttttagagct ctatttgtgg cattatatca cggacaaaag cacgttcatc agagtcagag   62460
gaatgtggtg caaatcccag ctgtcccact taccagctgt gggacttgag taagctcctg   62520
aagcagctgc acctgcattt tctggtgggc accatggagc tgtcagcagt gctttcctca   62580
gagggctgcg ggctggatga ggtttgctgg tgcatgtgaa gtgtcaatca ttgctctcat   62640
gagtggtgat gctgatgccg ttcccttttt tagggaagtg attttccctt acaaagttac   62700
caacagtttc atgttggccc attttttctat taattgtttc cactaatagg accaacagtg   62760
gtagtcccat cattttatta ctgcttgtcg tagcacaagc agttgcttca ttgtgtttag   62820
ataaatattg acggctgctt ttaacagtct gctgttttgt ctccttttga ggtccttaaa   62880
gtaatcctta aaaagatagt gcagatggaa agatgtctgg agtcagtgaa cctgccttct   62940
ttcctgtgtg cttgtcagtt tctaaaatgc catacacaaa ggactttcat gatttctttt   63000
taggtacatg attacagttc aattcacttc actgtctgga aaatttcctt ataatcagga   63060
tgaaatttct catgttagcc tttcacattt cactactttt agataaggaa ttctcaggct   63120
ttgctatatc tgactgctct tggaggctga gcttttggct aactacctga ctactttgtc   63180
gtttctcttc ccttggaatg aagcaaatat ctaacttctc actcattgtt tctgctattt   63240
taccatttag tcatctgtga ttttttctaaa tactgaaaga cttccctcaa ttcaaactat   63300
gtgccggatc aaggaaaggg cagttggata ttgcagacag catagtgcaa ttgtgaagag   63360
tgtctgctta ccagccacgc tgccttgcac aagttatcaa gcctctcaac ccacttcctc   63420
aatctgtaaa ataggtatga gtgtaggacc ttcccagggg attttttttgt gactatagaa   63480 tgattctcag aagactttca ggcagtatgt gggtgaggca catgctggaa aggcttctgc   63540
aggtgcagtg atcaatgctt ttctcagtgt gtacatccca taatacagac acgttaccag   63600
aaactcccta gccaggactt tgattgcagc tcacattttg tatatggccc atagggaaat   63660
gaagtgtgta tttttttataa agttcaagtg ttaacttaat ttggaattta ctatcaaatc   63720
tcagttgtta tgggcatttta tagctattaa tacttcgtcc catgtgtccc atgaggaaac   63780
caaggaacag aaattaaagt tctttctgga gtcccctgaa tctcgttcct gttcttttgc   63840
accctgttaa ttacatagag acattcacag ctcttctgac cttatcagcg ttaaggaaaa   63900
cagaaaacca gcgtgctatt tgttctgtcc cttagtcaag ccttctcaac atatattttt   63960
cttccaagat tttgcatgtg cacagggatg cctatcctct acaagaaaca cattttaggc   64020
aaattataat taaaatgctg tttacatctc ttcaccttta gaatttaaag aatgatcatt   64080
tcttagattg catctcagac acacccttcc cctagtctgg agagggcgag gcccatgggt   64140
actgcaaaca gcctgacgtt gtcaggggcg gtctcaacgg ctcattcacc acatctgcct   64200
cgcgaaggct aagccatgtg ctgttacccc tgctgcgctc tggctcattc taaggtacac   64260
gctattaacc ttgtgagaaa acaaagaggc cagcccacc cttcctgctc actctgagtc   64320
acggtgaaaa tgtttcagga tctcgggttc gaccatgagt cctgtccagg tccaggagga   64380
aattcggaag gaccacatgt tcactctgag atcccacttt catttccctc ctggttgagc   64440
agcattaata ctctggctag atttaaattc tggctttctc cagttagaac tgaaagttat   64500
gacaatgtaa tcaaaataga atgtgggttt acagctggcc ccctggcctg gtttgtgaac   64560
ataaaacaga aacagaaagt gtaagtggtg acatcatatt ctctcattca atgtgaaagg   64620
ccaccgaagt cttttccagaa ttattttgga gaataatatg aattttttaaa aaatacctaa   64680
```

```
ttattttaaa tatcgtcttg cttgctcccc aaatacctac tgttttcaac ttggatatac   64740
gacatgatta aagaatatct aatatttggg aatgcatact ttaaccttat aaactaccac   64800
tgtaaataga cagactcatt aaagtgaaag gacatttaa atcaattagt aagcaaatca    64860
attaggtggc aaagacaaga ttattttcc ttatggtagt tgaagaataa tgcttaacct    64920
gtcattctaa ttaccaagca cggtgttctc tttggaagat catttcaaca aaacattatt   64980
ttcatccaga atttgaacct tgagattgca tggtatttta gaaatctatt ttagaaatct   65040
ttggcaaagg ttactattaa aacaatcaca ttcatggaaa atcagtataa gagcaactaa   65100
aataactcac aataccagta aaatcacttt gtcatcttct taagactttt aaagagcatt   65160
tgtaagtaac tgaatagaag gccaaagggt gtgtaggtag cccagaccat cagtgggcag   65220
ccagggccag ggcaggggcc acggttgcag cctgcattct tctaaagggc agagcaaatt   65280
aaagttgaag caggagctaa aaaaaaaaaa aaaaatgttt caagaattc caccaaccag    65340 aggatactac ctaggacagt ttgggcctaa cttatctgtg aaggcctcca gcttcctcca   65400
caccggtggc cacttttcat tcactctgaa cccttctttg tatggaggtc attttattaa   65460
ttgagctgtg accaacatga cagaatttcc tgttttaggg cttttataat atagatagtt   65520
tatatctaat ttcagaatat attcactggg gaatggactt agcaaccact accacaacaa   65580
tgcaacaatg tgttttggaa caaatttacc aatctgaatt tcccctaga ttaggtcaca    65640 ggaacattgc agctgatgta cagctatgtt cctcctgaaa cttggagaca catcctcttg   65700
agctgggtta taatgggcca cccaaagctc gagttcctgt aatggataca ctcaggcagc   65760
agaacctacc accgtagtga ggacagcacc cagagccctc agaggccatc acaagtgcac   65820
cacagctgcc ttctctggca cgctcagagc tacacagtgt actctgggat tggaactctt   65880
tatttttttt tcagttgatt tgtaaataag attgcacaaa aatccatgca catcaactct   65940
ccaaatcaga atttgctgag ctaaaaagag cattaaatta gatgggctgg ctttcaaggg   66000
gtgggggtgc aatagtggaa ctctgcacaa cagttcttta caaagagaca agcaagcaca   66060
tcgcgtggaa atttccattc aactggaaat gtccaagcct gtttacctca attaattgtc   66120
cttgttcact tgtccagcct agcaattgtc cattagtaat ttgttataaa tgagacattt   66180
ggtattaaag catctctttg ggatactggt atggtttatt ataacattct gttagtagtg   66240
ttgtacaagc ttgagatgta ttaatacgaa atccaagctg catgagggct ttattttca    66300 agcctacacc ttgctgaaat tctgaattaa aatatgattc tcagtacaaa tgaataaatc   66360
aacagaaatg gtaacgcatg tcaaatattc ttaaaaccca agaaagcctt gtaacttcct   66420
tcaatctaat gggaaatgca ggcaaataca agactgatgt ccttgagttt tattatcaag   66480
actcaagggc accagtaaaa tctagtttca ttggttggaa aaaaaatcct gataagcact   66540
gttaggcata ttaactttaa tgattacaat ttttaggaca ctctgtggcc tagacttaga   66600
aacacaacta atgtccagaa aaagattcct ctttttattc catcatctga taggcctatt   66660
tttacacata cacaccaacc aaaagtagcc aagcaaacaa aacaacatac tcacacccct   66720
tcgcctatta tcatctaggt gattttcaat gctcattgca atgaaaccta cttattgtgc   66780
atggcaccca cccccactga ggaatactgt agtttctttc cctttgaact tcattagtag   66840
agcacatggt tcattcactc ctgaagagtt cttcgtatgt cagaatatat atactacaac   66900
ataatttcca tcgagctct gaccacccgc ttatctatt tcataatgcc tgccactcca     66960
tcattagctg ttgtcatgta ggctatcaat aaatatatga caaataaaac agttagggaa   67020
```

```
tgagggaaat tgactagcag ccaaagacct aagccatcct ctgcttggac attagaaaac    67080
tgagttcact acagtcataa gatacacaaa ggcagaatgt aagccataca aaaatccatg    67140
tcaatcccaa tatgtgagta caactattga acaccatgta ctaatggatg agttggtaaa    67200
tcattcaatg tcttcatgag gtcaattaca gattattatt tagaccccaa agattccaaa    67260
gatggtattt cggtcagatc ttcatccttt gtaagcctag cagaaaatat ggcagtttta    67320
ttgactacta ttctttgctg ggtgtggtat ttttaaactg agacatcagt gtgcctagca    67380
cagggcctca agcacacaga aaaattcctt gataataatt aaataaaatt tcagcaaaaa    67440
atatcatctt aaggctgtga aattatcttc ctgtgtggct aaaatagtga ataaaattca    67500
gcgcaatata aatcatagta caatttcatc actaaatttt ctgatcttga tcttgtcatt    67560
ttacattgga agtaaaaatg tgtcctcctt tttttctctg acagtgaaaa gtgtgtgtgt    67620
gttgtgtgcc cttttgcaca ccctgcctca cacttgctgg tctaattcct tccagcatga    67680
ttatgatata attaaatgac agaaatgttt acttccaagt ggaactaagc cagggtaact    67740
cagggtaggg cagctgcttg caccgaaaga ccaagactgc tagagaacta ggaaacaggc    67800
ggtgcaagaa ctccaggctc tcatggaaga gcgggaggct tctatggggc tgcagaaact    67860 cttggtgct tggggaaaaa atgggttaaa tgctcttaaa aaagaaacct gggagaggta    67920
gtttccagat gcaggcccgt cttttctttt aaacagaggc agctccgaag agctggacat    67980
tgaaccctga gcaggaactg gaggccgtca gcgcagcttt gtttggcgag cggagctttg    68040
caagggtgta atgctgcacc agggagacgc tatctgcagg gaccggtgac gccgtgggtg    68100
tggaggggga ggcagtggct ggccctcttg gggtaaggta cgcccaggaa cagtttagaa    68160
taacgtgcgc gagtcaaagg gaagaagaag ctcctgcaga ccttctgggc actgtgcagg    68220
gtttgctcct gtccaccgtg ccgtgttcct gtcctgggga ttttgggtgt gtggcgtgtg    68280
gggaggggag aaggagcaag gcggcaggga ggggatgagg accaccctgt ccatgggaca    68340
ggccctgggc cccgcacaca ccccaagccc cgcgtcccgc gtcctcactg tcctgggaca    68400
ccccccaccc caccccaccg ccacagccca gagcggtgcc aggaagccgc ctcgacgcag    68460
ccgtatcttg aggctccagc cccatcccca gggtaccacg ccacgtagag acactatttt    68520
tcacttcgtg tttgtcactc ctaaagcatg tgtgctagct gcaccaaccc tgggatgcct    68580
cggtgcatag ggtttatgtg cgtcctcctc cttccctctg agctggtccc ccgtggggaa    68640
ctgctgccca gactgacctg cgtccttccg cacgtgcagg aaaatgtcca cgtgcacttg    68700
tcagggtggg ggccacacgg gcaccaccac tgatcatctg tgggatcgag ttactgccca    68760
tgcagatccc acgtgcaggg cccagtcgct ttggtgagag agtggacgct gtggtgactc    68820
cacggtctgt ggctgtgctc aggaggacag agagggaca tcctgagatg gtttgggcag    68880
cccgcggatc ctgtgcatgt ccccagagcg tccactttct ccatggagca gtggagtggc    68940
gttgctgaga cagaaagttc aggttctcca ctccccatgc agcccccact ccctgtctc     69000 cggccaggca cgcgtctggg gtggagactc ccggtgcccg ggccctcca gacctctttc    69060 cccacccccag ggagcaggcg ggtacttcta ttccgtttgg cttcagaagg gaaaagagaa    69120
cgtaagttca gggagttctc gtccattcct ctcccgtggg ccgggcaggc agcagggaca    69180
gccttcagga gccaggaggg gctcgagctg cgaggccctg gaatgaggca ggcatgggct    69240
gaggctggag gggaaagcccc gctaaggctg gcggggggcg ggaaaactta ccaccagggg    69300
actcgagatg gggaaggaaa ggtcagaaga ggagaggcca ggcacggggt gtgggcggcc    69360
tgcagagctg gagcaggtgc tccgcccaga gccaggcatg cacactcaga gtaggtggcc    69420
```

```
tgtgcagcgg ggaagagggg cgggtcggcg tgctgctgaa gatgcaggag ctgcggcctg    69480
ctctgtgcgt gctgaaggtg tggtgagaag cacttacaaa aagaaatgga ctgtgttagg    69540
attgcacatt ttactttgtt tctcccaaat acgtgttctt tgaatttttt tccttccagg    69600
gccaggactg gagtgatggt tgagacaggc acgcactggg tcttgtctgc atttacattt    69660
tgagattttg ttcagcatgg attttatggc gttttttgt ttgtttgttt gttcgttttc     69720
aaaatactgc acggtttatc gtgaagacag ggtcctttgc tgccgtctta agttttgggc    69780
ccaagaacgt gccccaccct aggcccgggc ctgctggctt catagctctc atcattccca    69840
cggaacctta agacctgagg acagaaagga aggaaacaag cccagtagtc cgtgaaaatc    69900
cagggtcccg ccactccagg tgtctgcagc agagctgaac acacgtaggc tcttgccagg    69960
aggggcattt gtatgtgctg agcattcctt atattctcaa tatgacgcct ttgaaagatc    70020
tgtggtttgc aaatatttac tctcagtcca taacttatct ttccaacctc ttaccaggct    70080
cttttgctga ataaaagttt taaattttga agtctaatat attttttaatt tttttatttt   70140 atggatcata cttttttgtgt caggtttgag aagtctgcac caaagtatgt cctgtggttt   70200
tcccttaggt catcttcaac aagtttcata gtatttttgtt tagatgtaaa tctgtggccc   70260
attttgagtt agttttttgca caagagttga ggtcaaggtt cttttttttgc ctgtgatgtt   70320 cagtggctct ggcaccattt gttgaaaaca tgatagccaa tgtcaagact taatagttat    70380
aataatcagg agcttttgtt tctttttgtt ttgtttttag taactgccag tcactgcttg    70440
tggtatacat acacaatgga atactattca gtcttaaaaa aaaaaaaga aggaaatcct     70500 gtcatttgca tacctggagg acattatgtt aagtgaaata agccaggcac caaaagaaaa    70560
acattgcatg atctcactcc ttcatggaat ctaaaaaatt gtattcagag aagcagagag    70620
tggaatggtg gttaccaggg gctgggaagg tgtgagcttg gggagatttg gtgaaaggac    70680
atagaatctc agttagacag gaggaataag ttaaagagat ctattgcaca tcatggtaac    70740
tgtagttagt gacaatgtat tgtatacatg aaaattgcta agagagtaga ttttaagtgt    70800
tctcaccaca ccaaaaaaag gtatgtgcag taatacagtc attaattagc ttgatgtagc    70860
cattccacaa tggatacata tatcaaaaca tcatgttgta taccataaat atatactgtc    70920
tctttatgta aatttaaaaa taagataaaa taaatgttat tcacttgtcg tggatgtggt    70980
ggggacaggt gtgggatagc cctccctgta caactaggac ccaggggtga tctagtgaca    71040
ctagccattt atcaggacgt atgggtgcca gtcaggatga taaagcttcc ttttggccac    71100
tatactactt agaaatgccc tgcaaaaggt gcacatcaaa gattgaaagc tcaatcctgg    71160
attttaagtg cttcaaaagt gcacttaatt gccacatttt tgtcaaacat tttcccaggt    71220 agtattttc ctcatgtaaa acaacagcaa tttaatttga acagaaagca ttttgaaaca     71280 tactttggc agggttcctt gcagatcaga atggaaatga ttaacagggc aattatcaat     71340
catggacttt tggcggcaga aggaactgta ttgtttggta cagtctgggc cagggccaca    71400
caccgtaacg gagatactct attctgtgga cggttggagg gggctgtgct gagcagggta    71460
actgcatctt ttcctagact gttcacactg ctgccacgaa ggagtcttgt ttagactgga    71520
cctggctttc ttcttcgcaa tgagtgttgc agactcccga caaaggccag gtggtaaagt    71580
gtggtgtctg tgagcgagag cctgagatgc ctgagctgac ctgtcctcag ccacctgcca    71640
tcgtgcagag gtgagagcag cccctgaatt ctgcccctcg gtctctccat agctaaagca    71700
aaaccatcct tccgtgctcc caggacaagc aggctattac caaatcaccc actaaccctg    71760
```

```
ggcgaggagg ggccatcact gcacaattca tcagtgtctg tgacaggaag agattgtttt    71820
agactggttt ttttttttt atttgcaagc ttttttctct ctccaaaacg tgctgtcagt    71880
gtgttctaat ttactctgta aggaattctg gagctaatca taggctcaca aaaagcagca    71940
caggaaagtt tcccagataa catctatttc agtggctttc aaacatttt gaccttacca    72000 aagtaagaaa tacattttaa tatcatggca cacatacagc tgtatctaaa ctttcataat    72060
actgccttta cgatatcact ctgatattgt ctattctttt ctgtttattt ttcttttgt    72120 tccttgttat gctggttgtg acccactcca gtgatttcac aatgcaggct gggtggtgtc    72180
ccacagtttg aaatcccaat ctagggcctt cctctcactg tacaaagtag gtaactgggg    72240
acattagtgg atcagtgatc aaaccaaagt tatttgatct taccaagtga tatcaggatg    72300
agaaagctgt tagagtgtca gatatgtgaa ggaacttggg tcattcctga tacctcaaag    72360
agaaaaaagg tagtccttga acacctccta cttgtaaagg atgcacaatc ctacatgccc    72420 ctcccttttcc tttcctcccc tctgtacccc acccctgccc acattttctt cataagcagc    72480
tttggtgttt tggcttgttt gtttcccttg tctcctacct gtgactttat agccttttgg    72540
agactcacag caatagttgt atttaaactc agtgggtggc atccaaggct aaaaaggaga    72600
ttgcctagac acaaaaccac ccaagggaga aagcaggaca gcatcttact atgattgttt    72660
cttgtttctt cctgtctcat aaggattatt acccagggtt ttcattttt tcatttcatg    72720 gttcattttc gctccagtgt agacatacaa tagaccactc gtccctgtgg ctccgggcag    72780
cagcctcatc tgagaccctc ctgagacatc tcgtgcaggg cagccgtagt gtgtggcttc    72840
cccagggctg ctctaacaga tcaccatcct tgccatggct taagaagctg cagatttatt    72900
tgcttacagc tctggaagcc agaagtccaa aatcaaggtg tcagtagagt ctctctctct    72960
gaaacctgct gaggatgatg cccctggcct ctccccagcc tctggtgttc ccagcagccc    73020
ttggcattcc ttgccttgta gatgcaaaac tccgatctcc acctctatcc tcacagtgag    73080
ttctcctgca tgtctgtctc tgtgccttca cattcctctc tgtgtgtctg tgtttccatc    73140
tccttatgag gacacccatc actgaatcag ggcccactct ataccagtaa gacctcatt     73200 caactccatt acatcttcaa aaaccccatt ctcaaataag gttacttcac aagtgctgga    73260
ggttaggact tgaacatacc ttattgaaca atccaactga tgacacatag taatttatgc    73320
actcgttctt ggagacgttg actttattta gtagcattaa ccatggcaat gtcaccagca    73380
tcgctgacag cctgaagcat atgatctcca gaatgtattt caatcatcat gttcacttcc    73440
ttggtattct ttagacaata actcagcctt gaactccagt aaagggtttc cctgggattt    73500
tcttcttgac tcactccact gtggcctccc tcatccagga ctgtaacaga cgcctgacgt    73560
cagtggtcta gacctctctg ctgaatgtca tctttggtga atgtcttatg agaaaacaca    73620
tggttggtca ctcttagaag ggcatgaaag cctgtctgca gtataaccaa aacaggcaca    73680
tggcgaggca cactgtgcgc atgtgtgtac aattaatatc atggttttaa attattttca    73740
ggccaagggg agatctttgc tgcatctact gaagaaagcg aatctttttc ttcctgaaaa    73800
aaaatggcta cttattagtc gaatttgtgt tttaaaaata tgtgaactaa tataatgcag    73860
acatgcatta atgtttaaat atactggaag ttttggtaa aatgaaaccc attgtctctg    73920
ttgattactt tgatgagtca agaagtaaca tcctgggaat gattggccag tttaaatgag    73980
tgcctcaggt ttttggaata caagaaatca agaggaaggg attagaacat ataggttagc    74040
aagattggga tcctaaaata cagacccaaa tgaatgaac aaaatcaggg aatttattaa    74100
taacagggtc aaggccaaat cagtaacaaa tatcctgagt ggaagaaagg tggtttaaca    74160
```

```
aatgcccta tgaaagatag agattggctt accatgatga gatgtaagcc caagttatga    74220
ggttggcaca caaaaccaca aatgtcatag cttaaaacaa cacacacttc ttatctctgt    74280
ttctgtgggt cagggtctgg gttctcaggg actcacaaag tatgttttca tctggagctc    74340
caggtcctct tccaggctca taagggttct tggcagaatt cagtttcttg aggctgtagg    74400
actgaggtcc tggctcctag aggccaccct ctccataagc agttcttagc atggccgcct    74460
gcttctccag gcccagtggg aaagcatgtg cctccaggag ggctcagtcc attcttcatg    74520
gcttttacct ggttaagtca ggcccactca ggataacttc attttgtatt aaatcaaaac    74580
cagctgattt gggatgttaa ttacatctgc acaacttcaa ctttgccata taacctaacc    74640
atgggactga tatttatcat gcatttgggt caagttgcat taagagatat aataaagctg    74700
gacaagcttc tgttgattag aagagttcag ttacaaggct acacttggga ggaatgttta    74760
caaactggaa tggtcagagg atggggaaga cacttgagaa aagtcaagtg acggatgaag    74820
gcaaatgtgg atatttatct gggagaaaac taagaggagt tataatagct gtcttcaaat    74880
atttaagggg cttttattag gaagaggaat ttggcatatt ggattttgcc ttcagagaag    74940
tggagtcctg agatgctctt agccattcat tccagcctcc agggctcacc tgctgtcttc    75000
tgtccaggtt ctcggtagca gggcagtaca gccccatccg tgatcttcca tagtcaggca    75060
tattgtcaca ctcagtgagc ggagagtcaa ccgggaggaa ggcacagttt ctctggaatg    75120
acctacggaa tggtacgctc aaatgcaaat tctccttccc ttccccagtc cttgtccttc    75180
agatggtaat ttaggagctg aaggtcaggg caccagcagc cttggaagc ctacaggaca    75240 acagtcagcc tggctagaaa aaaaaacaat gtcacaggca tgttgtgttt aatcacatga    75300
aggatatttg cattgttttc caactgatgc cagcagacac attgtcagtg gtatcatgcc    75360
tggggtatca gagttgacat tgggttgccc cttctctgag gcattcatgt aaatcctttt    75420
aagtttataa aacctccatg tggctcctgc atgcttcatc atttgcatgt gtctcttttt    75480
ccaggggagg cagcatgggg agcaggatgc tggtgggctc caggtgcaga gagcagggtg    75540
ggcgtcagac cccaggtcca ctgtgcacgc cctcttgtag agcccgttcc gttgtccatg    75600
agatgaggag tgttcttatc tctaaagtat tatcatgaaa acctaacaat gtagaaagac    75660
taaagcacat gggtggtgct tcataaatag tatttctccc actttctgaa aactcctgct    75720
gaagtaactg cacaagaatc cttgaacatt tagaattctg ttttagcca taccataaag    75780 tcagtagtgc gtggtggaat tctgctaacg aaaattgcga aggatcaagg cagagtacag    75840
agctggtgtg tagcgggtac cttctgtctg ctggcactag gtattttaca cattaaatca    75900
gctcgttctc acatcagctc ttttaaaaat aaggaaatga ggagccacag tggcccaact    75960
gatgcagtgg cagaagtaga atttgagctt gtgcagatgt gcctccgtgt tttgtctcct    76020
gagcatgctg ccccaagttt gacaatacca agatttgtac tggaacattc cctcccatcc    76080 ccaccccta gaagcccctc ttcctccctt agatttgaca catagtttga aaccactatt    76140 aactaccta tgagagccac tgtttgtgaa gtgctgacta tgtgccaggt cccgtgccgt    76200 gcaattttg tgaattatct cgtgtctaca gtgcctcaca atttctctgc tcaataccatc   76260 catgttactg ccgaggaaag ggaagctcag agagagtaag taatttgctc gagttaaaga    76320
gctggccagg acagccaggg gcttgcaccc cggagccttc atccactaca ctgtcagctg    76380
gtatctcaac cagccattac aggctgtaaa aaaattatat aagatagtct atggtaatgc    76440
agaaaagtga ggttatttg ctcccttcc ctttgaagaa aaaagccctg gaaagacata    76500
```

```
tcacttgagt atgggaaaaa atgaagctgt ggcttttctg tgagtcaatt ctttcctggc   76560
agcttcttgg aataagacca agtatagcag cagagttttc tgttttaatt tgagctgcag   76620
ggtgactttt tttcttctat gctttcatct ctctgtggct tcttttgcct cgttaatttc   76680
atgccctgcc caggcgggct actgtgctgc ccagtcaccc gggtctgggg cggccaccgc   76740
tggccagcag gcaggccctc cagaggcaga ggtggccacg cttaggtcgc tcccgctgtg   76800
gaggcggcac acttgggtgg cagcacagct gtgatgtggc ggcagctggc agccccatgg   76860
gaaagatgtg tgaagtgtgg ggtttgacga cccatgggag aacagacttt cttcctcttc   76920
ttgttttccc ttcaaagccg tgagtcaacc tcaaattctc tgtctttttt ctccaccccc   76980
tcgtgcctct ctccctcacg ctctgcatct tcattgcaa gcttgcattt ttttgcacac    77040
aacactatct taatatttct cttttctgca ggcaggaaat gagaagtcat ttttcagggt   77100
cattcaggaa gtcatccaga gttataatgg cccattatct actggtcaga gtttacttag   77160
gctttcacta cttccactgc ccacttgaaa cagggaaaaa tattttcccc ccgcgctgtg   77220
agtgtgctat ttagagctga ccacaagcgg ggggaagaga ggatggctcg gatgctgcat   77280
ttccactgag aacacaaggc tggcaaagct tgtctgctgc ccagcaagca cttcaggctc   77340
acaccatttt aggttcactt taagtagttt ctcaattgtt aaaaaaaaaa caaaaaaaaa   77400
aaaacctgta ctctgaggat atgcttataa tcccatagct aacccagaat tcttagaga   77460 actgatcaac atcagcagtg cacttactg aaaatgcaca ttctcaggcc ctgcgtaggg    77520
cctactgagt tagaatatta gagagcaggt ctcagaaaca ttctatccgg cagtcttatt   77580
ctatgcaccc gaagggataa gagccatgct ttcatgaaac atgggttgtg tgtaaaatgt   77640 ttaaaggta tggcaaaatg tgtttgattg gcaccaagga tttctggttc ctcctagaat    77700
cattaatcaa actttgaagg agaaataaga gagtcggcat tttcttgcac attctttgtg   77760
atgttgtgat gagttggaaa cttcccgatt gggtttatta gagcatgaac acccaggcac   77820
ccagcttcta gccagccctg tcaggcagag tctcctcgaa gatgtggaaa ggactgacca   77880
acagctgagg cctacaggaa cctgagcagg caaggggaga ggcaccccgg aaccaggagc   77940
aatggccttc ccaccctccc tcgtcctctc ctcttctcct tttggagttg caggccacag   78000
aaaggaagtg acatgagtca ctttgggcct tcttaattcc ttcatcaaag gcagcacagg   78060
tgtgtatgtg tgttggtggc taattgaggt aggcccacag aggagataac agatggacat   78120
actatttcct ttcttccatt ctgatataat tcagggtata aacacacaca cacacacaca   78180
cacacattct cacttctttg gcatctacca cacctgcccc agtgcccatt tctctcccac   78240
ctgaataaaa agcccccaca aagcctgagg tacatggaaa ggagcagtgg tctggctccc   78300
aggagtgtga gaagcagcca tgttttcaga ggctgtattc cacttggact tggccctacg   78360
ctgaaggtag gagcggatgg gggaggcccc cttcgcacaa agagccccat gaaagagtgc   78420
acagtccagt ctataaaaca gacgcagaaa atgtgtgtag gacttcttcc tgaaaaagag   78480 cgtggtcgt ccagtacctc catgttcatg gaacttccca gtctgcagtt taccctttg     78540 tgcaactccc ttttggtaaa gccctggtca cacttctggt tgttcagatt atacagggat   78600
aattccagag tgattttaaa gtcaactgcc aggcatccgc acttgcaaat tagatgcctg   78660
gcacatgctt gtgttaaggt aataattcat tacaatacaa attacagggg agttcctctg   78720
ggcatgcgac ctttcccgtc atttggcttt ccctgtgatt atcaggggag cttccatcgt   78780
gctgctaatg ggaccttaac catgtgtcaa cccatggctg taatgctgac actgttttct   78840
ttctggaatg aaaggccttc gcaattgaaa ccaaaatgtt atccaactca gtcctgtccc   78900
```

```
tttgacgatg aaaacatcaa gttctggaga ctggccatcc agcctccctg cctcatctcc   78960
cacgccctcc atcatttttt gtctctactt acttatttat ttggctgtat tttacgtaca   79020
tcatgcaaaa atattcctct ttgtaaaaag tataatgatt tcaggaaatt agagggtaaa   79080
aagcaagaac catgctttca ctccactgtc aagagttgtg gaagaatcct tccagcattt   79140
tttctgtgta ttttacatac atacaaatat atgtacaaat aaaggtcgat catttaggtt   79200
ttgtttatat ttttgtatat atgagcttat gtcattcata catattgttt tgcctcttgc   79260
ttttttttaa cttaatttta ctttgcttga gagcttttg  aactgaagta cgtgtaagtc   79320
agcctatgca tgtaatggct ccctcatctt ctgtgaggct gtcactaaaa aggggattta   79380
gcttgttctg ggctttgcag cccgtacact gggcactgtt catacgtact tctctgtgca   79440
cgcaaaggag ggcttgctag ggaggcctgg cagagggtgc cattcaaata ggattttcaa   79500
tggaggaatt tttaaatttt cagttatttg aataagtttt aatatatatc cagaacccca   79560
aatcatcaag tttgttttct tccacatctg tccttccatt tctgaactat tttaaggcca   79620
gtcatgtctc atccaagaaa tcccatcctt tcacacaaca ctatctccgt ttcatggtta   79680
tgaatctcta aaagcatgat ttttaaaaca taatcacaat gctgtcatcg aacttaaaaa   79740
ttagccataa atctcttatg ttacccaaca accagcctac tgacacatct ccagttgtct   79800
caaaaatgtg ttttccattg tggtttgtct gaaacatgat ccaaaagtca gacccacctc   79860
tcacctttcc ctaacctgcc ggagcccatg tttctttcca gccaggcttg gagaccacca   79920
cacgggattt gcttcttggg gcctccctct aaccagctat gcaggatgcc ctctttcctg   79980
tcaatacaag ctgctcaaag gactcattca gttcaaattc acctatgtga gcctaggtga   80040
tgctacttat ttatttattt atttatttat ttatttattt atttatttat tttgagatgg   80100
agtctcactc tgttgcccag gctggagttc agtggcataa tctgggctca ctgcaagctc   80160
tgcctcccgg gttcaagtga ttctcctgcc tcagcctcct cagtagctga gattacaggc   80220
acgtgccacc acgcccagct aattttttata gttttagtag agacagggtt tcaccatgtt   80280
ggtcaggttg gtctcaaact cctgacctcg tgatccaccc acctcggctt cccaaagtgc   80340
ttcatgtttt caggagctgt acgtgcattt ttagttttga tgaccaggtc cttttctgt    80400 tttttaaaga acttcaaatg atctccaggg tacacagcgc ttgtgtgctg atgaaaaagc   80460
tggcagtaca aaggccacca gccaaggtca cacagccaaa aagcccctga cctcgggccc   80520
cttcccagac cctgggtctt ttgctgccac atgaatcttc ttcaaggtcc tatgtgtaga   80580
ttttcttgac ttggccatat tatttaggat tcagatataa taacaaaata gatgttaaag   80640
cataacatga aggcatttaa aagggtagaa agcacatgat ttactaaaac cataaatctt   80700
atgacctgaa agtttcacct aatctcttaa aaaataccgt actaaaccct gattgaaaat   80760
cagagctcag acatacagcc tgagatgcca aaaatggcc  aggcttgtct gttgagaaag   80820
ccatatgtaa ctaactgttt ggaaattcaa aatatatctt atcattttaa aaacatcttt   80880
cttctaaaga caatcatctt ggcttcagga atgaggctag taaaaagtga aatactccta   80940
cttgtggaag aaatcctcat tttaaccatg aagaactgaa aaatgcattc tgatgttgat   81000
ggacccaacc tatatttggg tatttttatga tgtacacaat atacttttgt atatgagatt   81060
gttattaaat gtgactttgc tttttcaaga catacaatgt tcctccgggg gtcaggcact   81120
gtgtttagca ctttgtcctg acctcatctg acttctcagc tgtccctgag aggtaccagt   81180
gtgcaagatc gctgagttgg caagtgatag tgacaatatt ttcaccccaa tttctaattt   81240
```

```
aaagaccccg atttctagtt ttgttttgta ttggatttgc acaatttcac gttctgaaag   81300
aggatgccct caactttgca aaatgggcct tttgaatgaa aaggatcagt catgtcagga   81360
aaagcgctac aatgatgaaa tatgataaat aagtcagtct ttcatctgta attatctact   81420
atggggtaaa aagtgatgaa aactaccatc ttgaaaggtt ctggtgatag tggttcctaa   81480
tgcagtgaaa gatgtgtaag tcaaagattt gtaaccagcc agggaatgag aggcgaagcc   81540
atagctggtg gcgggggcca catctgggtg tggggaggcc acagttgggt tggggtgggg   81600
gcctgcagtt atccacaccc ctcccacctc ccttcgacag tacaggcttc ctggttacct   81660
tccagagagt aaggccaggg agagttgaat aagttgagaa atgtcatgtc gaagctattg   81720
gtggaaagag ttccattaat tgacaataca agtccctact acattctaaa atctggtcct   81780
gactagtggc aagccgggcc caggagtagc acttaaacaa tggcaggctt gtgttgctgg   81840
caggatactt cagcctcaga ggagctgtgt gcagctgggg agactcacac tcagaggatt   81900
tcaaagcaga gggcatctcg tagagcaact tatccaaacc ctgacccact gtaaacacac   81960
acacacacac acacacacac acacacacac acacacaccc tgagagagag aaagagagag   82020
agataactaa agagagagaa ctaaagtttg gcaaaataat acatgctcta atgaaggttt   82080
attaatgatt aatctactcc tagcatttcc tagtccactc tatctcctta aaaaaaaatt   82140
ctggttgcag cccactaact tgattgtaca gctgcttaat ggatagcagg ctgtaatttt   82200
cagagaactg tttaatgcgg gctacctctg ttcttccatg ctgcttgtgg ttcctgctct   82260
gctcaggaca gaatggggag gaaaacaggc tctgcggcac aatattggca agtgaaattt   82320
tgtaaaccgg ccctcccttc cttttgcatt tggtctgaaa attcaattag atgctgagtc   82380
ctacaatgta tttgagaagc ccaggagtgc cctagaggat gagactgggt ggctccctgt   82440
caggttgaac atttgcctta attactttgg caagatttgc atcagtggta ttagtccctg   82500
cctcacttgg aggcctgcac ttaagtggcc acattcaggc tccaatttcc tggtgatttc   82560
atagtgtagg gcacttgcaa tcaaaactag gcttaaagcc caaccctctt acattttacc   82620
cacccccaca aatgcagcaa ataaaatgac tctgattttc attccctaga cctcttttct   82680
atatttatta cattattgtt aagacagttt ttgaagaaag ctgttttatt taacaaaata   82740
gctttatgga atcaacttca tatatcttct ccgccagatc aaaacaagct cgtagtatta   82800
gatgtcaccg agcaccatga caggcagatg aacatcatcc ctgtgcccgg ctaatgatag   82860
ctcggcctgc cccggcgtca gccgctcctg gcagggccag cgggcggtgt gggaccggca   82920
ccgtatctcc agcaattcgc agataacaaa tatggttctg atgatgttac taaagatctg   82980 tcccttttcaa gattggatta gacattagga atttggaggg cttttttattg ctagcatttt   83040 taagaataac caattagagt attgattcta aagtctgaaa gccacatgga cagagttcat   83100
gtaattggct actttatgtg cctcttccta gattgccctg cattttcaaa acaagagcct   83160
ttctatttta atcaaaagaa tccagaatga aatgaggctt tgaaaactca gcctatgttt   83220
gtcttgattt ccttaactga catctagaag aaaatatgag ctcaggggtc cgctgggttc   83280
cttccagcgc ctaagcctgt aagctcttcc tgctggaacc aagctttaaa tgcacttgtc   83340
agtcatgtcc catgagaata gatactgcct tccatgtttt tttgttctga tttccgtgtt   83400
tgaaatgatg aaaatcattt ttctgtgctt tttaaaaatg gaattgcttt tgtgttggga   83460
attgtgctgt tcattttttac tctacctcgt tttggaatca ctaatgtggc caatttatag   83520
ccaaaaatca gtatcgtaga gtgagcaatg aatggcatgg tgactgtgtg agcgaattca   83580
tgccctccct ccccaccgct cgccccgcgt ctcagtcctc agtgatggta aacagaatga   83640
```

```
ggaccttctc ccgaccgtga tgcgcctcag ccctacttcc cttgtccttt cctatcataa    83700
aatcttcttt catagaaatg gtcatttctg ttcatatctg tggactgtaa ataacaagga    83760
agtcattttt gaggtgaaaa ctgcacttag actcattcca attttgatgg aaacttttag    83820
ctggtggatg gcatttgtt ttgtcttagt tttgcaagga gttatcttaa tttagggaga    83880
tgaaactagt ctgtgatccg aggtctcact tccatacatt tctctcgggc agtgtggctg    83940
cctgaatcat gcctggatgc cacaggtgct tagccagctg gtcctgtcgt aactgtcact    84000
ggtagctcag ggagtgcaga ggtgccagca gacactatga aattggcctc gtaaagcatc    84060
agttatgttg tgatggtggc aaagctgcag gcgagatggg aagtgcagcc actgagaact    84120
cacagtagag cgtgtgtaac gtaaaaagat gaaacccatt gtacacagct gtgtactgcc    84180
tccttgaagt caaatttccc ccattaccaa ggaaaagttt tttctgaagg gggctgcttg    84240
acaggatgac atctggtgat atcatttatt cctttggaaa tcaatctgtg gaagtgagtt    84300
tccactgact gatgaggaga aaaatgaatt ggcttcaccc agcatccagc ttcttatcct    84360
gggagagata gctcttggtc tgtcatccac gcagctgcct ggtgcaagag ccaagtttgt    84420
gcagcctgca gagcactctt cctgagctgt gggctgccag gtcgggggc aggggggcc    84480 tcactgtgca gcctcctgcc acccactgat catctgggga gactggccta tcctgtcagg    84540
agacgcagtt gcccagacgt tttcaagggc ctaagatgta ggcagttgat ccacagattt    84600
ttggagagtc cttgagttgg agattacagg tgacctcaga ggagggagtg agaacatctg    84660
ggtcatgggt ttctactagg agtccacagt gaaaacaaga agaggaattt acgacaagac    84720
agtccagcaa cttcctttct aacttctcct ttcacatatg ctggatactc caagactttg    84780
catttacatg gacatcacag atccacttg agagaagtag ggtaaaaaga ataaaataca    84840
tagtgcttta ggtgtatttc tatacatctt aattgatatg ggattacatt ttcacttgtg    84900
tttactgtac agactctaga cagatcctgc tcttttgcag gtaaaacaaa tatttcttaa    84960
aacctagaaa gacccaaaac aatttaacag aaacattttg gaccattttg gaccttggca    85020
gttaggcccc agtgcagcag cggcaaccat aaacctctcc ataggtgctg aacccaggtg    85080
atccctggca ccggcagcct tatgtcaggg ctctcttatc gctggttttt atttctccta    85140
ataaaagtga ttaaaagatt catcttttaa agaaagcaag gacacagagg tggattctcc    85200
ctgacgctag cacagctcat gcccaagcca ctcctgcagg gctctggtct aagtgcaaaa    85260
gctggaaaag ctgcaggtcc cgcaagacac agagcaaccc tgcaagccag gtcaccttcc    85320
ctcttctctg ctgtccgact ggccctccac catgtgacat tcaaaagctc aagttactta    85380
acctctcaaa actcagcatc cttttctgta cagtgggaa gatactggac tgttgtgagg    85440
attaagtgag gagagtggcc caatgaggtt gacagttatt actgtcattg tcattatttg    85500
ccttctcaca ggcaggcgtg ccacagtcat tttactgaag ctgcttcagt gggtcctgaa    85560
ttaggccctg tcctttggga gagacagtcc tggttcaaca cacagctccc tgcccagggc    85620
agcttgggag tgtgggccag tttcgccttt agaaccacaa ttctctgata tgtgcaatga    85680
gagaattaat tatagactca aaggattgca tgcagacaca cacagataca aacacataca    85740
cacaacacac agagttacac acagacatgc tcacaataca cagaaataca cacagacaca    85800
cgcacacagc acacagagat acacacagac acacacacac acacacacag acatacgcac    85860
agatgggcac acacagagac acactcacag agacacacag atacacacag gcacacacac    85920
agagagacat acacacagcc cacagggata cacacagaca cacagagaca tacctacaac    85980
```

```
acacagagat acacacagtc acacacagag agacatacat acaatacaca gagatacaca    86040
cagagacaca gatacagaca cagacagaca tacacacaga cacgggcaca cacagagaca    86100
cacagacaca cacaggcaca cacgtgcaga taaggtaata ttagctagtt caggaggaga    86160
aagagataaa gataaagtaa tattagctag ttcaggagga gtgaaagaag ccttgttttt    86220
ctccactttt tatagaagag aaagtgaaga ttcgatttga ggtgagttca gcacaaaagc    86280
gtatcccagg ccctctggct ccaactgcag ccctttctac ctcattccca gaccccacct    86340
aagccttttc tcttcaaaat cttctcaggc acactgatac acatacctca gatttttaat    86400
tctccggttg tgttcaccag gtgcttggtc atgattaaga attccgtgat gtgtaccca    86460 tgtgtttaaa tttgctgctg agttaacttt gtggcggcct gtggactaga cctctgcaca    86520
tgcaatgcag aacggcaggg ccagatttga atcctgcta tcttttcggc tgccttgtaa    86580
aaataacatc aggcgatggg gatacgatgc cagaggtcac ctgtgataag ttctgtttat    86640
ggccatttta cttctaggaa gacaggaagt gtcaggatct cagggatcta ggaagccaaa    86700 atgttttcc actctgaaat aaagtgactg accaggagtt cccggccacg cagccctgtg    86760
ggaactgccg cacggccact tttatgaagt ggacacgtgt tggtcccact gaaaagaaac    86820
tccccaccca tggctccctc acgctgcagc agaggccctg ccacagcacc tgtcagcccc    86880
tgccagcttg caggggcgca ggcgcagagc ggtttgtgcc cttgctggag ccagggaagg    86940
gcacagggtc cctcctggag tcatgggagg tgcagccgag gttctatatt aaaatacaga    87000
ggctagcaca tgtgcttggg gaatgcagct acagtagtgg aatgaaagtg ctgtccgttc    87060 cttaccccc cagctcctca cctgtcctcc acacgcatat ccctggctcc ctttccctag    87120
taaggagact gaattgaaat tgtggcttgc ccgaggctgc atacctgtgc tctttctgaa    87180
gcccaagtca ctggctctag aattctaacc tgtgaggaag ccactgagga tgtttgtcaa    87240
aatacatatt tctgtgcctt gccccagttc cacggcccag gaatctgcag ttttcacaag    87300
cacccccagg tgattctggt ggtgtctttg cacttcttca aggcagtact gcctggaacg    87360
cagaatccca gcctcctcta tcctccttgc ctaatggcct ggatgctctc agatctacag    87420
gggaagggaa ggtcacacag tcatcgcaat agtaacctca gctgataaat cctcccccat    87480
aaaacttatt ccccagtgtt ttttaatagg aaacaataaa actgtaacca gcccaaatat    87540
ccatcaaaga gaaatggag aagtaaatca tcgcacattc acctggacca gatctattgt    87600
aaagccaata atactgaagc cccttccaag gccctgggag tcctaacagt gcactggcag    87660
tgtctataat ttatattatg aaatttgcat aaggaaaaca ttttgtctca tttgtgcaat    87720
ttctccttct aaatatacgt gtcactttgt acctgatttc tataagaccc aggacctaca    87780
aaccctgtgt ctgcccctgc agccaccag ggaaggactg cacagcagca agacagattg    87840
ccatggagca tgttgtgccc aactagggac agcgcagata gattctgtaa tttgcctaac    87900
aatgtctata ggatgatccc atttgtcaaa aaaaaaaag aactgggctt tattgatgtc    87960
acctaaatgc acctaaactt ctttttttgcc ccatgctctt ctgtactctt gatctttccc    88020
caaattttta aaacatgac actcattccc ttatttttcc tacttagaaa agtgtagatg    88080 gtttatcat aggaagttca aaaaaattaa aatataatga aaatactca aatagtgcct    88140 cacaacagta actactgcta acataaataa aatccatatt tcctctcata cagaccccag    88200
agttgctttg cctgacagtg tagttgatgg agaaaataat ctttatcctt agcctccatc    88260
tggttgcaga ccataaagac agggaaaaaa tgagggtgtt ggtagcttcg ttagaaactg    88320
aaagctcact gatttttcca aaacctaaat agcctgtgtt tctccaaata actaatttgc    88380
```

```
agccttcggc agccaggact ggcagggatg gggctagggg gactggggag aactgctctc    88440
tcctgagggt ggtctgaccc gacagcacgc atgaccttcc cacagtcagg aactgctcag    88500
agacgtgatg gcaactccat agaatgaaat actcttcagc cagtaaaatg tattttgga    88560 taaatatttg ctttaaaaaa ctttactata tgttgttaaa tgaaaaaaaa accttaaggc    88620
atcagaaatt atgtgcagta aaatctcact tttgtaaata aatatacctg tttactacgt    88680
atgcataaaa agaatcctga gaaatataag tactgtatgc atattgttgt taagtatttt    88740
ttctgtttgc ttatctataa ttctaatttt gcttcaaaga acaagttact ccggcaatat    88800
aaaaataaaa taactaattt gtcttgtcat caaacagata gtaagaacag gcaaacctgg    88860
ccctccacac tgccagcctt ttgtgattca aggcttcagt ttcctccact tgttaaaaag    88920
attcaacaaa gtagttgaaa tagtatgtga accagtaaac cctaaaaggt gtccagtgtt    88980
gtctgtgagc taattaagtg atttgattct gactccccga gtcttctgat ttcgaagcag    89040
tggggagtca gacaggagcc tcaggtggcc tctcctgaga ggccctggaa agtgatgaga    89100
acctggcctc tggcagctct tcataaacgt ccatgttttc cctctactct ctcactcttt    89160
tcccagggcc tcaaacagaa gatgaaaatc aatttctaaa acagccctct gtgtgctctc    89220
tcgtatctct ccttttcaca catcgtggtg gtggctttct ctgtgttcct ctgttgattc    89280
agtctctgga attaacggat caggattcca tgcccagaat gctacaaaga ctgtgcttga    89340
gttctcccac atctcactca attacacaga agtttcagat tatgtaacag atgctgtgct    89400
gggttaggca gagccatctg acttgttttg ctttatttta gaccatgaga tgggtgagtt    89460
tttcttttta atgccacatt cttttaagaa ttaaaaacct ccacttggct gtcagcattg    89520
gaaatcagag tgatggtgca agccctgatg aggacaatgt ccttgtctat gaaaaggtga    89580
aatcattgct tgaaatcgct aagcaggaca tgcagtccca gatggagggg ggaattcggg    89640
agctggttgg aaaagagtat ttggcacttt gcagccttga gaggtgcaga agagacaccg    89700
aggggttcac caccagagcc accattgtca gagaggcgtc cagctgtgtc cacctgggac    89760
tctgccttca gggcttcttg cctggctggg agctgcacag gcagactcct gggacggtgt    89820
gccgacagct ctgggcaccc ccttctagga tctgattcct gaggaatcac aatgtggatt    89880
tcacaatcac ttccagtgtc ttttgccaac ctctgtgaac agatgtgcaa ttaaaaaaaa    89940 aaaagaaag gggcccaatt ctcaacactg taagtgaaaa cttttttaatg gaaaggata    90000 ggctaatgaa ttgaatttga aatctgagac agaaccgatg catcaaatgt gctggtgttt    90060
acagataata caagggggggc tgcatcttat ggtttcaatc cttttttaaa tttttgttct    90120
gagagaccca gccagcagac tgccgccagt cttgtcagag atgtcagtgg tggccactct    90180
gaatggaaag cagcatctct cagcatctct gaggcactgc tcctcagcgg agactgtggt    90240
ggctttgcct ttcagcacgc atcctttcta cgatgcctga cagtgcccag ggaatgggca    90300
gagctgggag ctctgaagcc cttcaccta aaccaccctg ggtcacctga cctagttttc    90360
ctcccaattt taattatgtc aggcacttca caaaggcctc cttggggaca ccatgagctc    90420
actgtcatca gattgctcca atcacagctg tggcttgcac acaaccgcca tctctgcccc    90480
agcagatgct gtgtgtaaac agttgtatta attacatctc aaaaacatgg ttcttgccag    90540
atcctcagga tttgggtgca gcctctgagg tgggtgggag gccctcgagg gagaaatgtc    90600
tgcaggaaat tcttccccta cgagaggtct gttttctaag ttatctaaga gctactgcag    90660
ctgtttactg cagagtgacc ctgctcaaag ctgtggtcac ccaaggcttt gaaagggggac    90720
```

```
ctccacttcc gccctgggtg gagcaccgtg ctggagaccc acgcctgcca aggcctcatt    90780
gtcatctcca cacgccgtcc ttggggtggg ccactcctgg acacgcaga caggaagccg     90840 gccacctgag ccactcggag gctctatcca gagtcagctg ccaagcctca cgtcacacat    90900
cactgttagt cttggagggc tggcggggcc ctgaagtcaa ttgaacactt ggatgacagg    90960
gaacttgcca ctgccagagg caatatgctc cattttttg acagttccaa caatttttct     91020
ttaaactgtc ataaaaaatt gctgctgtga ataccagtgt cggcgtccct gcctcacctt    91080
tacctggtgc ttttccacca cacaaaactg tttctcctcg tgctggcctt gggcttgcag    91140
acagctgatt cttctcctcc cgcggctgag cagcctcctc cgagcaaccc tctgacaact    91200
ctgctccttc tgacaacctc tgcaagggct gccagatgtg aacaaggggc ccgggcagaa    91260
ggtatccagg aagactggaa actcgaggaa gcctgccctg tcctgtccac cagactttac    91320
gcttgcgtca ctgggctttg ggacctaagt cctcgtcatt tgttccttttt gcagttccta   91380 ctgttctcag cacttccttc cagcttactg aggtacactc agatgtgata tgccatcggt    91440
acagacacag ttctgctcca gcatttcccc gtgttctttc tgtcgctcta tttactgaat    91500
taccgtgagg atgtggagcg aggctgagtt ctgtatttta acaccatttt aattctcacc    91560
tactgagaaa tccatcctct tatcactgtg ctttttttaa cctgtcacga atccatgaaa    91620
tcctatcagc cagcctgcat acttcctttt aaggtgcagt tgaatcagga gaaacttgcc    91680
gcacatgctg cgtccgggca cagcattggc tgaggctgct gccctgacct gtccgctttg    91740
tagtactgcc cagctatgaa acaggttagc cacacatgac ctgcatttag gagtaacaag    91800
tctgtctgta catgcacata cagcaacttt tttaaactgt ctatattttt tcctgagata    91860
ggtatttata atatctccat cttctttccc attttgaaac ttagaacaag tttgcctgtc    91920
aacagttctc cacagcatac tgtgtattct aggattttct aaggttgagc aacggaggtt    91980
cagcaatttt gacttaattt cttcccatcc cttttccacg cagcccagaa gccttggatc    92040
acgtggtgag gggaagaggt tgtgctatgt cgggaaactc tgtatcgaag ctcggctcag    92100
atcatgacat tctcttgact aaaaccctca gtttccatca aacttgtcac tctggcatta    92160
aagcctgtca ctgtgtggct ctgaaaacct ctctgaacgt gttccctgcc tctgccctgc    92220
aggtccctgt gctccacaga agcccactta tgtgacccac ccccactcat caccaccttc    92280
cctcacccag agcctcagct ccccactccc acctgtaaga cccctactgg aaagattccc    92340
acctgcccct caagattaat ctccaaggac atttccaaat tcctctcccc atctctcagc    92400
cagatggctt tgctccctcc aggaaccccca gccaccttcg acctccagca gggcactcca   92460
ctccacattc tcctggtctg tctggctcat cttacctgag ccatgctctc caggtgaagg    92520
actatgtcta actcaactct gctttaaaag cagctaacac attgctcttt gcatattgtt    92580
cactcactaa gttgaactgg acttggacat gcacactgaa ctgcagcgtc tgctgcttct    92640
tggtggccca gctcgtcaaa agaataagat ttcagcaaaa caatgtaaca attttttta    92700 ccaaaagtaa tgttaacaat atatggtttt ccctgatgt ttgcgtcaaa atgcttttg      92760 gaaaaaacat ttttcaactc tttagggtca gaattaagca atgaaattta taccacat     92820 gtataatgtg tatgtttatc taagtatctg ttcatttata tatcttaaat agaaatttta   92880
aaaatttttt taaaactcct gataaacatt ctcaggaggc acactatgta actgttggtt   92940
gatataccta gctagatggt gaaatcagat tttgtttaaa gcatggagga gagggaaaaa   93000
ttaaatcttg cagattctgc agtccttaac atctttgaaa gaggaacatt tcagacaatg   93060
taataagaag gccacgtgct ttgacttctg tagatttaa aaatacttct gtatagtttc    93120
```

```
ttcttcctttt gaagaagttt ggggagtttg ggaagatgga gaaagatata agaatagact   93180
ccccatatgg gtcatgaatt atcttttttgc atcagaactc ttagtgcagt ttcagtattt   93240
tcttcctcag gagggtgagc tgcttccgaa tgtcctcccc ttctttgagg catcctctgt   93300
tggtgaactt tgagagcatc catttatgaa gttgatgacc tttcccagtc tctgcaagcc   93360
cttcagtgtg tgtcctctct gagcaaatct gaattgtgtg cttaatacat ggaaagggat   93420
ttgggagggt tgcttttttaa actgatttct taattaatat tatggtttag ttaactagac   93480
agtctcattg cagaagtgca taaccataat atgtcttcaa atatatctcc cttcctaaca   93540
ccctgtaata tacttttgta aagatacccct tacagaatgt gatccaccat ttatgaacct   93600
gcagcattgc attcagagac taagtgaaaa gctggcagat tttcatttaa agcacaagct   93660
aaggaagaaa gctggtctag aaggagctac agaagggtaa tgcttaggga gggaatgatg   93720
tgcctgtggg tggtggtagt taaatctaac caaagaatga tgtcgtgggt gtttggatat   93780
tggatggtcc acattgggcc acattctttc aaacataaga gtctgtagaa atgtgacctg   93840
taaaagactc ttaaatattc tggaaactgt ttcttccttg tcacatcctt atatatactt   93900
gaacctatgc ctaccagaca tgacatgtga ctattcatac agatttcatc atctctggtt   93960
taagaataaa ggatgctgca tagaaggctc acatctttta attcacaaga ctgaaactgt   94020
tctgaaatga cattgtttct aaaaattcat tacttgcatt atattcattt ttattttttcc   94080
atgccagaag ggtagaagtt cctgtgctca tattaagaaa cagcaatgtc aatcgaggcc   94140
caactcaaat ccaatttata ggagttataa agggcgtgtg cctgttttgt ctagaagcag   94200
tgttgggcag cactgagtag gatagaccac ctgttgctac cgataaagga gcagcttctc   94260
gaatgctcct gtctggtagg cactatcccg agtgctttgg cccctcatcc acaatctgtg   94320
tggcaaaagg cattgcaggc aattcagtga ggagaccgag gcatggagag caagtgccat   94380
ggaattccct aaggccgtgc agggagcagg ttgccaagct gggttgaaac cgtcctccgt   94440
aggctcccaa ctccgccgtc gctgctactg tgctggatga tgcctggtag atgcagatgt   94500
ggagccccat ggattctgag acaggccggg tttcagtcct gccctagctg cctattggct   94560
ggatgacctt ggcaagttga cttctcgtgag cctcatttgt ctcatctctc aattaagaaa   94620
acctagagcc tatctgtggg ggttatctga aggattccag ggatgcatat ggcactgtct   94680
accgcatgcg gtaactgttt cacaaatgat gaggagcgat ttatgttctt agtggaaata   94740
tgtcggcgtg tgaagtccca aagctctgcc ctgcctggct tgatccagtg cctaggcact   94800
gcccctcttc ccctctctcc caacccactg taagaggcta ggctgcctca gtaactctga   94860
ggggcattga ctctttttcat ccaaaaattc atgttactgc cccacatttt ttctgttgtt   94920
ttacaacgca gtaggaagtg ggcagactgt caggaaaagt gatttatagt catgtattgc   94980
ttgtgctttg gcttcatttg atccaatgca gatcagctgc actcagaaaa ctactcaagt   95040
gaaagagaaa aagtaactga aggggggaaat ctggatgagt aagaattcca gggatagaa   95100
tattaatagc aagcttttg cctgatatag tcactttatg ctgcaggggt gccccttat    95160
aaagtgcttg tacaatggat gtttgctttt gattttggat ttggagtcta atgaatgttc   95220
taaattatta ttagaggagc ttgcggttgt tacatgtctg cctttattgc ttattttag    95280
ccatctcccc tgatgtcaaa tgctcaggca agaatgatac attcatttat aatgtggctc   95340
cttcagaaat ataccacata ccttttggtg tggtttgtgg ctgagaagag tggggaatgc   95400
acaagtggaa aactgcagaa agattatgcc ttcatcactt caagtatttg agatgaaact   95460
```

```
agatcatttg ctgttgctttt ttattctcat tctaagtgct tttcaaagtc agcgctaaga    95520
ttttaaaatg gttttctgtt gttggcagag agggaattac tctattactt tctgataaaa    95580
cagagtcttt catgatcaaa gagaaccagg ctctagtagt tccagtatcc taacgtggac    95640
actaattgtt tccctccttt tcttcatgaa aacagcttct gcacaaatga tagccttgtg    95700
aactagccat gggcacaact ggagaagcat ttagggagct ttagtgcaaa ttgagaccac    95760
ctacacatct gactctacag ggtttgacaa catccagggt gaatcacaaa acatcagtct    95820
aatcagggct tatatagaaa gagtgaaaga actctgattt catcctaaag attatttata    95880
ttaaccattg ttccaaatgc attaactatt ttaatttagt tgttttgatt gttaaaaaaa    95940
acacatctgt ttggtagata agacataatt taagacaaat gttctatttg ataagctttt    96000
agaaacaact tatttttatt ctttcctgtg agataactca gatgtggaga atgtgacaaa    96060
attttaagca taacatgaga agggctgaca cacatagatt tctgtgtgct tacttgaaaa    96120
caacaaaatt taagaatttg gtataggagt tgtatcaggt agtgcagagt ccccaggaga    96180
cctagagacc caggtctggg agcctagcgg caagggctga atgtgggatg acatcagcag    96240
aaactcacag ccactgctat tccaaaaacc cagcagcagc tcagtgcagg gcagtgctga    96300
tagtacagtg cctgcaatcc tggagtggat ttggatgtgt caggtacgca cacgctcact    96360
gctcccccag cagtacgttg aacagtgtgc gtccaggtgt ctgtagggcc cctcgcccta    96420
actcacaaaa ccattctggg tcagaagcca ccaatattgt catcatcctc ccttttctga    96480
gaaccctagt aagtccctcc agtggggcaa gcccaccttt tcccttcatt ctgtggcaat    96540
atgccttcat ttcctaatca gttttgccct gctcattcaa tgcaaaatgg atctgctttc    96600
cttgggcacc aatatgtcca gggattgttt atcaatcttc agttctgttt cctttacata    96660
tccctccaaa aatcaggcct gcactgcctg tgcactccac aatccacagg cctgaaggaa    96720
atgttatctt tgatgtagag acttaaagta aaactcttca aattaattat ttcatgcaaa    96780
aggctagtcc tgactctaat tctaagacat gtctcctaaa ctctggaagt ctgatgtatc    96840
ctattatcaa catttatcct taatgtgatg gtttatcatt tatcctcaaa gctgcattgt    96900
aaaatgtaca ctgtaaagtg tacattttaa agtcggtttt aaaaaatcat atttagagat    96960
cctggtaaaa atctatcaag tcaagacatt accttattac ccatggaatt gtcttcaact    97020
cttacagttc aaatattcct gaattggctt tcacaataaa catcctaaat atgtaagtag    97080
aaacatatat attgccaact ttgtgccttc ccaagcaaaa ttaaaataca ggaaaagtca    97140
gtttgttttg cccataaata aatatatgtg tgtgtgtatg tgtgtgtata cacatacaca    97200
ctcagaaaag atagaagcag cagcatattt tggcagcatc tggtttattg gaactcaaac    97260
gttctgattg tgcatacaga ctagttaatg tggtaacaat tatgtatttc ttccctgctc    97320
cttgccttct ttccctcccc agttttttc ttcctgatag taggtgtgta ctttttttcct    97380 atttccattg gcaagccaca tgacaagcaa aacgatcact cgaagaatat tgttccctca    97440
atcaagaaaa atgcccattg ggttttgtta tttgatgtta tttgatgaca gagacctatt    97500 gttttttccat ttttctttttt ttgttttccg tggcacctat ggaattaagc aatataaaaa    97560
atctattatt tcagatgttc acgtctaatg aatttcatgt gaaatactgg cagtataacc    97620
ccaaatagag gaaatttgtg aagagtggat gctgcagggc atgagacatc tgcacagagt    97680
tcatctcttc cagcatcttg catgtcccaa gcactgccct gccaggcaga gaatgctgca    97740
gatcacggca gtgaattcca gttgttcaga gcacatttga cttccaaatt ctcaggcca    97800 cagatttgag gacagaacaa tatttgcatt tgaaattgga agattatttt ttgcacaagt    97860
```

```
gcctatatgc tatatagagt ttgcccactc tgcattatct tccccctgtt cccccgttat   97920
ctggcacaag ctattcaaaa gacacgccta cttgtaaaat aaatggtttg caaactaagg   97980
aaaatactta aatctcatgt aaatggtact atactatgta taaaaatgtg aagaaacaca   98040
gaacagctca tgaacacctc cactgctgta taaaagaacc atcttttttc tggctcctat   98100
tggatgcctt agaaaatct gtatttcctc tttagttatt gtgtttgaaa gatgaagttg   98160
agacaaaagt tctattcttt ttaagttggc agaacttctg aaaggtgatt tttagctgca   98220
gtgtgactca ttccaaatgc agaaatctct gaccctgagt tagtctattt gtcatgcaag   98280
agcctagaaa agccctgagt gataagaaat ggccataggc cattcccaca gaattttcaa   98340
caaaaataga atcatgctta tgttctagtc atgacttaga acttataact catgttcgga   98400
actgtccatg ttcacgcaca ggggccgtat cactccgcca gagctgccct gggtgccggt   98460
gtgcagaggg gtccgagagt gactgtctct tcctctgttg tcgaatgtgt gggttatctc   98520
cataaatggc tgccatgagc atccttgttc acacattttt aggtacttga gtgagtgtct   98580
gtggaataat tttgggaagt gaaatctgtg gtcagaggtt tgtgagtttt acatgctaca   98640
ttttcagaag ttgagaaata gcagtaggct gaaggcaagt cgccatgcct ggaattcatg   98700
aacactagtt gaaagaactg gcgtgagtta gtcatgacag gagagatggg gaagggagtt   98760
gcaggtagga gggccatctt caaattctca agtatagtc actccaaacc aaaattcgat   98820
ttaatctgta ggactccatt ctcaaagcac agtcactcca aaccgaaatt cgatttaatc   98880
tgtaggactc caggtggcag aataagaggc aatggatggg tggaagcgaa acagggccaa   98940
agtttgactt catgtgcaac ttcctaagga gtgatttgaa ctccacaaac atgaactaag   99000
cacctcaaca caggctgggc aagttgctgt tcttttggag cttacatctt agtggggaaa   99060
gagaaatgcc tatgtaaaca tataaatcag caggatacat tgtgaggacg gtcattgctc   99120
agtgagactg caatagagtg atacgctgga ggggctgca agggagaagg tgggagggac   99180
agcatttagc agaatgagca gcacagtccc ataggaagaa gaatttattg cctccttagg   99240
caaataaatt cccaaacctt gaacatcaga aaggaaatag attaatgtgc acagaggatt   99300
aaattatgtg atctgcaaag tcatttaaaa tctatttcca cataaaacat attaatgcaa   99360
cctaaacaaa aggggtctgg ataccctcat cttcttccca agcatcaagt ctttctatag   99420
ttaaactgag atgcttttat tcttggaaaa ttttaaggac tatctacagc aatggaagaa   99480
tcgggtgttg ggatgtgttc ccaggtaata atgactgcag gctgatttgg cccttgaggt   99540
gtggcctcat ggccctctcc aaaaaaaatc aaggacctgc tacaaagcac aaagccgact   99600
gcaatgcttg ctgcttactg gttagggcag ctcctctttg ccagcgacca agcagaaagc   99660
aagacaagac aggttctgaa gcagtaattc aaagccttcc tcgctttccc atgtgagtca   99720
ttgctagtca gaatattacc tttgcagaga ggcttaattc caaatttgct cttaaaggga   99780
tatcctctcc tggtttaggt ataaactttt gactcacagg acaaattcta tcattccttt   99840
gggcctagga ttgcatttat ttccatgaca aaagggcctg tctggtgttt cagcaaatga   99900
aaacaaaaat ataaagccca tctccttttg aatgagctct aaaacagttc tccactggac   99960
ttcagaacaa gagggagctc tgggctgctg gctggttgtg catttgctgt gggttccctc  100020
cggcaggcga cctctccgcg ctgagaaggt tatccggata accaagtaag aaagtacatg  100080
aggaggcaca gaaagaaaaa tgtgagagat aacagcataa acacacagtg tatgttgtta  100140
tgaggcatca catgatgaga tactgctggg gagggaagaa gtgaggagat tcctaggaat  100200
```

```
cttatgagaa tttccagaga caacaagttt tgagcttttt tttaatttag aaaatttacc   100260
ttatttttaa aagaatatgt aacatatccc atgctataaa attctagaca tagtagattt   100320
aaaacagcat aatggaaaat ataaatatct attttctttt cctatttatg tattctgtgc   100380
cagtaggaat gtagccaaaa agagagaaaa ggggtctctg cagacatgga tgtctctgtg   100440
acttgatcac tgctaaccca agaagataat aaagcagaag catgtatcca ggttgctgca   100500
gccaagcctg cccggtctgc ggggcgtcct cacacatggg gcagctctcc caccccacac   100560
actgggaaag gcggacagag gctgggcaaa gcccccaatt ttcgttggca ctgaccccga   100620
tgatttatag gcctttgttt cccatgttaa atgtcttacg atcattaaat tatttatagc   100680
tcaattagca tgtgtccaaa accaggaagt tcataggaga ctgtgtgact gggaattaag   100740
gagcaaagca actttccagt ctgtgattta ctgggtttcc attctgtttc ctgttcggat   100800
ccggaagtag aatttcaaat attgcttttc atgcttatt tgggaccgat tttagccccg    100860
ctctcctttc tcttgccatt cgctggccat tagccaccag cctctgcaca atgaccagct   100920
ggccccctggc agatcttggg cccaggtgtg aagtcgctgg agaagcattt cagggccaag   100980
atgggagtga tttcattttc cattgacact atgcagaaat gaaggggatt caagtgcctt   101040
cagaaaagct tccttccagc gaatggagtt ttggggggttt tccagacttg caactgcttt  101100
tattcttgga agcatcattg ttgcttttc ccccccttcca tttatatccc aggaactgat    101160
tcagaaacca tagaaattgg atttggaatc gctgaatgct agcagacagc tgactgcact   101220
cttcccaaga aaccctgcca gctgggttcg ggtatcgcgc ggtgtgtgct ctctctgcct    101280
ggcccgctga gtcctctaac tctaatggat tccttcttac accaaagtgc actagaacta   101340
aagtgttttg cttcattctt tagacatttt gtggtttagg gctcaatcag ccagggtatg   101400
atttgcaatc cacagtaacc ggtttcgag cagctgccca gcgaggcagg tttcatctcg     101460
cttgctagac gttttgtttt ttttttttc taaacctcac acctttatt tattagactt     101520
ggattccagt ttcctgagcc tgtttgtgcc actgattaga caggcttgaa gcagaaccca   101580
ccaggcttcc tgaataaaat gcagcagtga ttgtattagg gggttttaaa ttgctcaaaa   101640
tactgtctaa aaaacactaa aaatcatgtt actttctaga ttgaataaaa tcctatagaa   101700
atgaattcct ggacttgata tgtagcaagc tggcattggc tcgggagtga gtgggctcag   101760
ttaagtgagc taagatgaga tggtgcacag gcgagcaccc acctgaggag tgtttggatg   101820
ttatgatagc cagctcctct gtaaagacct gtccttctat gtcagcagcc cagcagataa   101880
atgacgtgta aataccacat ttaggagggc ttatgatgat gccaattaat ggagaccttt   101940
ttgaaacagg aaggaggtga acatattcc tttgcttcta catcactgtg tgccaggcac     102000
tgtttacagc atctcgttta accagcagtc accacctgac ggatggctga tgtgggtgg    102060
ggtcccaggg tgggattgcg tgatgggctt ggggtctctg gctgatgggt gccagagctg   102120
ggactggaac tcctggcgtg actgaggcag acacctgggc tacccagcct cacccacgac   102180
gccctcacta agtgacccac aggactcacc ggaagcaggg cagcaaggtc ccctacaga    102240
ggtcccccact gcaaaccgat acccagctta gacagcagtt ctgcagtcgg cgtctcaccc   102300
cttcgggtct cattgtgact cactttgata gccacacgat ttaagggtgg ttcagtagtg   102360
atttgatgag tgctgtggct cagggtcatt cccctgccca agcatttcaa attccagaag   102420
ttcatgccct gcatggtggg tgaaaagtct caggccaacc atgagcacac agcagccagg   102480
cgactgaggc agctgcccgg ggtggcacgt tgctcaaacc catcatttgg agtcaaaaca   102540
aacagatgat tagctggggt ggtcactttc aatcaagagt tttcacatcg cctagacatg   102600
```

```
gcctcagaat caggcctggt gtggccaggg gctgatctca cagtagacag gaagtgtggc   102660
ccgagggcca tggctgcccc ctcagaaggc cctgtggagt ggctggccga gcctcagcag   102720
cctcctgtga agcgaggaag ggtcttcctg ccggcctctg gagatcagta tgggaatgca   102780
caagtaggaa acgctggatg ggaatccctc tgccctgtga taccaaggca gtgagtttgt   102840
agactatgga attgctgtcg gagggctctg taaccggcca aggtcacaca ggtagccatt   102900
ggtagagcag ggactggaat cccagacccc caacttccag gactgtgcac ctttctttat   102960
cccatacagc cttacagtca agtgccagtg caacacctga ttcccaggtt ccagcctttg   103020
tcttttataa tgggaatcaa ccttatcttg acgatccaga gatagtcatc aaggaagatt   103080
aaattatccc cttagactca gagtgaccat atcattttcc ctccacacaa ggacactttt   103140
gagaatgaaa aggaggagat gtctgtacca gacgctggat gacaggcacc gacaggctgt   103200
ctgccagggg agcagcgatt cctgtatgtt gtagaaagtt tttcaaaagt caccttggaa   103260
agaggttttg ttccttaacc ttctgttaaa taggaagctc cgtgaatgaa aacaactccc   103320
ttccctaaac attctagtaa tgacccaaca ctgccaagcc tgccagctct gcctcatggt   103380
cgtgttgact gtgtgagact atgtgagtgc ctgctacaca gtacgctttc agtaaacatg   103440
gtattgcctc gataatccca caaaaatgtc ctattcaaat cacctggcac ccaggaaatt   103500
tccttctttt ttttcccagg tgaaatatac agttgaaaac acctgacagc aattcccctc   103560
tcccatgtgt ttgcaggatg gtggttttgg ttcctccatc tttgatgtgt acaagtgtga   103620
tgttttcccc ccacagacaa gtaaaccaca ttctcttcac attcccaatg tttttgtcaat  103680 gtacctcctt caatagagga tcgataagga aaaaaatcat tgacaatctc aattagattc   103740
actatttcat ccaaaagcat agcttagaac tctagttttt gttcaacact cttgccctat   103800
gagtgcacag aactttaatt ctgatacaaa catccctgaa tgtttagctt tgacagagat   103860
tccaaggtga tttgataaga agcagggctg tgtttgggct ctgggagttt ttgatatggt   103920
ttcaagcccc atccaaaacc cacagacctc tagaaagtag gtgcctgcct tcctgcagca   103980
gccctggagc ctgctggggg ctttgagcag ctgctgccaa gccaggcctc acccgacact   104040
ctgatgggca cggccatggt ggcagggggct tggacgctgc caggtgactc taacttgtgg   104100
ccagggtggg aagcactgct ccacagaggt gccaaaacca ggttccttcc tgtgttctca   104160
catttcacag cctcaatgta aaagtaaga catgggcact ctggaatatt acaaaaatat    104220
agaaaagcat gttatagtaa ataaaaggct cacagaattt tgtcatttag gaacaatgat   104280
tattaatata ttagtgtgtg ttttttgctca ttaacagtat atcctgagat atttcctata  104340
ccatttaata ttttaaaaga tgtttacact ggccacagta gctcatacct ataatcccaa   104400
cactttagag ggcaaggcag gaggatcact tgaggcttaa aaattagcca ggtgtagtgg   104460
cacatgcctg tagtcccagc tactcaggaa gctgaggctg gaggatcact tgagcccagg   104520
agttcaaggc tgcagtgagc tataattgca ccattgcact ccagcctagg tgacacagtg   104580
agaccctgtt tctaaaataa ataataaata aattaaaaca tttaaaaata catgatgttt   104640
aattattaga ggactcaatt ttatatctat gtatacaata attttttaagt ttcttaatat  104700 tggacttttta gtaccttttt aaaaatacta tttttaaaaa aatctgtatt tctaacttttt 104760 tataacaagg aacctttggc tttgagatga ctggggaatc cattctttcc tatagtatcc   104820
atgtccaatg gacttaaagt attaatcaat gtgtttatgt tttgttattt ttctggcatt   104880
acaaaaaatt ctaaatatat tgttaccgcc tgtataaata tcagcttttg agagaaggac   104940
```

-continued

```
attgtgtaga aataatgaaa cactgcaact tgtatttgta ttattctttt tttttttttt  105000
tttttttgaga tggagtctcg ccctgtcacc caggctggag tgcaatggtg cgatctctgc  105060
tcactgcaag ctccgcctcc caggttcaca ccattctcct gcctcagcct cctgagtagc  105120
tgggactaca ggtgcccgcc accgcgccgg gctaattttt tgtatttta gtagagacgg  105180
ggtttcacca tggtctcgat ctcctgacct catgatctgc ccgcctcagc ctcccaatgc  105240
actgggatta caggcattat attattcttt aaattcacat gagaatttag tatggcttca  105300
aaaaatacca taagttaaaa tatcaccaag actctgttca gacaaaagta tcagaaaagt  105360
gagccaggca ctcacatagt ttatagttta taaaagtgag acaggcatga tctcttaacc  105420
tcactatagt cctgtgaata aggtttattt acatttcatt ttacctgcca ggattattgt  105480
aaaaacgcca agcacattgc ctacacaaac taaatattca gtcaatggct gctattttca  105540
tgagttcgtt ttaacatata tttattgtcc tctactggat ttaagaagtt atatttatta  105600
tcatctaaga ttttagctat tccttctctt aaaaatagat tttataatca atggcagtaa  105660
gggagagtaa ctcgcagttc tctgaatctc aaggggttcc tggaagcctt cctgaaggta  105720
tagtgaaatt tcagcttcac attcccatct atgagctccc tgcaaatatc ccggtctgct  105780
ctcaggaccc agtgacttac ctatgcagag gctgtagata gcacctggag cttcctgtgt  105840
gccctcctca aactcagcca atgccgtcat acagtagcag gcaggtgtct ttgctgggta  105900
gttggactgg atgtccctgg gattgcagaa ctggaatggg gagtgacatc aggaaaactat  105960
aatcatcagg acaacatggt ttgccataac tttaagtttt aagcgaccgc agattatgcg  106020
gagagagatg catgcccaca gccatgcttc ccatgtaact ggagaggggt ctgaagtttg  106080
aaacaagtgt tcctaggcac gggttacagt gtttgttatc atcatacttg atttagaatg  106140
gggcacaaca tgtggattca tggtaactgt tacaacctta ctcattttaa tacctgaaaa  106200
catgctttcc ccatgctggg aatcgaaaga ttctcctagg aaaagaaagg cttgacaaca  106260
tcgattcaaa aagggcatgc attttcctca tttaaataac tctaatgtgc aagtagatcc  106320
cctgacctca agctcagaag agtccaggcc ttcacacctt ctctgcttct gctctggggc  106380
cagctattga gattcctgtg cccacgcaat gcgcacatcc caccctggc cgctgtccac  106440
aagaaatcca gttgcaccaa gcaccccact ttttgcacct ctcatttatg tactcctaag  106500
agcctcacca caactccctt ctaaaaacat gagttcctga ctgggaattc gatgctgccc  106560
aggcagcttt gctcagaggg agcagccttc tagaaatgtt tcaagtaaac tttcaagtat  106620
aactaaattc aaaaaaaaca catacacaca cacacacaca cacaagtcaa aggtgtgtaa  106680
tttggccaat atcacaaacc aattagccct ttgtaagtgg cacccagatc aggacagctg  106740
accataccag caccctagaa gcaccccgtg ctgcctcctg ggacagggct accaccatcc  106800
taaggccagc acgatgggcc agctttgcct gctgttgaat tttgcttaca tagaatcctc  106860
cagtaggtac tccttttgggt caggttcttt cactcaacat tatgtgttga tattttccca  106920
tgctgtgctg caaaattgta tttcttgcat tccataactg ggcagttcca tcataggaga  106980
ataccacact gcgttcgtcc attctaccgc caatggacat atgggttctt tctcttttct  107040
tgcagttaca agtttatgaa tattgtccca cgtgtccctg gtgaacttt gtttgcattt  107100
ctgttgggta cctcagagtg gcgttgctgg gtcagagggt actggtcgct ttagtagctt  107160
tgaaagatat tgccaaaaca ttttccagcg cagttatagc aaattataca ccaccagcag  107220
tagaaaacat ctcctaattg ctcacagtaa acccccaaag attgccacat acatcttcca  107280
tatcaattac ttaactattc agcaaatttg aagggaaata tatttaatct ttttattcaa  107340
```

```
atagtttata aagtggaata gagatgtggg taaaagttgt cttgccacct ttttagatcg   107400
gtaaaagttt gttgaatgca ggcaagaaaa gatgagaaat aatggtaccc aatgaaagac   107460
atagcagtct acaaggaggg gcatttcccg gggtgggggg gacccacact ctgtaactcc   107520
cacattcaat tagcatgtta taggtaagct gcagaaaacg aggcagcttg tcaaagagga   107580
acggctcttg gccatggttg ctgccctagg aggatatttg atactagcag agctggggca   107640
accctggagg aaaccacctg gaatgatggg agaactcctc cagggaacat ggcccttta   a 107700 tagatctctg ttataaaaaa taatcccaaa gcagccacca gggcatactg ctgcgatcaa   107760
gtcctaggcg gtattccctt ctgcgccata gaccctgtgc agagtgccct caacgaagga   107820
gcaaggaaga ccaagtctcc cgagggtttg catatgtgta tgtgattctg cagtcatggt   107880
gaatgacaca gtcagggctg cggaaaagca ttggtaaagt gtatatttga ggcttcagaa   107940
gtttgaaaag gctagatttc ctaggccaaa acactgaaaa tttgcaatta gaacttcagt   108000
gctgatgctg ggaagactgg agttagtttg agacatgcac ctgtgcagaa ctgggccccc   108060
agaaaaggag aaggaaggga atccagacca gagtagggcc tgacaccact cagactcggc   108120
gtgtctataa attagaattg cgttacaatt acactttgac atttagtgg ttttaaagt     108180 gcccagcaca agttaatttt tcattaatga atcctttatt cataaaatgc ttagatggag   108240
attacccttt tgagcatttt gccagtgctt ctgaaattaa tggggacctc ctgttggagg   108300
acacagtctg ttgcaatagg tgaccactgc tctgaatcta tgtcacctct ccaggaccac   108360
gggcacaacc atcacctgag gcatgttgga gatgcagatg gtcaggccct cctagaatct   108420
cagaatctgc attttagcaa agtcctgggt aattcctatg tccattggag tttgagaagc   108480
actggtaatc tcaaatactt taaaagatta ctagagtaag ataggctcag taggtacctg   108540
aaggcaccat cccaaagacc agagtggtag aagcaggtgg accagcctct gaacacattt   108600
ctcccccact ccccggctgt gtggaaggtt gccacctttg gggtagtcat tcaacaaaca   108660
cgtgtcaact gtccactatg tgtcaggcca ccactgggca ctggctgtgg ctagctggat   108720
agacaccatt tctgccctcc agaaatgtca tgtccactgg cacatgacaa gtcactaagt   108780
cattcagagc catgggtgac agctccaggg gccgacaaag gagctgtgat ctcacagatc   108840
cacagagaag tgtcccaggg cgggcgggaa ccaggactgc acaggagggg gtgaagtgac   108900
acataagaag tcagcccatc agcctgaaat gctcccccaa atcttcccat tcagtgtttt   108960
ctcagtagca aactcgtggg aaaattggtt attttactta aaaaactcat actagaaagc   109020
tagtttaact ttaaaaataa attttaaaaa cattttatt aacaaatcct accttttcctc    109080 caaagtcaag gagaaaagaa tagaagtgaa caatggacca agtaagccta aaactctgct   109140
cttccccctg ctcattttac agttcaagtg ccattcaatt tatcctggca agaagaggaa   109200
ggcatcatca agaccttaat tttctaatac atctgatctg agaagaatgt gaaagctata   109260
aaattaattt ttgatcaata actacaggcc ttttgagaga gtgccctcct aatgaattga   109320
gtacctattt ctccatacac agtgtctatc atgacctaca aacccttttc ccatgaggtg   109380
taacagagag agattacagc cttggaactg gatgtcagac tctcctggtt taagacaata   109440
agccatgaca tagagcctga aaccaacaca atcttccgag tggttccaga acatatagg    109500 ggataatgtt ggctctgatg ctgtacatcc ccaacaacca tcaactattt ggaaactaga   109560
atttcagcat aattggagtt ggtgttaccc tagcaaatgc tgtgggaaga gagtctcact   109620
gtgtatcttc tcctgtttaa agcctgaatt tgttcagaat gtaatatctc tgtttagcca   109680
```

```
ctctactgaa actgatctag gaaatgttca aaaaaaggta tcccaaggat ccctttgtag    109740
ctacatctgt gggattcccc tcgctctggc gtggcctggc ccctctgcat ttgacaatac    109800
ggtcctatgc ttttgtcttc ctgggctgcg tgaacccacc ctgccctggt tcacctctcc    109860
tcttgaccca tccttatcag tgtcttgaaa ggtccttcta ttggaggaca cattctgttg    109920
cagcaggtga ccactgcccc aaatctgttt cacctcccca gggccatggg cacaaccatc    109980
cctggagtgt gttagagatg cagttggcca ggtcctccaa aatctcagaa tctgcatttt    110040
tgcaaagtcc tgggtaactc ctatgtccat gagagtttga gaagtactgg tctcatgagt    110100
tcctgacata caaatagtgc tgaggccagt atgctgactg ggtagccaga tacaagtgaa    110160
aaccttcctg tttttttgcaa acctggatgg acccgaggcc gctgacgtgg gccaggacaa    110220
gctactcttt ttcagtgttt ctgttgcatc gctgtgtctc tctgtgatca ggtgctgccc    110280
tccctggcag gaggactgca gacaggatga ccaagagcac tctacacagc ctgctctcca    110340
gtgttggggg acgccaccca ccctcgtggt tcctgttcat ctgcctacac gtggagggcc    110400
caagagggct aatatgtgac tatctccact tcctggtacc ctgtgtgaat aacttcactt    110460
actaaaggga tgttgagcaa ctttattaat aatgaagaaa gcactttggt ttgacaaata    110520
atcactccat tttttcattt gaaagttaac tcttgttagt agagaaagca atgtattaca    110580
accacaagga cgtttacatg gaaatgaacc atctgcaaag catcccccat tttccttta    110640
aatcagccaa tgggtggtgg tgggagaaat attcaccaga gtatttaaca tctatccccc    110700
ttcctagact gtcagctcca tccgggcgga gactgttggt atctccacag cacacacagg    110760
gcctggcaca catccggggc tcagtgagca cttgctgaat ggtgaacaga ttagctctcc    110820
tgggaacgtt gttgacacat ctcataacac tggtttggag tggagggcat tcatcgggct    110880
gcatattcct attttaatt gtattctcca ctggttacag cacctacagt tataaagaca    110940
ttgttaacat tgcttatagg aagacatttg atggaaatga gtccaaaggc attacggtta    111000
gaaactggcc aggtgtcatt tttgagagat tagataactg ttttccggta gagtgaattg    111060
cctgtttgtt gcaagttggg actttgctgg gctggtttac agggccaagg ggaaagagat    111120
aagtggatct tctagtgaga ggtcatctgt tttgaaagcc tggaagattc catgaactaa    111180
atccaagtct tacaacacag ggaagtgtgt catactgtgc agggatgaag tctccaattt    111240
agcatgaaaa caagagctcc tcacactgtc ctcttcagaa agcccataca atccaaactt    111300
ctgaatgctt agctgcttac aaccatacat agattgaggg ataaaactct gatatggaag    111360
agaaggtaaa catttttttgg cagacattcc caggaaaagg cggctctctt ctctcattgc    111420
tgctgctctt tcagaatcca tttcaacaga ggaggagtca atgggagccc cgtgcctctg    111480
gcagatatca tatggcgttt cagtggcatt gtgtgttacc cttcttaggt aacagctcag    111540
ccattagaag aatgtcctac acaccttctc attttctgtg atgagaggaa tgtgaggtac    111600
tgcccttcga gagctgtcat ttgtcctagt agccagcagc gtgactgtgc tgtcttctgc    111660
tctgtctccc tgtcagcctt ctgcccagcc accaccacta tagttttgtt ctctccattg    111720
gaactcctgg ttcagagaat taccataaaa aacagacccc tagacataca acactctatc    111780
acataatggt gactttgtct tctatttttgg attactgagc tttcttgggt aacttccact    111840
aaatcgaagt taatattaga agaacttcct cttactagaa tcgaaaagca tttaagtgat    111900
gcagtcaagt ttgtaccata agtaattcag tcatttaaca aatatatatg gcctctgtgc    111960
gacagtgacc ttgactggga atgaagctgt cccatgtggg gcctgttctt caaaggcagt    112020
tccctgctgc ccagttcagt ccagtggatc tgggcatctc tctttaatcc gcattagggg    112080
```

-continued

```
ctctttactg attcttcact atccaaaaag acttggaggg gagacctgag cccacttctg    112140
gaaggaaatg ataacaattt atttagataa tctttgtgca acaagtcaat tcactgaaga    112200
gatctgctct ctaggagcct ctgtgacccc accataactg ggaaggctct acctctccag    112260
tcttcgggcc acatttctct ctggcctgct gtcttcccag cactctcagc cttgctcatg    112320
gagcactcta gtcctccgtc gaccttggcc tttggtaacg tgattttttca cctggcagct    112380
cccatctggt ctcactccct cttttttgtcc agtctgcatg acacagcctc acatcgttag    112440
tgttccctca ctcccctctt actgcccaac ctgcaaagtc catgcctggg ccagtgcagc    112500
atgtgtcctc aatgggctgc tggtggcagt gggggggaacc gcacagccac gctgtgtgct    112560
gctgaagaaa tgcacagcct cctaccctcg ccctcaagag gcagccatgg ctgcgcattt    112620
ctgcccttct gagctccgct cacttttggc agcagccgtt ccaacctgca tgggatcttc    112680
actctctcac agatgtgctg actcctcctg ctgcctcccc tctctgtgcc ttctcactct    112740
ctgttccctt tgccctttct cccctttttct cctctgccta cctccaagcc atccatcaca    112800
ggacagctca agcatcagat cctctgggac actttcctta gttgttcagt ctgatgaggt    112860
gtccctcatc ctctcttagc tgaaaatcag cagctgcctc aacttctttt ccagcatgtc    112920
tcatgagtat tgccacaaca gcatctgtca caatgtgggg tagtggctga cttgcttttc    112980
tgccattcaa ctgagttccc tcagtgctgg ggccagcgtg cagtgtcttg tattcagtat    113040
atagctgatt aattgatgaa ttgattaatt aatggttcac actagcacag tgcaaccttc    113100
aatgcaaaga tctcatcaaa ataattcaca tggtgggata ttttagaagg atgaccaggc    113160
tagtttgtag taagaaaaaa tcaacaagac taggtcagga attcttttttt tgtctacagg    113220
cttgctatag aagatattga aaatcatcta cctaattacc tttatttttat caggttgtgt    113280
attaaatatc acgtctgggg gaagaaaatg tgatatgtga ttacagacct ttcctggtac    113340
aacatagtac gtttcagatt aactcaaggt attgtggtga tattgcggtc aaagccaggt    113400
gattaaagag tcattctttg aaacaaatat ctgtgcaatc aattaagaaa ttaatttgca    113460
aattttattt gcttagagta attgatatat cattccttttt acaaacaaat ataagaaaa    113520
cttaactaaa aatactgcat atctctttca gattatatat cccagaaagg atatatttttt    113580
ctcctttctg gtcttccttt ttggtgtagc atctgtagga aatgcatttc ttcatagcta    113640
agtgtacctc cttgtgaaat atcttcagag tctactggtg cacataagca attgctggca    113700
gcagcttgag ggtctccatc tcacatttat catatgcctt attgcatgag gctttgcaag    113760
aggaggtcta gagctacaat atctcatgga tatgaatgtc aattcaaatc ccagtggcag    113820
tttatgaggg ggaaagccta gaagagaaga aacctagagg aatcaagcag gaggggagag    113880
taataaaaga ctagagcagc aggttttttct taactcaaac tagaattaaa tctctgtgtg    113940
tgtgtgcatg tgaatgtgcc cgtatgtgca tgcatgcacg tgtgtaaatg gatgtgtgtg    114000
tgtgtgcatg tgtgtgcaag taagtgtgta tacgtgtgtg ggcatgtatt gtgtacatgt    114060
atgtgtgttt tatgcatctg tttgcaagta tgtgtgtatg cacataaaag tgtgaatgta    114120
catgtgtgct tggtgtatgt gtgtgtatta atgtatgcgt gtagttctag agtctagtta    114180
gagaaagtgc ataagaaat agggaaatta acaagaaagc tatagcttaa attataggaa    114240
aaacttttct ccctatcagt catggtttta aaatgttcag acttgatatg tttcccagtg    114300
ctattgtcag aaaatgtccc tatgacattc catactactt caatcaaatc taaaaccttt    114360
gttccaacat gttttattga tatgagtata tttcaaattt ctaccaggtt tttggagagg    114420
```

```
tattttggcc ataaaattga ctaaattatt caaaataaaa aatgaataag cctgggccaa 114480
ggcttggaga cttgcttaac tcagttctta aattttcaga ttttcaaaat tacaaattta 114540
agctctaaaa tcatggtgct gtgtatgata ttctttgatt gcaacttatg gttgaaaaac 114600
tatagagggg tttatgctaa gagttgtgga tcttaggatt ttcatgaaat ctgcattatc 114660
atcatctgca agtttagatg gggcataact gatccaaagg atggatccct cgggggcaat 114720
tcaactggct gattccagcc aagatgacaa cagtcaggat ccgttccctt ctgatcatcc 114780
attgggtgcc ctgatttcct ctacagccct agctgaaaga ccagacacta tctcaggctg 114840
gctgccccac atgccttgct ccacaccaaa ttcacagtct ataaacctga gcctccagtg 114900
ctcctactac catactcact cgaacattcc cgattctgac ctggagatgt caacagctac 114960
ttgatgccac tctcttctat ctttctgtag ctaagccatc cccaagtttg tcgattcacc 115020
ctctttaacc cctgtcgggg tgtccattgt gccccttcac cctgccatct ccctggtgca 115080
ctgttttgca aagttcagca tacatgagcg tcacctggga accttaataa agtgcagatg 115140
ttgattcagc aaatctggga tgccctcggg ctgcatttcc agcaggctcc tggggatgtc 115200
cccgctgctg tgctgcagat gacactctca gtggtgggac tccaggctct gctgtcgcct 115260
cctaggggtt tctccacact ccctggaggc ctaatgggcc cttctccaca tggcagtaag 115320
atctgttttt gtgtttgtgt ttcaagttgg gagaaggaga ttatttaata ctaaaatgtg 115380
caacatggga ttgagaaaac taattattag tcataagttg agtatgcaac attgaaacca 115440
catgctttaa aaaattataa gaaaaaatca tagtatttga agttacaag ctattatggc 115500 taactccatt tatctcagtt agagaagaag agtcacctgt caccagggca ctgccagaag 115560
ccaggctcat ttccaacagc actgggtgct ccagctttgg ggtgccagct cctcccataa 115620
agcaaacaca tacctaggga tgatatttct ttgcaagggc tctgccctac agcttgtaca 115680
tctcaagaag ttatgtaatt aaactgtctg ttttgagaaa attgtagatt cacacatact 115740
agctgtaaga aatgatgcgg ataaatccag cgtaccagct ttccccacgg agacgtcttg 115800
cagcgtcaca gccaggatga ggcattgacc caggcgaagt ccagagcacc tgtgcgctac 115860 agggccccctt gcactgtgct gtcacagaca cgcccacttc cagatgccat ctaggacccc 115920
ctccaaaaag cagaggcatt cttaaaaaca cacatctgca catgttcctc ttcatttgaa 115980
tctgtcagtg gcttctcagt gccttttcaaa tgaaatctaa agtccttaca agccttgcag 116040
caggaacctc tccatcccac ttcccctcac actctcagct tcatctctgc taggctctgt 116100
tcagccaggc agcctttcac agtccctctc ctcctgccct gccaggaagg tcccctgccc 116160
ccaactcttc cccacatgtg gcggggcccc gcttgtcctt agaagcccag ctgaactgct 116220
tcctgaagga acccctccag aacctctcag accaggtcag gtttctgcac tcttagatca 116280
tccccatggc ataatcacag ttgtgatgtt gtgatgattc agtgaatgtc tgtctcccca 116340
ctggatggta agcttcctga gggcaggaac agcattggtt ccagtcaatg ctatgtccca 116400
ggactgttcg ttttttgcaca tactaatcct aaaaggacga tgacaacagc aaccacttac 116460
atgacctaga tgctcttctg ggtgttgtgc aaatattaac aatttaatcc ttgcaacaat 116520
ccacgaggga ggcattcttc tactcccact taacagacaa ggacagtgaa gctagtaaag 116580
agaagtcatt tgcccaaggg gacccacta ctgttggcag agctgggtgc aaacgcaggc 116640
ttgtgaagcc aggacccatg cattcaaaga ccatgccagg tgcccccact gcacacctca 116700
tccccacata ccagtgaggg ggagagaaat gctcctgcac tgcctctgat taactgcttt 116760
cctagaagtc acacatataa aagggattta attctagtgg gattgaatct caatagtttc 116820
```

```
cttattaggt tgatttctgt taatagttta agtactggat atacatgaat tagaaaatct   116880
agattattag caaatgcaaa ctataaagta ttttataaat gttatcttgt ttgtcagggg   116940
atgagtgaga tattcattat acaaaaagta gtgtggattt tgaggtagaa ggtttactaa   117000
ggatcatacc gtagtatgaa atagccacaa acattcagtg aaaccaaaca cccccgctta   117060
acctcaaact aacactaaat aataaggaat agacttgggg gcagtgcaag tgtatttcta   117120
atggtgaaaa ccattcccca gtgaaaacta atgtaccatc tagttaataa gagctcctct   117180
gacccacgca catcaatact tacatcccaa tggtgatgtg acattttggg ttttgtattt   117240
cttttgcaaa ttgagctagc attttttgatg agtggcaggg ctctgctacc caacctttgg   117300
acagtttcca agcataaaat cacaattcca gataattctg tcacaaagat ctgggtctca   117360
ttaggaagga gaggaagctg ggagatgatc cagtccaacc tcccccaaac caaacatcac   117420
ggccttctca gttgtttcac caaccatcta aatgttttag taattctaaa aattgatgcg   117480 cttttttccac gaaaggaagt gttaccacat tttccaagtg ggaggcatct atatccttac   117540
tccttcatcc tctccttccc accccctcac cccccaccac ccacacaaca tctgcaattc   117600
ttaaactaaa gcacaaattg ttacaaaagt taattgcact ttcaaaggaa tgcttgtata   117660
gaaactttct cggcttcaag gaaaaataat acgctttgaa tggctgttca acagcataga   117720
aattagctga gtagaaggca ctcatatagc cattaggacc aatcctttct gccgccaaca   117780
ccccccttat aaagacttga cagtgggcca gaataaacaa cttcaggatg aattcagttg   117840
agacacaaag tacacacttc cagttttttcc cttctctggt tactggcctc aataaccagg   117900
cagtcaactt aaaaagaaaa acaaaagctt gcttcagatt acagattgca gacttcttat   117960
aatatgtcca tttcaccagg ccccgctctc agccccggga aaggccactg gaaaccacct   118020
cacatggtag ggccttgcgg gagccagtaa taaccttatc tccgtcaaca tgttctgtca   118080
gattgaatgg ggcagccaga gaagccagag ttggcacagg aaccaaaaca aaggcttccc   118140
atcctcctgg agtgagcggt tgagcctgga ttggtgctta gacctataat gggtgcaagc   118200
agcgttcatt catagtggct ttctagaccc agggacttgg ccccagccct gctgctccac   118260
tcctcttctt gcttcattac cacgagtctc ctagaccacc gaacgatgcc tgcatttgaa   118320
agacacttct gctgatcaaa gcagctgatg tgtcccttttg cggttcattt ctaattgtcc   118380
ccaaggagga gaaattcaaa tagtttatta ctgagagtta agaaatcca ctgaaatatt   118440 ctttggtcta aaattactgt catggcggag cagcttcacc ttagtcattg cccttaaata   118500
tgaaagctat ttaagaaagt ttgcccttaa atatgaaagc tattttaaaa agttaatga   118560 aagaagagaa tcacaaaaca ttttcaaaaa gcaaagaaa acctaagaga aaagttgaaa   118620
gtaggaattt tttaaagaat atcgacgtg tgttctgtga ctcacccctg caagttattt   118680
gtgtgtattc ccttgcatag taattaataa tgaagcaaag catggcaatg atatcttttc   118740
ttgtctagta ttctagaaga ctccatgttt tggaaaata tcactctagt tagatctcaa   118800
atatattcaa tcagaaaatg ggttttctac aagattctat atctgtagtc aatagcaaat   118860
ataattctat taagctagta ggatgtgata ggaaactaaa acctagggga gaccaaagca   118920
aggaaaaata cttcctcatc caaacttgag agcaatttac cgtcaggcct actattaata   118980
gatggaatac agattccatt ttcattactc aactgccata ttcattatta cactgtacag   119040
aaaagggaat cacatctgtt gaaaactat atatgatgtt catgcatgca ttccagtaat   119100
tcaacaattt ttatttatct ttttattgct tgctaatttt tcaaaataat aagctaaaga   119160
```

```
aaacaaaatg tttgtgctgt tctcagatga catgttatct ctttaaagga caaaatgtgc   119220
tgtgaaataa tagaatgctt tcagcactca agtgtgagtg agtgctcata catgagagaa   119280
agccgtgggg actacagaag ccaagaagca gatctagctg gggaggcctt tgcagaggat   119340
gtagttgtgt ggagaggcca cacacgtgga attcccagga gggctgtgga ggcggggaat   119400
ctgcaggaaa gcactggggt gagaaacgtg atgagaaaca attattgtct taaaatatct   119460
gcagggctgt aaggtagaga agcaatacgt tgcatctgtg ttaagtcaaa caaaattatc   119520
aagggactgg tttcagctta acataaggaa caattatgtg atagggttgt caataacaag   119580
agtagactgc ttcttcacac actcctagtc actcagaatg gtccaggagg agtggacaac   119640
catttggtag agtatgggaa ggcaggggcc ctgggtggga gtggtgaggg tagggagtga   119700
gtatcccaat ctagaagtaa attgtgccca gcacggagct gcaacactgc cctgcacaca   119760
aacacacaca ataacaatc cccagcccct gcatttccct ctccggtttc aggaccttgt   119820
atcttacttc aattccttta tttagctgat gatgaaatag gaagagctta gcactaagaa   119880 aatcctttg gagtttggcc ttgggggaaa atgaatcact ccaaccaggt ctgtcttcta   119940
gaaagtatag gatgaaaggg ctcctcatca catacttcct gacctcctgc taggcctttc   120000
cctaaaacag gggctggcaa agcacaacct gtgggtcacg cctagcctgc cacctgtttt   120060
tgcaaataaa gttttattgg agcatgacta tatgtatttg cttacagtct gtggctgcgt   120120
tcacactatc ccagcagagt tgaataattg ggacagggac catatgatgg gtgaagctga   120180
aaacatttac tctctggctg tattcagagg aggtttactg agcccttctc tgagacatgg   120240
caagcgctgc ttcaggctca tgcttcacta gattcaggcc tggggcagta aagagccagc   120300
tcaggatagc actcccgact cactcatttt ttcaggcagg ggagccatct aatgtcaagt   120360
gcctacgtgc aggaactggt ctgttaatta gcagctctcc tcatggaagg gataatatat   120420
tctagaaaca ggagtgcggc cctattgcaa gaatgtcctg agccaaaatt aagattcttc   120480
tatggcagaa acttggctgg ggcttctcct gagttaactt ggtagttgtt agtgattttt   120540
gagtcagttt ttccttgtca acgaccccag gaatgagttt gggattacag ggtagccagg   120600
gaaagggaaa gcttcacgcc cgcccccggg acaaggtctg tcttcacact gctacatccc   120660
ttcacccact ttaaaatgaa acttaaaagg aggatttcag ttgagtagga agtgagaaga   120720
gggctcattt taaaacaagc gttaaatgaa acccacaca cactcagagc acacaaatcc   120780
aaccacgctt acaaaaccat cacagagggt caggcgaggc ccttttctaa atgaaaaaga   120840
acaggggtgg agactgttct gagagcatgc tgggttccct gaagggaatt ctcagctgta   120900
tgtgccccgc acaggatccc tgctagacac aaggccagct gccttccttt caagccgcag   120960
acgcatccct gtgtccaggc gggctggtca gctgcggtca gcaccagctt ccccgctcca   121020
tggtgaggtc atcacaacat gtgagcagga gggcaggccg gcaacctctg agtgcttaga   121080
gaaagggacg ggattcctcc tgtgcaaccc ctctagtctc actcagactc aagtctgact   121140
aaggggccag gtgctttgac cagggactct ccctctcac ttccctccca ggagtcacag   121200
gtacatgagt ccttgtttta caaatgaaga aaacagaccc aacatgatta agatgttgcc   121260 ttcataggg tggcaccagg attccaaacc atggactcca ctgagcccag tgcccactga   121320
catgtgccag taacagtgca gctgcctgtg ttctgtcga ctaaactgcc ggcagaggct   121380
ggctttccac cttctttttt ttttttcac tcttcaaaca ctttatgaca tgaacataaa   121440
ctactggctg catcgttctg ctgacaacat gacatgtttc tataacttga aaaagcaag   121500 cagtggactg ctcattggta aaattgagtc agtaatcttt taggaaggtt atttttcttc   121560
```

```
cttttactgc ttctcatctg ttccccgcag taaagaggac aagatgacga cgactcaggg   121620
aacacctcca gcctgaagca gcaccatgcg agcttagacc ttagggtcgg cttagaaacc   121680
acaggcgggg cggcttgggc ccctcggaca ctccctctcg aagctgcttc tccccaagct   121740
accccaaagg cactgagcgc cctctgcccc ccagcaattc aattcactgg ctgtcctgct   121800
cctgtcagta ctgagagttg catgtttgac cctcggggga aaagtccaga ggccctgggg   121860
tgtccagcat gctctgaggt ccctgctgct gaccccttgc gctgtcagca ttcagagaca   121920
ttcacacagc acagcctccc aggctaacag ctgtcatgga acagtggagc agctagacgt   121980
ggccattctg tgcccagtg ctgcagaggt caaagggaca agcgcaggga gcatctttgc   122040
tttcagaaaa aaaaaaaaaa aaaagaagca cactggtgca ctgacctgct cctggtgtct   122100
ttgtgattgc tcttttcttt cgattttttgg ttgtcttttt tttttttgaaa gaggggcttt   122160 tatgctttt tcctaatgtt catgggtaaa ccaatgtaaa tgtgtgtatg tttatagaga   122220
tggctttaaa tcgcaattct gcagtagaga ttgattttt aaaaaacatg ggtaaaaatt   122280 gaagaaaat tttaaaagaa catttaaacc atcttgggct aggggtggat atgcaccacc   122340
ccacggaagc caaacaaaat ctctctgcag ataaacattt gcaaaaagaa tttccaatcc   122400
caatttttga gtcagagatc ttttatttcc ttgcaaatta catatctgtt tcaggatttt   122460
tgactataag aagaatgaat gaagatgtgt ttcttacaga taactatgaa caaaccagga   122520
aggataataa cttgtatccc ccaattcgaa tccagaggat gggaaggcat aaaaaaaaga   122580
aatggaagaa actttatttt tagtggtaaa tggtgggact atgtatttta cgtatggtga   122640
agtcaccaag cccaacactt ggcacttgta ggcaaggtag tcttctaatc tgaatgtgaa   122700
gtattatgtt ttcatttgct tggtaatgag gaatattggt gctttcgtcc cagttctcga   122760
gctgactgac ttctctttct gacgtgtgtt cctttagcac acctctacac tgcatggctc   122820
tgagatgtcc tgtgactgtt tcatgtgtaa agttgcctcc ccaaaggact cacatattcc   122880
ttcagggcag tgagtacttc tgattcatcc ttagcagcta ccttcgcgct actttactag   122940
atatgttgta gttgaattaa tgaacaaaag aacaagcaac tttggtgcct ggtgtgcatc   123000
tcagagcagg gtggagtgag cctggccaaa gggtcatcat gcaacctctg tggctgactc   123060
catctggcca cggagcttct cagccatgct tggtattcac atgacttcta gggcgacagc   123120
tcaaccagca aataaacagc ttcatatggg aaatattact cagcctttgt catcaaggag   123180
tgagtcacgg gcctgaactg aatagaagat agaggagaaa aggtgtgtgg actgggtgag   123240
acagcgccca gcgaggtgaa ctcccggcag ccctgcctgt cttacctgc acatcacctt   123300 gctagggtgc cttcggttgt gagggcctgt ctaggaagag aagagttgca ccctggcagg   123360
cagcactgag ctgtctcatg caaagctgag gaagaaagag tgagctgccc agtgagcctg   123420
ctggggtggt ggaggctggg ctgggctgtg cagtctgcag cccccagcag cccttggcac   123480
ctttctactg cctggtgctc accagctctc cagtaacaaa gagggacgtg aagtcagagg   123540
ggaagggagg tagcacaggg cagtcttgac tttgaacaaa gagctggctt cctgaagtca   123600
gctggccggg ttttgaagcc gattttccag cagtgatctt tgatgccaac cccatttagg   123660
aattctgtat ctcccctac cttctaccag atgtctctga gctcacctt ggtgataatc   123720 atgcaatctc cgtcatcccc acgtccacac tgccccattc tgtcccaccc cgggttctgt   123780
ggtgctgtcg gctccccagc gagccaggaa gggagaggcc agctctgctg gggctcctgc   123840
cgccctggct ctgcactgcc cttctctggc aggtctgagg cgccactgga ggagccacac   123900
```

```
ggccctgaag cagcaaggca gatgccctgg acacagtgga ggcacagagt gcaagcaccg    123960
gcctggccca cagactttg gagggggaagt ggtattattc agttcaaaag tatgcctgtg    124020
tgtaaagaga gagcccctga acatgagtaa gcaaaagtct cagcgcagag attagacaag    124080
tagaatgctg gcccgagagg aggcgtttac tcaccctctg tctaggaagg aaagccaggc    124140
ccagcacgct cactgctatc tatcctctca cacagaggga ttttgaatcg aagccagcat    124200
cctgtccttt ctccaatgtc ccctgctcag gagtcaggac tcagcaaggc ccaccccagc    124260
cacacacaga tacagttcca ggactcagaa ctcagcgagg cccaccccag ccacatgcag    124320
gtccagttcc aggattcagg acacagtgag gcccacccga ccacatcca ggtccagttc     124380 caggactcag gattcagtga ggcccacccc agccacacac aggtccagtt ccaggactca    124440
ggactcagcg aggcccaccc cagccacatg caggtccagt tccaggattc aggacacagt    124500
gaggcccacc ccagccatat ccaggttcag ttccaggtaa atcatctgcc ttcctccgtc    124560
caaaagcctt gtttcctgtg tgtccttgtg tttaaaatgg aaacgttatg agaaactgcc    124620
tgccagggca aagggtgctg cccggcacac agtagggact caaaatgaaa ctattgtatt    124680
gaatacataa cagatcaacg ggtattgctt tctgaaatct tttttagccc aattttgttt    124740
cttatagtcc aataacaggt caaattcatt tctgatttac tagccattca gttgcccata    124800
aaaaatggaa agtgatttaa gattattagt ttaaaaacca atgaaggtaa aacagttatc    124860
attgaaggca cataggcaga aatagattgc aatagttgct gccatgtgaa gcctcagtgt    124920
catgctccat atttagagag atctatgatt tctgaggccc tttcatgtcc atgatctcag    124980
tactgctcac aactgccctg tgaaattcgc cgagctggcc ccatgtcaat cagagtacac    125040
tgagcactga gacccagcat gttgagataa ctggctagag atcatcccat aatggtacca    125100
tcacaatctt cacactgtag aagtttgatg atgtcactgg aagcatattc cacagtccct    125160
tgtgaactgg ccttcctgtg atcagaagca tcagtgaact cccaagaggg tgggaactcc    125220
caagaggtat tctcactcta cttagtgtat attttacaaa tcacaagctt ggctttggat    125280
tcttttaatg gctagaagga gaatcatggg gttggaagtc caccagtttg ggtattctgt    125340
tccctaactc aaaataaaga gatgttattt tcaagtcttc tgcttgttaa cttaattaga    125400
gatacatgag tttgcagctg tgctgggcat gccgcagctt ggcatgttta gtccagaagg    125460
catattataa tgtacatgga agattgtcag aaattcaaaa ggactttttg agtatcacat    125520
gtgtattttc aagttccaat atagattcac attcagtttg acaggtatct ttggatgcct    125580
atcagttaag aactatttat tagttgtgga ataaaatagg gtaaaataag gaacaactga    125640
ggaaaaaaca taaaatttgc tttgtgaata aaagttgtct tcaaaattat gacttttcc     125700 atcccacaaa agttttgatt aaacccacaa tgaaaattta aataagtgta tttactttgg    125760
tttaaccact tatttcatta tgactcacaa ctataggttt tctagtttcc attattacaa    125820
actattgtgt ggtttaaatc aatttcatag actagtctag ttctatagtc acaatttata    125880 aaatttttt atgtggtaaa ttgagtgtct tcatagatgt acatgattat ttctcaattt     125940
ttaaggaatg tattttttaa gatagccttc tttagccttc tttaacactg attttttgtaa   126000 attttttaca gatttttta aatttttggt aatttttag cataaagtaa tacatggtca      126060
ctatggaaaa cataaaaaca caaaaactat gaagagtaaa taagaaaaac acccagaaat    126120
ttaccattca gaaaaggtca ttgttaacaa cacggtgtat cttcctcctg tcatgcttcc    126180
gtgcatttga gcacatttga gatgtgtata catgttcact ttgagatttt agtatagcaa    126240
aagaaatgac cggtcctgat tcaatgaaac ctctggcaaa ctcgctatat tttccttaca    126300
```

-continued

```
tattttttaag ttcatcctat aaatgaacta tccattcatc ttatttgaga tttttcttaaa 126360 tctttcagca agaaagcggg aaaaaaatcc tcctctggcc tttaaagcct aattaaatat 126420
atgactaagc tagaaatatt ttataatgac caaccagaaa gtggcaagga ctgtcactct 126480
tcccatacag cccacctcct cctctatctc cctcaggcac acggaaacga gaaaggcaga 126540
gaaacccagg acaagtcatc caagactttg gtcacatggc catccattgc tttcacaaca 126600
aaaatataaa tccaacatgt gtgtgtgcat ttcataccag taggtccaat aagctatcta 126660
tatatacaca tatgtgtaca cacacacaca cacatcctta cagacactcc ccagcttact 126720
acagtttgac ttaagatttt ttgactttac gatggtgtga aagcaatgca cattcaatgg 126780
aaaccatact tctaatgttg aattttttat ctttttcttgg gttagttgat gtctgatatg 126840
ttactttctt gcgatgccag gcaatggctg ggagccagag ctcccagtca gccatgcaat 126900
caagaggcta aacagctgat actatacagt ggactgtgtc accagcattt tggggatatt 126960
gtgttttgtg ttttttgaatc ctatcatgtc tacaaaatgc catttttcgac tgctattttc 127020 aatttagggt gggtttatca ggacataacc ctatggaaag ttgaggacca tctgtatatc 127080
tggtagggaa agatggataa caaattcata ggcaaataat aatttcatga ttattattaa 127140
gttattccta cttaataata agtagtgatc actgccaggg agcagagaat gcaggataat 127200
gtgacagatg taatggtggg tacttaagct aatgtagttg cagaacaggc ttttctagag 127260
ggtaggcctt taagcgtacc tcgaagatgc aaaggaagca aagatgcgaa gatctgggct 127320
ggggatggaa gcagagacaa cttggaggcc aaggggagag actgacaaca gcccagctca 127380
tacctcagca gcctttaatg catagctaag aaaacaacaa attaaaacaa ttatagttta 127440
cttagacgat tctaagtgtc taagtggatt tgggcaaatc tggagaaact tgttctaata 127500
ctgtgtctta ataagtaata tagatttgcc caggcttgtg ggcagagtgg tatacacccc 127560
ataatagcag aggaaggcca cagggcctac cctacaaaac cagaggcatt taaaaactta 127620
aaggaggcag attgctttta ttttcagtta aaataaagtg aggagtttct caagaaaaat 127680
aataacgaga ccaccggccc gccctagatg tccaacaaga atgcacagat aacttcgtat 127740
atccactttc ctgaacctgc ccctgacagc caagtggagc acaacaacag agatgaacct 127800
caaaactact gtgctgtgac ataaggcttg ctcaagagga cagtgtggtg tgagtccatc 127860
tatgttctaa agcaagcaaa gctattctgt agtgaaaatg gatcaggaca gcagttgcct 127920
ctggtgtatg ggggcaggga tcgactggga ggggcatgag ggatgacagt tagggtttcg 127980
atcatgacag gaattcagat tactccagca tgtgcatttg ttaaagctca tcaaatgcta 128040
cacttaagat taatcctctc acagtttgtg gatgttacct taaaacaac aatgatgact 128100 gcaaactaat attgaactct ggttagtgat ataccaatgt gaagtatagt gatatctcta 128160 ctttactttta aaatgcatcc aaaggcagac tagaggacca tatctgacag acagaaaaat 128220
agatatgtga taaggtgaat gtagtaaaat gctaacataa ggatgttttgc ggtacaattc 128280 tttcagctttt tctatacatt tataaatcat aataaaattt taggacaaaa agttagtgct 128340
ttgaagtcct aagtcatagg gcctgctgct cttgatgcag tagaatttgt cttcagatttt 128400 gcaaagggta aggcaaacca ctagcatttt gtatggaact tgatgcaaat acttttaatt 128460
gtctggtttt caaatgtata gacttaaagt aatatcaact ctttctttga atcaactact 128520
gaaataccta gtcttaaata aatatttta tgtaatcctt aaagtactat gtattcattt 128580
ttctttcttc tttctttttct ggtttgataa atattctata aagtaactgt gtttaatggc 128640
```

```
caacatttga gtaagtccat atgcagatcc aaacatctca gtttagacaa taacttaaga 128700
caatatagag tggctgacat cccctaacgt gggtccagat gcatgttatg ttatgtttct 128760
gttgcattct caatagttaa ctttaataaa agaaagtcaa aagcttatat attttttcaa 128820
tcttcaaaac atttctggga ggttgtctta gttaatttta tgttgctata cccatatcac 128880
agactgggta atttataaag aaaataaatg tatttggctc atggttctgg tggctgggaa 128940
gtccaagagc atggcattgg catctgcttg gcagctggtg agggccttca tgctgtgtca 129000
atctatggtg gaaggtcaag agagcatgca tgtgaggtgg tggggaagag aaaaagcggg 129060
tttaactcat cctttatca gggactcact cccgtgatag ctaacccatt cttacatgaa 129120
tggcattaat ccattcctta gggcacagct ctcatgacct aattataata cctcttaaag 129180
tttccacctc tcaacactgt tgcattggtg attaagtttc caataaacgc actttggaaa 129240
acacattcaa accacagcag agatcaacgt tattgtcacc attttcatat ttgaggaaag 129300
catggcacag agagcttgga gaagtacttc aaggtcaccc aatgaggaag tggctaaaca 129360
aaaaccttat cttaaattaa ttaaaaacct cttgctcttt gcagttttgt cttaaatcta 129420
cctaatttgt gactgtaatt tttaagtaat ttactcatat aagtggtctc acattaaatt 129480
ttctcattgc tttatatttc taacatgaga tatttggtat aaggatggaa ccaagatcat 129540
accttgtttt aattagaaaa cctagaccaa gtcattgtga tcctcatcct agatttcagt 129600
taaatgctgc tgtctccttt tgggtatgtg acagggaaa gcctcagaag aaacaacctt 129660
atgtgttttc ttttgatact ttagtaatta acccaggata gtattcaaga ttgacatgcc 129720
ttatattgaa tcaaatagca tatcaactgc cttcttattc tcaagtatag acatgttggg 129780
taattgggca tttaagtttc tttgcaattt tttccattat taacaaaatt aatgagcaac 129840
attctgcata aggtctgttt cctcagaata cgtttcccaa agtggaatca tcatgacgta 129900
gaatttaagc atacttactt gtttaaacaa attgtccagt tgcttcccaa aatgttttgt 129960
gaattaagat ttcatcaag aatatgtaat gttgttactg tctcccaaat acaggatctt 130020
tttctgaata taaaagttat acatgctaat tgtagacaat gaagggtcat tatcctcata 130080
gataatgaag tgcttctaat acttgtgctt ttattcattt attcaaaaag tgctaaataa 130140
gccctgaagg ggcttttggg gggtcatttg gggcttattt agcactttt gaataaataa 130200 ataaaagcac aagtacagtt ttttaaaat actgttttct ataatagatt aatcttaaat 130260
ggcatgtttt cctttatttt actgacaaaa gttacttact ctgtgattga ataataaaaa 130320 ttcttttggtt cagctgagag aaacttgcaa gctgacgtcc ttgattattt aaaatgaaag 130380
cagctgcctg ttttcatctc tctgcatcct gaggaaactc ttctgcaacg tgttccagcc 130440
ctaggttcta gctgaccctg ttcatctgtt tggcacgagg ggcccaacta acacttgcgg 130500
ctacctggac gacagccaat ctagttggaa tgagagttag aggccatagt ctgtcagctg 130560
ggaaagcagc ttttattcca aggtgtgcca accgaaaggc cacatgttat tgtcacaacc 130620
tggtacctac atcagtgctg acatctttaa gaaccttaga attgggaaat cagtttagcc 130680
ctatctgcat gtgtagccga caaccacaca attgttccaa cttgaggttg cattcagagc 130740
aacctcattt cccccatact cctgaggaaa agcagaccag agacgctggg tcaatccaga 130800
gttatggttg gaaaaatgat ggaataattc tgcccctggt gataggagag agggactcca 130860
tcttgtcaac tgtcatggtt cccatgtgaa agctatcatt atcactgaaa ttgaatgaga 130920
acacagaagg gaagaacagg gaaatcccca cagagttaaa gaggatgtga agattgcttc 130980
atgtttaatg tttgtgtaag tgctttgggt tggttatgtg ctgtctgaac atgtgctcat 131040
```

```
ttccatggct cattgagagg gcagacagtc caatgatact ctttagaatc attcccatgg   131100
ggaaggaaca aagaagcctg taaaatagaa atgcacatgt aaaaagcatt gaagaaagtg   131160
ccagtgtatt gattttggcc atggtttgtg ctctaccacc tggttactgt gattgcagaa   131220
gtgcctttgc agatgaggaa gaacctggcc aaggctcaat ccaacatcca aagccagagg   131280
ccatatttct tcactcttaa gataatttgg gttcaaatta tagtcccttt acacactctc   131340
tgcctcaaaa ggcccaagac tctcttttgt tatgcttgcc taaacatgcc tttcaaagaa   131400
ctagttctgt aaatacaact ttattataaa cctctccttt gcttttaaaa atggatcacc   131460
acgtccattt ctatggtcca actttgtccc ttaatttaaa attttttctt ggattaagtt   131520
tgatgccttg aaacattagg aactcaagca tacaagattg tatgctggtg gtgagggaag   131580
taactgtgcc tccgcctgtg ctgggtggat caacatggag tgtggacgag catagggatg   131640
tgtgggtttc tcactagctg agagtgtttt taaatgttgt attttgatgt ttgttatttt   131700
ctgaatattc tacagttaga cctttgattt attctttgat gcattcattt gaataatatt   131760
tttaatctcc agccagttag gttttttaatt tacacttttg tccctgattt taggtgtagt   131820
gttgtgtaca ctactgccca gtgtatgtta tgtttgtaaa cattcattgc acgcacaaca   131880
atgtgactca caatatttttt gagaagtaaa aagttcatta tatagttatt aactcaaccc   131940
tacagttata ttcgtgaaat accttgtgaa attttatttttt tgcctactgg agctcttaca   132000
ggttaatcct gtcttcaaga tttttcataga attttcatct accacccacc cctttaaatt   132060
tcaacatttt tttattttggg cattttaatg caattcaatg cattataggg acaagctatc   132120
tcttattatg aattgcacct tatataaact taaagatctt ttatcacaaa tttctttgct   132180 gtgtcccttta gtgagaattt gtattatcag tcactaaagc tcactaagtt agtaagcttt   132240
gcgcccagat gacctgggca ggaatgggtg agtctctgtg tggagagagt gaagaaactg   132300
ctacccttaa tacctggacc ttgagggatt gttttatttt agttttttctg catttctcag   132360 tatttcatgt gatatctgtc tttttcttcc agtttgccaa ggcacgagta acaagctcac   132420
gcagttgggc acttttgaag atcattttct cagcctccag aggatgttca ataactgtga   132480
ggtggtcctt gggaatttgg aaattaccta tgtgcagagg aattatgatc tttccttctt   132540
aaaggttggt gactttgatt ttcctacaca aataaaattg gagaaaatct aagtggagaa   132600
aggcctgggc agaattccac ttgaagtgtg tttattttttg ctatggcaat gacagtcttt   132660
acagagctac aaacgagagt tttatgagaa agccattttta ccagctaatg tcaagtaata   132720
actagaaaag gatatcaaat agaaacaggc taatctggaa ttccatgtca tcatagacac   132780
tgacgtttat ccctgaccat tacctcagtc atgatgtgct gccatactcg ctcttaaaaa   132840 cttttttttaa aagccctgct ttgcaccatt tgcctattcc cttagtgtaa atactcctac   132900
tatagctgat ttcaaggtac caagtttcac tcagctggtc acagaattct tatttcacga   132960
taggcgctaa tgaccccata ggagccagct ctgaaggctt cagagtttca ctgaattttg   133020
gatggggttt acttagcctt cttctgtttt tcttttacct ttccttttta ataagaaat    133080 aatgcaagac agatacaaag taattctttt taatttccat tttcactgga gagtgttgaa   133140
ccccgtgagg catgagagca cagtgttcca gaacaatgct tactgctcat tatcacaggg   133200
gtcaaaggct aacgtgcagg gattgttgca gatcgtggac atgctgcctc ctgtgtccat   133260
gactgcaatc gtctacctat tttacagttg ttgagcactc gtgtgcatta gggttcaact   133320
gggcgtccta gggctccctg gacccatttt agaccttgag ttcttgagtt cctcaaaaga   133380
```

```
gaaatcacgc atttatgttt tctcttctta gaccatccag gaggtggctg gttatgtcct   133440
cattgccctc aacacagtgg agcgaattcc tttggaaaac ctgcagatca tcagaggaaa   133500
tatgtactac gaaaattcct atgccttagc agtcttatct aactatgatg caaataaaac   133560
cggactgaag gagctgccca tgagaaattt acagggtgag aggctgggat gccaaggctg   133620
ggggttcata aatgcagaca gcagttccga tggctcccag cgagcttgtc actcaattcc   133680
acctcggaga aggcttttat ttttacccag tacacgtgca ctgagtgccg gctgtgtgta   133740
agatactgca ggggaagtta ctgagaagat ggcagatact ggaatgggaa gatttaagcg   133800
gggtaccagt gtttacatgg acatgaaaaa atactgagag atagtaagaa atcgtaaaga   133860
ttctgagtaa aagagagtat gaccaaacaa gctgagcagg aatcgtgaat ctatgtgtgt   133920
aggcagtgaa taaactgcca gtcttattac ctggacctca aggataaaag acatacagta   133980
aaaatcaacc cacattgagg acagtttcga gagtcgcgct gctacacaga aagccctgtg   134040
taagttaagg atagaaatg aggtgttcta gaactttgaa ttttgtgag caggactcgt   134100 gaggttcctg tgagaggaaa caatgaagga tgatagaaaa gaagggaaat tgattttaaa   134160
aaactggaga tagcagtgat tgtgcctcac tgtgcagtgg gtttggggcc aggaatgtta   134220
aattggtaac ttcatttaac gcccacaacc tttcttcaaa gtaggcactg tacagatgcc   134280
ccttgactta tgatggcatc ctatctggct ggaccccgcc gagggtgaag gcgtcattag   134340
gtcggatttc agggctaatt gaatgtatat tgccttcaca ccatggcaaa gtcgaaaatc   134400
tgtgttaaat catgctaagc cggggactgg ctgtgctctg ccatcgtaca aataaataaa   134460
tggaagtcaa gtaactccct tgagggcccc agctagtgaa tggagaggcc agctatggcc   134520
accactctct gccccagggc gctcaacgcc cctcctgtgc catgcagttc tgacagggag   134580
gcagtgctgg taggaaaggg gtgtgatgaa agggggtgccc agcagaggga gtcatatccg   134640
gagtgacagg agcccaacag gggtgcagcg ctggaaccca agccagcacc tctggtcatg   134700
gctcctcagt tcaccgccta taaaattgtg tggttccccc acaccccttg ctgctcagag   134760
cagccgcgca catgcttgtg ctgtgcgtgc ctcctgtgag atggcctggt acaccggttc   134820
ctacagtgcg cctcacacgc tgtctcggag ggaggcagcc tgtgcgggtg cctggacctc   134880
cgagccagac cctctgggtt cctgcctggc cccgtccctc agcagccaga tggctcggga   134940
gcacattctc caatccctcc gtgtctctgt ttcgtcatct tcaaaaatgt ggatggcata   135000
gctgctaaaa aatggtgaca tacttcctag gtggtgcaga aaattaagtg actgtaggaa   135060
caggcctcag cagctccttc cacttccttg gtatgattgt ttttaaacc aaggctggga   135120 ttgtatagat gcagattagt taatgtgata ccattaatag ctaacctagt gcctgctgca   135180
gggtgagcct cccctaagcc accgggaagc ggctcctgca gcctccctca cgtgtgctgg   135240
ccctcctctg gcagtcattg cctgtggtgt gctgaaggcc cagctctgac tgtgcctctg   135300
tgctctcctc gccccgcccc ctgctctctc tcaggtcttt ggtctgttgt ccgagctgcc   135360
acagcagcct ggacatccct gttggtgttt ccagccctgt cctctcctga gttccatcca   135420
cctgtgcatg gcttttcat gagtgttttc acggatggtt ctgctgtcat ctccaacctg   135480
ataaacaaag caccacgatt cagcccttat gaccccaagc ttccttcctc agttccttgc   135540
ttctgtgcat ccactgaaga agcctgttcc actgtttccc tgcactgggt ctcctgtctg   135600
caggaagcct tcagccctca cttccacact cctctaagat gtgtgcctgt gcccttctgg   135660
ggaagctcat tttcctagca gcctccagga tcttcagggg tgaatccctc ctttcccacg   135720
ttggtactct gtacacacaa catgcccatt ccctgcctgg ggagctgggc attgcttcat   135780
```

```
gaatcagagg tcaattttt ctctattaaa gtcacagatg ctcattgcac cattgtgaga    135840
atgaatgaag atagtgctta taaatcagcc agcaaggtac ccagcctcac tgtgtcaggg    135900
tctccctggg catgaggtgg ttagagtgtg tgacatgtct gtccccaagc ctgtcagctc    135960
ccagatcgaa gccagtggat ctcattcatc ctcgcagcgc ccacagcact tgcacagggt    136020
tttgtacaca taagtcattc tgtcaatgtt catgtttaat gtcatcagtg gaacactccc    136080
actttgtaaa gacttgaatg tgttcatccc tgacttttcc acatcttgtt agttcttctt    136140
tggaaacagc tgtacagttt caccatcctg tgcatccctg gagtctacct gtctctgtca    136200
tacattcaga ttcttcttgt ttcgtgtcac tctcatatcc ttttctctaa tgaaaagctc    136260
cgcctgggca tgcaaggtgg agccctggat gccagcccct cacctggcat ccagggctgt    136320
agcactcagg aactgcctcc ctgccctgcc taccccctac atcatgcgac cattccagtc    136380
cagccaatca gccccttggg acccagctta ccacatgcat atcatttatg ctgtgaccac    136440
tgactaaacc attctcttcc ttcctcccca tatttctaaa tttctaatca ttgctcaaag    136500
cccaattcag agaaaaccct agctcctcca tggcaccatc attaacaatt ttatctggcc    136560
gccccccggg aagttcactg ggctaattgc gggactcttg ttcgcaccat ggcatctctt    136620
tagcagaaca taaatgcgaa gagcacatgc atccttcatg ggaatttaaa ggagctggaa    136680
agagtgctca ccgcagttcc attctcccgc agaaatcctg catggcgccg tgcggttcag    136740
caacaaccct gccctgtgca acgtggagag catccagtgg cgggacatag tcagcagtga    136800
ctttctcagc aacatgtcga tggacttcca gaaccacctg ggcagctgta agtgtcgcat    136860
acacactatc tctgcctcca gctcctatgg gggacagctc tacagcactg gggcagggga    136920
gagaagccat gtttagtaag tcacattaat cagaaacaaa aagtagtaag caaaatatct    136980
gaccactaga aaagcatgta tttaccacgg acatagagat cgttttttg tggcgggtgg    137040
cagcccagct ggttggcagt gcaggccacc ggaggcagat cccctgcagg gacagcgagg    137100
cacttgtgtc ctgagaagag ctgctgttca tggggctggc agcaccaggg cctctcctag    137160
cctgccctgc tgacactggc cagactccta catgcttctg agtctccaga ggctacccgg    137220
ccctcctgaa gcaccagggc tgaatccacc cccagctgag ggcatgaaca ctgccacatg    137280
gagtcacaca cacagctggg cactgccatg gagaggaagt ctgtccatgt ttccttgaat    137340
actggtggcc tggtccctgt cccattcccc agtgaggcag cctgtgggga agcctggcag    137400
ggaaccaggc gcaggtcagc gtggcgccct gactcaggcc agcactgatg ggggactctg    137460
agacgcaagc tcacactcac ccagctcccc tgggctgcgc ccgttcctga tcgcttggac    137520
tttctgttct ttagagtaag aagtgatcac catttcctgc ttctttgttt ctccacaact    137580
gtgcagtgga tgcctgtttg ttttctgccc tcagaacaaa aaaaaaaaaa aatagagctg    137640
acgtgaatct tcaaaatcat caactacagg gctttggatt tttgtgtatt tgttttattt    137700
tcattttatg gatggattgt gatgaaatgc ccgtaataca agattttcca tcttaaccat    137760
tgtaagttac aatgtcagtg gcattataca tccacatggg tgtgtggcca tcaccaccgt    137820
ccacacacag aactcttta tcttgcaaag ctgaaactct acccattaga cagtaactct    137880
ctgctctccc ttccttccca gcctctgcc ctggcaggca acagtccact tgatgtctct    137940
atgaatttga ctgctctggg gctctcatac aggtggaatc atgtagtatc tgtccttttg    138000
tgtctggctt atttcaccta gcaaaatgtc ccgaaggttt atccatgctg tagcacgtgt    138060
taagaatgtc cttcctcttc atggctgaat aatattccat tgtatgttga cactacattt    138120
```

```
tgtttgtcca ttcacctatc tacagacact ggggttgctt ccatcttttg actgtttgaa   138180
taatgctgct gtgaacatgg gtattgaggc tctttgtttt atagacatat tattccacca   138240
gatacccatc ctgacaccta ctatgtttgc aagaaactga aagctttatt ttacattgca   138300
aaatttcata ttatgagatc aaggttagca tttcctcagc tgtctggtgg acaatgggga   138360
ggttaaactg tgcacatttt attttttttt aatgaacctg gaacggttat ggggccagtg   138420
tttgccatgg atcaggtcag gcagcccaca atggcaggtc tccatgttct gtacaacaac   138480
tgtgggaaag acccacagag aaagtgctgg aaggggaat gatgggtagg ttcatgcagt    138540
aaaaagattc aaatactaca gggcattgaa ctataggcca atatagcatt gctttaagaa   138600
taaacaaaaa ataagacagt aagaataagc ctagcaaaat caaagtcta taagaactg     138660 acatttcaag ccaataagag aataattcct tattcaataa attgtctgga atgacttaac   138720 tattagggt gaaaatatca aagtgagaga actataaagg ttttttaaaa aggaattagg    138780
tatgttgggt tagtcgcatt ggagagtgca aattcaccat cgacctgata cctgaaattt   138840
cctccttacc atctagaggc aagttgggaa tgctgccagg ctcctgtggt aaaggaagct   138900
cctctcttga ctggtgcttt atggctacac gttcctgctc agaatggatc tcatttagtc   138960
ttcaccaaaa aaaaaaatct catgagatga tttaagtgtt ttatggacaa gatgtctaaa   139020
actcagaaaa atttcacagt gtgcctagct tttatgttta tgttgaagtt gggcattaga   139080
agttagaatg aatgggttta cttcagagaa aattaaatcc atcacccact ccttgtacta   139140
tgaattccaa atacatatta aatacatata ataaaatatt taatatatat gtaagtgcca   139200
gaaggaaaca taaatatgaa tatttttgtaa tatcaagttg aagaaaagcc aaaatctgac  139260
atcataaaag aaaactttca agtaaaatat gttaatggct accaggaaaa tattgtgcaa   139320
tgtctgattg ccatgaagag ggttaatatc cttgctatat cactctgtga agtcatcttt   139380 aaagactaa gaaaagatg aatctcttaa taaaaacctg gcccagaaca tgagcagcct    139440
ctctctctca ctctcactgt ctctctttct gtcacacaca cacacgcaca catacacaca   139500
cacacacaaa tatggccaag aaataaagta aatgttatt tctaatgtaa taagtaggtc    139560
aaaatagaaa aagaaagcat cacaccttcc tttgcaaagt atttgggttc cttttgcttt   139620
taaacacctg ggtcagctgg ggtgtcgaga aacagaaatt ctcacgttct gcttgtgggc   139680
atatatgtta ataaaaccaa gcttggcaat atgcctgcaa tatgtatcta aagcttcaaa   139740
gtatgtatag cttgaccaa tcaatatcac atttcggaat aagagaaaaa gaaataatga   139800
aagtgaaaat cataagagat gtagaaacat attcttatac aagaattcct tgcagcctta   139860
tttataataa attttgtgaa caaattatat atctaaaaat aagagattgg ttgaaaaaat   139920
tatgcagcag ccatgctatt gataatcatg ttagatagaa gcatatttaa aggcatggaa   139980
aaattgccat gttttatatg ggttttttaag gttataacac aatgtatagt gggattccaa   140040
ttcctgtata tacatagact tatatgtcta tattgattaa ctctggatga gtctcatgtc   140100
ttctttttgc tttcttctat tatccatatt ttatacgatg tgcctgcatt tcttttttgt   140160
aacagatggt caatactaga atcataaaca gatcttgttt gtttattggc aaatgtttcc   140220
cgttagaaaa agatgcattt ttcttttaaa tattttatt ttatacaatg attacaagct    140280
tataatagaa atttgaaaat tatatgtgag tacagggtaa aaagttgaaa gaatgggatt   140340
gcacgctaca gatctagctg cttttagcac gcctgcgtag gaccttgctt tctctagacc   140400
tctgttgcag tctctctgcc tacctcctca caacgtccat cccccgcggt cactgtcgtg   140460
atgccagcct ccccggcctt catgtctcta aggagcacca gcgcggcaat tagcgcccttt 140520
```

```
tgccttggtg gtattctggc ttcacagtca catgggagat caatcgtcag ctttctgtt    140580
tgaaatctaa attcttcctg actgcagggg acctcgggac ccatgaacac ctctagttta    140640
ctatgtcttc acagtaaaag atatctgcat gactggactc tttaacaaat ttggtggtta    140700
acctactctt tctatataga tatagcactt cgaccttcag acttctcaat actgataaaa    140760
agaaaacacg acagatgaca ggaaaacctt tgcagctata atttgtaatc ggccaattat    140820
aaaaactgca aaaattgacc agatagctaa ggttttacac agtcatgaaa gtgatctgca    140880
ctgttaacat ttcaccctct gtgcaccatt ctgtgcttct ctctggtttg gagtctagaa    140940
ggttttattt acaggctatg acttaacaat cccagaacgg ctgacacatg cagtcactca    141000
agactggaca cagcaaggaa gtagtgggtc catgccaaag gctcagccag acgagacact    141060
ctagctgtgg caggagatgc cagggaatgc tccaagccta agcagattgt aaacaaggaa    141120
cctcaaattc atgaaaaatt cttgcttatg tgcccatgt cagtaattac tctctgcctc      141180
agtttccgca gctgacatgt aaataaaagc agttcatggt tcatcttctt ttcttatcgg    141240
ggtctcaagt gattctacaa accagccagc caaacaatca gagaataagt tgaaaagatt    141300
gtcttcattt attgaatgtg cttaactcag gcccgggaaa gggcgtcatc agtttctcat    141360
catttcactg agatatgcat ctattacttt tacatttcag gccaaaagtg tgatccaagc    141420
tgtcccaatg ggagctgctg gggtgcagga gaggagaact gccagaaacg taagtcagtg    141480
aacagcctca gacccatgtg tgaccgcccc tctcttcctt cacttgctta ggtgattgga    141540
tttgtttcc ctctgaagac tccaaagagt tactttatta cagggtcaga tgtgaaccag      141600
taggtgaagg acagtcttgc aaatctcacc gcatgcagtt aatccagggt gggctatttt    141660
gggagcttca gcctatcaca aataagtgaa catcagcagg ggctgggcgc ggtggctcac    141720
ccctataatc ccagcacttt gggaggcgga ggcggtcgga tcacgaggtc aggagatcga    141780
gccattctgg ttaacacagt gaaaccctcgt ctctactaaa aatacaaaaa attagccggg    141840
cgtggtggcg ggcgcctgta gtcccagcta ctcgggaggc tgaggcagga gaatggcatg    141900
aacctgggag gcggagcttg cagtgagccg agattgtgcc actgcattcc agcctgggcg    141960
acagagcgag actccgtctc aaaacaacaa caacaacaac aacaacaata agtgaacatc    142020
agcaagtacc ccagccctgt cctctgaaca cagcacactt tcccaggaat ggaagacttg    142080
ctcctgttga cagcagtcac cagacttctt gtttcctctc cctccctggc tttctttggt    142140
acccacctac acagaagcct gagcacgggt tctcatgggg acttttccat gtggaccctg    142200
ctttacgatg gagagggcca ttctcctagg tatggttgtc tggctcagcc tctcagtggc    142260
caaggaacct ggggacatga gctcaaaaac ggacactatg tccttaagct gaattgtggg    142320
ggggctgtta ggcccttcta aacactactt cccagcaggt attttgttc tttgtatgtg      142380
ctttctgcat tgcccaagat gcatctaatt atttagcagg tctcaaagtc tagacttgat    142440
ctcatgagtt ctcttaagtg attaaaaata aatcaggaga aaaagaggc aatcagaaaa      142500
gggcatggtt tgacttagtt tgaatgtggt ttcgttggaa gcaaatgtgt cttcactttt    142560
tcatgaaaaa gtctgcaagt gctctgcgac atccctggga aatgatccta ccctcactct    142620
tcagctcaca gggaacctt gctctttttc agtgaccaaa atcatctgtg cccagcagtg      142680
ctccgggcgc tgccgtggca agtcccccag tgactgctgc acaaccagt gtgctgcagg      142740
ctgcacaggc cccgggaga gcgactgcct ggtaagatgc ccctccagca gcctccctgg      142800
agcaggctgg ggctgcaccc gccccaccca caccaggaca gaagacttcc tgtgggggag    142860
```

```
ctgtcaatta gcatttgtca taacagacag gatattgccc tctgcctggt gacaaagtat   142920
ctttagtatc ctgcctccac cactcactga gaccttggga aaatgatggg actaccatgc   142980
ctccatttcc ttacctgaca atgatgcata acaaagtctc tcccagttga atgcttaaat   143040
gatgagatgc ctgtgatgtc cgtcattagg acctgggcac agaacaagca ctaaatacta   143100
catgcaagta tttgtcatga atgtgccttg ttgccagcag cacactctct ttattgtttg   143160
acttcggcta tacctctaga gacttgacac tgtgaggtcc ctaagagacc catggagagc   143220
cacacaggtc ttgctggctg gggctgggtt agggcctcct gacacggatc cctcggctcc   143280
tccaccactg ctcaggcacc tcctgagctg caccctgccc tcaaggggtc ctgaagtact   143340
cactgtcgcc ccattgctcc agaaagtgcc agcagaagcc ttgctgcccc agcgggctct   143400
gagcagcact ggagggtaca ggtcagaagc gtcttggaag tcctggagac gccaaggctg   143460
gtggatgtga ctcctggagt gggagctggt gtgacgaagc ccttcctaag actaaatcca   143520
gagcactctg tggtttcaga gaagattcct aaattccaga gtttggaccc agacccagga   143580
attgtgactt ggttggcctg agctgttcct aatgtgagcc ccaggagaa gactgtgcgt   143640 ggggttggtc ctaggaaaag ccctcgctgt attgggtctg gctcctttac acggcattgt   143700
tctagcaagg ctttctgcca ttcagcaata cattataaaa tataccctca attgtacttt   143760
ataagggaag cccaatgtcc tttataaggg aaattaaaca taatttcatt ccatagtcac   143820
cgctataatg tgtgaactcc atcatctata cgttagtaaa cagacgtatt tttatcataa   143880
tccataaatt atgataggtg ggacagtgca cctaagaaaa aaatggactt tttagagaag   143940
ggtctttctg actctgcaga gggcgccagc tgggttttcc cacactagtg gaacactagg   144000
ctgcaaagac agtaacttgg gctttctgac gggagtcaac accgtgctgc gcttcctccg   144060
tgtgtggcgc tgagtgtact tacctcactt gcccagcgtg tcctctctcc tccataggtc   144120
tgccgcaaat tccgagacga agccacgtgc aaggacacct gccccccact catgctctac   144180
aaccccacca cgtaccagat ggatgtgaac cccgagggca aatacagctt tggtgccacc   144240
tgcgtgaaga gtgtccccg tgagtcctcc tctgtgggcc ctctaactgg tcaggcatcc   144300
ttgtcccgct ctgtctcctg ctgagccctg gagtatccca tcttggagag tctttgggtg   144360
gatgtgtttg ccttgcttgg aggaggcgac cctgtgcccg tccaggcaca caggcgaggg   144420
gaggggctgg cttgctaccg aggagcgggc aggtggtggc catctccacc catggggct   144480 gctcagtgca cagggcagat ctgggtggcc aggccacctc acaggagaaa cacctgctgc   144540
tcagccctca ccactcatcc agcagccaca gccgtgggta ttcagttgtc tgctgggcac   144600
aaagccgtgg gcatgccact gtttagtgct tgtgccaagc aggtatttaa tacaccgaaa   144660
tcagagagtc tatcagaaga cctgccttct tgagtggtta aaattctagt gaaagttatg   144720
cctcttagga gtattgcaga ggttttgttt ttgtttttat tttgtttttgt tttaatggtt   144780 tgggtttgag ttttgcttgt ttgtacttac atttgtactg gtggctccag ggtttaggga   144840
aattgtgaca taaaataatt cctgacagag aaagcaaaac tttgtctaat gaaagagttt   144900
tagaagccac tcttgatctc tagaagggga gattaactga gaaaaaaaat tgaaagaaca   144960
attatgaggg ggagatttta ccctgccaga tttgtgtaca tgaaaaattt tacattccgt   145020
atggaaaaaa aaaacacaaa ataataagcc attataaggt aaatgacaaa caaagctaaa   145080
gaaaaatgtg ccacagtgat gacacagata tatctttgag ataggggctta acagagcttt   145140 aaaatccata ggaaaacact tcgagcctga gataccaaga gcagtggtt cacagaagaa   145200 tcatcaatgt cctataaata ttttgagga tcttcttggg gaacttaaaa caggaacagg   145260
```

```
ccaggcacag tggctcattg gctcatgcct ttaatcccag cactttggga gactgaaggg   145320
gctggattgt ctgaggtcag gagtttggga ccagcctggc caacagggtg aaacctcgtc   145380
tctactaaaa atacaaaaat tagccgggcg tggtggcgca cgcctgtaat cacagccgct   145440
caggaggctg aggcaggaga attgcttta cccaggaggc ggaggttgca gtgagctgag   145500
atcacaccac tgcactccag cctgggtgac agagcaagac tccatctcag acaaacaaaa   145560
aaggaagaca tagagctcct aaaaataacg cagaagtctg ctattaatac aaatgaatta   145620
ctttaaaggt gagagcaggt ggaggagagg gctgaggtgc ctgctgggac gcaaaacagc   145680
tggcccctca agggacccag tgtttcctgc catgatgaaa cacctgtatt gtccacattg   145740
cggcctagaa tgttattaaa ctcttgaacg ggattccttc tctatttgca acctttcatt   145800
ctttgtcctt aaagtaaata aagccaaagg aggatggagc ctttccatca cccctcaaga   145860
ggacctggac cgcctgtgtg aggcccgagc acctggtgcc accgtcatca ccttcctttc   145920
atgctctctt ccccaggtaa ttatgtggtg acagatcacg gctcgtgcgt ccgagcctgt   145980
ggggccgaca gctatgagat ggaggaagac ggcgtccgca agtgtaagaa gtgcgaaggg   146040
ccttgccgca aaggtaggaa gcccgccggt gtgcggacga ggcttgttct cggctgctga   146100
ggctgggctc tcatgccacc tccaaaggaa cacatcttcc tcttctcatt aaaaaacaac   146160
tatacatatc gtttctttaa aacagaagat aaagctgtaa agctaggtta ggcaatggga   146220
aggcactgaa ggttgtgacg gggtgggggg ctctgatgag aacagtcaca gagccagccc   146280
cgctcagcag ctgccaggtg cccagccctg gggagaatcc agggaaggca gagctggaag   146340
cagtgcagct ccaagcggcc catgggaaat aatgaggaga acgcaaggtc agtgtgaggt   146400
gacagggatg gcatctccta caccgccgta gccccaaagt gtactatagg tcctggtgtc   146460
ccccttccc gcctgcactc tccccagccc cttcagtgtt tgttgagtga atgaaggatg   146520
atgtggcagt ggcggttccg gtgaccggaa ttccttcctg cttccctctg cctgtggatc   146580
cctagctatt cttaatccaa caaatgtgaa cggaatacac gtctctctta tctctgcagt   146640
gtgtaacgga ataggtattg gtgaatttaa agactcactc tccataaatg ctacgaatat   146700
taaacacttc aaaaactgca cctccatcag tggcgatctc cacatcctgc cggtggcatt   146760
taggggtga gtcacaggtt cagttgcttg tataaagaaa aacaaaatct gccttttta   146820
ctggtagaga ttggtgatca ataatcaccc tgttgtttgt ttcagtgact ccttcacaca   146880
tactcctcct ctggatccac aggaactgga tattctgaaa accgtaaagg aaatcacagg   146940
tttgagctga attatcacat gaatataaat gggaaatcag tgttttagag agagaacttt   147000
tcgacatatt tcctgttccc ttggaataaa acatttctt ctgaaatttt accgttaatg   147060
gctgatgttt tgatattttt caaaagtgca gtttctcctg caggcaaaag gggacacgtt   147120
aagtccaggc ttgggtcatt cactgcggtg taaacacgct ttctccctcc cgcccggccc   147180
cagccagctg ccttggtggc ccataacccc tgagggtaga gggaggggac aggggtaggt   147240
gacaggcagc ctgggcctca ggcttttgaa actggacgcc agagccttgt ggggccacgg   147300
gcaagcctcg ggtctatgac tgccgcctga gctccgcttc cttcctctct aaaatgggaa   147360
gattagacca aaataacaag actgttttaa ggttggaatc aaataaggaa atttgtaaa    147420
gctccttgta tgtgatacca gatccacaat tggcagataa tcgcagcagg agcctcttcg   147480
gggtaatcag atacgcggcg cagcagggct ctcaggccca cagccagggg ggcggcggga   147540
gacatgcgga atcgcagcgg aaggcgggag gcagctgtga actgtggctc ggcctgcgtc   147600
```

```
cgccctgcgc atgtacactc agagaagatg ataatgaaaa agaaagcaaa tccaattttc   147660
ccacttactg ttcatataat acagagtccc tgagagtcta gagtaatgtc tcatacaaaa   147720
aagaaactcc tacgtggtgt gtgtctgaag tctttcatct gccttacagg gttttttgctg  147780
attcaggctt ggcctgaaaa caggacggac ctccatgcct ttgagaacct agaaatcata   147840
cgcggcagga ccaagcaaca gtaagttgac cacagccaaa gcctggtaga ttacatttgc   147900
cttttttagtt ggaaattagg cttaacagga gagttgctaa gatagggcac agagctcctg  147960
catctctcgc cggcattccc aaatgctatc tcacatgagc aggcacaggg agcaagactg   148020
cacgaccact ggcacaggct gtccgctaaa ccacagactt ctcagcgctc gccagtgctt   148080
ctgcttctgt gtccactcca gatcccacat tgcacttagt tgtcaaatct tttcagtcca   148140
tttctaacct atattagctc ctgtgtcttt ccttgtcttt cacggccttg acacttacaa   148200
aacgtgtggg tcaggtactt tgcacactgt ctaaccatgc ctgttcagct ggtgttttct   148260
caggatgcaa ttgaggttat gcacatctta tcacagggac cagagagact ttttagcacc   148320
actcttcaag aatttccact ttttcagctt tgacagtgga atagacatgc aggtgctcac   148380
acacaagcat cttaatatg gtaatggtaa tcatcagttt agtggtgtgg aggaggagat    148440
gggaatctct tagtgaaacc cgccttggaa gcagcctcgt tatgagaact gctgcccta    148500
cttgactctt aaagcactag ataatactgt gcaacattaa agagaataag agtgcgtgaa   148560
atatgcattg cctcccataa actcccttgg ctctgaatct ctgatactaa atatgtggct   148620
accgttgctt cccagaaagg cctttttgct ctgaattctc tggaatgctt tctttgacca   148680
agattcttat aaaaataaga gatttagagc aattttcttg gatggctggt atgagccagt   148740
tggcttagtt gtagggattt aaacaagata agggttactt acttttcaca tttaatgaga   148800
agtctggtga ttccagctcc tactgagaca gggtggccac acgttccagg gtgtgactca   148860
ctgaggcccc agacctgccc tgcaaggaaa acctggctct gccctggtgt cctggcctcc   148920
ctgggcatat gtgggggaga attcctaatg gtattggtta caggctccta tgcgagacca   148980
ctcatctgtg taggagaaag gaaaagatg ggggaaagaa gagcagcagg gagaggagaa    149040
gcctctggat gatactctaa cccccctgcca tccaacacct gaacatcagt ctcttcatcc   149100
agtgctctca gctggcccag cccccagcct ggggtcagat gagagcttcc tgcaaatgca   149160
gatctctttc ctgtggctcc ttctcaatta cagacagctc ctccacaagg tgcactctgg   149220
ccttgtgctc cctccccaaa ccagcccagc cctcccagcc tgcatcatcg tggtcctgta   149280
ggggctagag gttctcacac ccatcgtggt ctggcagagg ctggtggttc tcacacccat   149340
cgtggtccgg cagggcttta gtggttctta tacccatcgt ggttcaggag gggctagtgg   149400
ttctcacacc catcgtggtc tggctggggc tagtggttct catgtccacc gcgtgctttc   149460
ctgctcctcc aggtggctga ggacatcccc ccttcggtct gaatgacttc catccagtca   149520
tctgatatac acattggacc acccaatagc atcctagtgt catgttggat ggtgaagaaa   149580
atgccacagt tactgctttc agggcctcac aaccttgggc atagcttttt ggaggaaggc   149640
cccacttccc aggcatccct cccagacctg gtcagaggcc cctgctcttt gcttccatgt   149700
tgcccacact cactgtgctc ttcacaccgg ctcaaaatga tctgcttacg gggttgtgtc   149760
accaccagat caagcgtcct ggagaggagg aaacatattt aacctgcaca gaatttggga   149820
cagagaacct ctagtgtttg ttcaataaat atatgaatgg atagagggac aggttgggtg   149880
gtggatagat ggatgaaccc acacctttga agtgtatttg gctgtttgag aggttagaat   149940
atgttctcaa tttccaggca aaatgaaaat ggagaaaata taatgacatt aaggcatttt   150000
```

```
attcatcctc cccatctgcc actgggttaa agatactaaa taaacaagga actatctttt    150060
gcctggagga actttaaaaa cacctgcagt tttcaaaagg tgcagtgtgt gcctcccaca    150120
gcatgaccta ccatcattgg aaagcagttt gtagtcaatc aaaggtggtc tggagaaaca    150180
aagttttcag ggatacattg ttttttataat ttttcaccac atgattttc ttctctccaa    150240
tgtagtggtc agttttctct tgcagtcgtc agcctgaaca taacatcctt gggattacgc    150300
tccctcaagg agataagtga tggagatgtg ataatttcag gaaacaaaaa tttgtgctat    150360
gcaaatacaa taaactggaa aaaactgttt gggacctccg gtcagaaaac caaaattata    150420
agcaacagag gtgaaaacag ctgcagtaag tcaccgcttt ctgtttagtt tatggagttg    150480
gttctaatgg gtcctttatt tgtatttaga atattgaagg gctattccca tttaaattac    150540
tttttttcagt tccttaagaa gcaaattaaa atcttaagat tcctaactgt gaaattacca    150600
tgtgaattcc attaaaactt tttccagatc attaccattc aatgggatga atttaccctg    150660
aggtttaggc taccaattat ttgtaatgta agtaactaaa tttagtatta gttatattac    150720
cttttagttg taggtcactc tctgctcatt tcagcctgta aagactacag ctacacacat    150780
acacacacag aggaatggaa tgagcacttt acatcaacac ttcctgttct ggctctagag    150840
cctcagcttt tgaagctggt gagagcctgg cctgtgctgg gccttggcca cgggcagcgt    150900
cagctttgag tcaagtgctg gtctggcctc cctagctttg agcctctgtc aattccctta    150960
atctgtttag gctttggctt cctcatccat agaatggaga tatgaatgat tcctacgccg    151020
tagtgctttg agagaattca gtgaaattcc tgtgtgtaaa acccttccat ggtgcctagc    151080
acacagcaca cagccaatgg cccaatggct cctatcagct gtgggatttg tcatcagaac    151140
accaccagct ctgctccagg ctgccctggg taccatcaaa acacaccctg tgcccagcag    151200
cacctgctcc tctgcacacc tggttccttc agcaggggca gtggccgtgg gagcacagaa    151260
aacatggagt cccatctggt ttaattgatg ccattgccaa aggggaggac tcacggcacc    151320
ccctctcggg tgccagggtg cctggctccc accaggagga agacctgtcc tccactgtca    151380
ggcacatttc agtcttccca gcagccagca caactacttt gtccttccag tcacggtcgg    151440
cctctgggaa gcccagtctg tgtcctcctc cttcaggggt agccagcatg tctgtgtcac    151500
ccaaggtcat ggagcacagg gcccctcccg ggaaggtgcc gtctcctccg gcccctcggg    151560
tccctgctct gtcactgact gctgtgaccc actctgtctc cgcagaggcc acaggccagg    151620
tctgccatgc cttgtgctcc cccgagggct gctgggccc ggagcccagg gactgcgtct    151680
cttgccggaa tgtcagccga ggcagggaat gcgtggacaa gtgcaacctt ctggaggggt    151740
aggaggttat ttctttaatc cccttgcgtt gatcaaaaat aaggctccag gttgttgtta    151800
tagctttaca ggcattctgt ttgattttct cttcctttta ttctttgccc ttggcttttg    151860
gaggttttgg gttttctgtg gggagacggg aagttgtttg attgcgttat ttttggcaaa    151920
tttaagcaca ataggaaata agcaagtatt attgcctaat ataatccaat aatttataga    151980
atctcttttc ctggaagtat cttaaatttt tctaagctac aaaaagttcc taagacaaat    152040
gagacagtca tcaatggttc atctagccaa caccgtggcc attgggctt ttctttgtag     152100
tgcccgattc ctggtgtgtg aaaataaatt aacacaaatt atattgccaa gttaatatct    152160
gttttatgtg cccccagcat gtgttgaaca tcaaacagta ccagggactt taaatatacc    152220
cacggacaaa gaataattc ataatgatgt ttgttgaatt tagttgcaat caataaaaag     152280
tgcagtttgt gaatgctctg aggttcttga tattgatgta aggctttgaa cgacaaatga    152340
```

```
ggacaaaaca taaataggaa agtaaaactg aaggatagag gccaaggcca tgttttagaa   152400
gatttaaaga aaaagggaaa tttggtgagc accataggaa ttacagatgg ctgtaggaat   152460
tcttcctgtt ttactctctg ggcatggacc acagcttgga tccagaaata tttaggagca   152520
ggataagagg accaagttca attctatagg aatcctttag ctgataggct cagaacaaat   152580
cacataattg atagtgctgc ttcaacttca agtaaggaat attgatgcaa tccttacagc   152640
tacaaatgga cagtggtctc atgttttcag ttttcaagtg tttcttaaga ggcaaggtga   152700
tgaaaacgcc cacgtgggga gccccatgtc cttccattag tgtagagaaa cctggtgtcc   152760
agcagcacct gctccctctg caagcccagc cccttcagc aagggcagtg acccagaaa   152820 gaagcacaga agacacaacc ctgtatcaca ttttgtttaa tggtgccatt gaccaaaggg   152880
gaggatgaaa ggcacacact tttttgttgt tttttgagac agagtctcac gccatcaccc   152940
aggctggagt gcagtgatgt gatctcaact cactgcaacc tctgcccct gagttcaggt   153000 gattctcctg cctcagcctc ccaactagct ggaattacag gtgtgcacca ccatgtccag   153060 ctaattttt gtagttttag tagagacggg gtttcaccac gttggccagg ctggtctcaa   153120
actcctgacc tcaagtgatc tgcccgcctc ggcctcccaa agtgttggga ttataggcat   153180
aagccactgc acctagccaa ggcacacact ttggagaata acactcctt gttcgctgct   153240 ggagggtaga actatgcttg actactaggc agagtccagt cttactgaca acagccgta   153300 catctgttct gtcttttcaa tcaaacatca gcttcttgct taacattgat gtgtacatct   153360
tgagggatgt caaaatattg taagctaagt ttttcatacc tgtgttccac actcaccatt   153420
tttagtaata accattgagc gagttcattc tccctccttc cttttctat cacttaatct   153480 aaaattatca tttttccagc ttaattttga taaccatgaa tctggtatta gaggcaggga   153540
acacctcctc aggactatct tttcttttat catttggctt gcttacccaa tatgcaaaaa   153600
ctatgctgta gaaaagcag aaaagatatc ttgattatga atgaagctcc tgtgtttact   153660
cagagagaag atgacccagg attcagttaa caaaatcagc tgattatatt actatatagt   153720
cctggagtcc caactccttg accattacct caagttattt ggaattttga agaggtgatt   153780
tgtgttcctg caataatgtc tcaggggtgg gctgacgggt ttcctcttcc tcctctcagt   153840
gagccaaggg agtttgtgga gaactctgag tgcatacagt gccacccaga gtgcctgcct   153900
caggccatga acatcacctg cacaggacgg gtaagagccc cttgctgcta tccacgtcca   153960
tttcatggga agggccttca cagaagccga acagtgatga tgcccaggg catcctgtgt   154020 gggcaggacg gccatcagag ccacttccca gaggagacgg caggcgctga cagcgctgtc   154080
cgggcagggt gtcggtgaca ttagcacaca cattagcctg cgatgaacat tcactctttc   154140
tgctgacacc cccaaccta tctaagctta tcaaatcctc acatttaacg gaggctgttt   154200
tcacctggtt tcccccatcc ctgacctagt cagcattgct ttatcgcttt catcaaacat   154260
cctcaaattc ttaacattag cttgtaatta attgaagaat ttttaaagaa attgctagca   154320 aaactttta aactgcacaa cttttgtatct atatgttcaa taacatatag atacaatatt   154380
ctttacaata atcttttaaa gaatatgagt gagaattcgg gcccctctca caccaaatgt   154440
cctgatgttg ttaattctca atgttattat atagggagtc ctgttttctt gtgagcttca   154500
acagccagtt ctaaatctac taactgaaaa catttttag acattctcta aattgggcag   154560
aagatgacag gactgtgttt tgagggatag gctgccagcg tggctgctta caaagtaaag   154620
acttggttta taggtttgca tggtgttggg ttaaatttct gtcattaaaa taattggcga   154680
tattgacata gtcatctaat tatgctggct ctgggcacac acagcccttg agtggacaaa   154740
```

```
accaacatga gagaacttag ccaaggggaa agcctttccc tgctggtttt atttctgcta  154800
cttctgaagt gtggggcaca caacctgagc agtgctttta tttgagtccc aatgctttta  154860
tttgagtttt gcaaggttat tccaagtttt acaaatagaa ggtagcgtat gactcagtcc  154920
ttgatatgcc aaccactgca cagagacttg ccaccttcct gtcactggag aaacactcat  154980
gtgggttttc ttaaatttgc ctccctctga gcttcccttt aacttcaact ataatatgca  155040
agaaagacta tctgaccata aatacacatt tgggccaatc aagatggttt tgccaaggaa  155100
agatgcccac aatggttaag cagaatgcaa taatgtagag aatatcattt ctttcatgct  155160
ggtgtatatc atatgcattc aaaaacaggg agaacttcta agcaactaac agtgaccata  155220
tcaagcaggt gcaatcacag aataactggt tttctccttt aagaattttt ctatcatttg  155280
gctttcccca ctcacacaca ctaaatattt taagtaaaaa gttacttcca ttttgaaaga  155340
gaaaagaaag agacatgcat gaacattttt ctccaccttg gtgcagggac cagacaactg  155400
tatccagtgt gcccactaca ttgacggccc ccactgcgtc aagacctgcc cggcaggagt  155460
catgggagaa aacaacaccc tggtctggaa gtacgcagac gccggccatg tgtgccacct  155520
gtgccatcca aactgcacct acgggtgagt ggaaagtgaa ggagaacaga acatttcctc  155580
tcttgcaaat tcagagatca aaaatgtctc ccaagttttc cggcaacaaa ttgccgaggt  155640
ttgtatttga gtcagttact taaggtgttt tggtccccac agccatgcca gtagcaactt  155700
gcttgtgagc aggcctcagt gcagtgggaa tgactctgcc atgcaccgtg tccccggccg  155760
ggcctgtgtt gtgcaatgct gcacatcaca acaggagggt aggggacaa aagagcacag  155820
gtcctggcag ctgccacagt ctccagggc ttttgcgttt ctctccagat ttctaaggtt  155880
aacatgggga ttagctgttt tgcaatgaat aaaaggtaac attgcctgga atgttgctta  155940
aagacacttt tttaaagcta gttgattgtt aagctgttgc tacttaaatt aaaactactt  156000
tgggccagac gcagtggctc acgcctgtaa ttccagcact ttgggattcc aaggcaggca  156060
gatcacttga ggtcaggagc ttgagaccag gctggccaac atggtgaaac cccacctcta  156120
ctaaaaatac acctgtagtc ccagctactc aggaggctga ggcaggagaa ttgcttgaac  156180
ccgggaggca gaggttgcag tgagccaaga tctcgccact gcactccagc ctgagcacca  156240
agagcgaaac tctgtcgcaa aaaacaaaaa caaaaaaaaa agctactttg actggaatta  156300
gcagaagcac tctgattgtg tgtatcttat ttactggaat aataaagctg tcaatcaaac  156360
tggatcccac tcaacaatca gaaagagaag ttgagctgtc atatagtagt tcacacttac  156420
ttctgtttct caaaatcctc agctttgttt ggaactgtta ctcattcttt ctctgaatcc  156480
atctgtatga ttgtgtgcc cttgggcaag ggtcttacct tctctgtgcc tcactttctt  156540
ttctgtaaat tgggataata atgctgcata gctcacagga tttttatgac catgagttaa  156600
gatatgtcat atacttaaaa tggtgcctgg aaaatggtga atactgagtc aatgatagca  156660
tcattgatgg tgggatggtg atgaggaggt gggagtcaca atggtggtgt tgatggtggt  156720
gatggtggtg aggaggtggg agtcacagtg gtggtggtgt tgatggtggt gaggaggtgg  156780
gagtcacaat ggtggtggtg atggtgttga tggtggtgag gaggtgggag tcacaatggt  156840
ggtagtgatg atggtgttga tggtggtgag gaggtgagag tcacaatgtt ggtggtgttg  156900
gtggtggtgg tggtgaggag gtgggagtca caatggtggc agtgttggtg gtgaggaggt  156960
gggagtcaca atggtggtag tgatgatggt gttgatggtg gtgaggaggt gagagtcaca  157020
atgttggtgg tgttgatggt ggtgatggtg atgaggaggt gggagtcaca atggtggtga  157080
```

```
tgagggtggt gatgatgatg aggaggtggg agtcacaatg gtgtcagtgt tgatggtccg   157140
atggtgatga ggaggtggga gtcacaatgt tggtggtgtt gatggtggtg atgatgatga   157200
ggaggtggga gtcacaatgg tgtcagtgtt gatggtggcg atggtgatga ggaggtggga   157260
gtcacaatgg tggtggtgat gacggtgttg acagtggtga cgaggcggga gtcacaatgg   157320
tgtcggtggt gatggtggtg aggaggtggg agtcacaatg gtggtggtgg tgatggtggt   157380
gatggtggtg aggaggtggg agtcacaatg gtggtggtgt tgatggtggt gatggtggtg   157440
aggaggtggg agtcacaatg gtggtggtgt tgatggtggt gatggtggtg aggaggtggg   157500
agtcacagtg gtggtggtga tgagggtggt gatggtgatg aggaggtggg agtcacaacg   157560
ttggtggtga tgatggtgtt actggtggtg acgaggtggg agtcacaatg gtggtggtgg   157620
tgatggtggt gaggaggtgg gagtcacagt ggtggtggtg ttgatggtgg tgatggtggt   157680
gaggaggtgg gagtcacagt ggtggtggtg ttgatggtgg tgatggtggt gaggaggtga   157740
gagtcacaat ggtagtggcg atgatggtgt tggtggtgag gaggtggaag tcacggtggt   157800
ggcgatgatg gtggtgagga cgtgggagta acaacagtgg cagtgacggt gattgagaca   157860
tgatgatgat ttgtcaactt tctaggaaaa caatcatata atctccaaca gtgatatctt   157920
aatatctttt ccaaaagtat cagatcatat tataagggcc aagtttccag aataatcatca   157980 gacataatga cagtggacat cagagcttgg catctaaagg taatgggaat agctctaatg   158040
tctcagcgtg aaaacaaca tttgctatta gtctgagata ctaattatct agttaaggaa   158100
gtactcacct atacctagtt tttaactgtt ttttaaaatc tggaattgat tttgaatttt   158160
aacaaatatt tccctgggaa caatgtaaga ttcttcatat tttcgccttt gggtatacca   158220
acatgccagc tctgttggcc actttgtgag ctcgatgaag catggtataa aagatgcttt   158280
gctagtgttt cacgtaatct atttctataa gcaattttgg agctaagcct ctgaaacaga   158340
attatattat ctgtatagaa taaatgtttt atcttccccc ttttctttct tctggaatag   158400
atgtgcatca gtatctctgc atcaatatct ctatatcagt atctctgtgt cagtgagcat   158460
atgttgctgg gcttagggga ggtccagaaa gtgattgggt tttggcattt tcaatacact   158520
tactttgtat aagaaatagt ttgccaaata tagaaagagg ggatttagtc aagatttaaa   158580
ttaaaaatgt tagtggtcat ttttctaatg tctttctatt ttttcccagg tcctaataaa   158640
tcttcactgt ctgactttag tctcccacta aaactgcatt tcctttctac aatttcaatt   158700 tctcccttttg cttcaaataa agtcctgaca ctattcattt gacatatgga attttataaa   158760
tattttcttt agtatgtgtg attacattcc tgattctgag cctttttaga tgagtatata   158820
gtttgatata atcttgttat tgccacctgt gtcttctccc aaagccatta attatatagg   158880
aattacacga tagaaatggg tttaattttt aaaatacggc caagtgttga tgagagggaa   158940 aatttttta atttctttca ctgagtattt atgacgtgca caacattcct gaatatattg   159000
tctctctcat ttctcagatg ggatgtattg ccttctccat ttctattgtt aaagaaacac   159060 ttacagggggt ttctttaaca acttgtgaac agcagcatca gagcccagac tacagcataa   159120
gcagctgctg attccaaaag ccctaccttc caaccgggca ggtgcagcca cccagacgag   159180
ggggaggaac cctggaggaa tagctatttc tttttttttt tgtcgagac ggagtcttgt   159240 tctgtcaccc tggctggagt gcagtgccgt gatcttggct cactgcaacc tccacctccc   159300
aggttcaagc aattctcctg cttcagcctc ccgagtagct gggattacag acacctgcca   159360
ccacgcctgg ctaattttg tattttagt acagacaggg tttcaccatg ttggccaggc   159420
ttgtcttgat ctcctgacaa gtgatccaca caccttggcc tcccaaagtg ctgagattac   159480
```

```
aggcgtgagc cactgcgccc agcaggaata tctattttta aatgaactg tgttttcata   159540
gtacacggtg aggagaaagt tgctttgaaa tctttatcct aataaaccaa ataatatgaa   159600
aatttgccta ttttaattat atgtaacaaa gtttagttac tgctataatt gcaaatatgt   159660
ataaattcct taccaaaaaa aaagaatca agtgggagcc agagaataat ttttctgaca    159720
gaattaaata acatgctata gctgcttgag ttcatactca atagtcattt ctgcagagtt   159780
accgagggcc tcatcagcgt cagcaggagc ccctcgcctt ctgacgctct cacatccttc   159840
tctcctgcag ccccgtcctg ccactgtcct tgtccagctt ctcttcaagg gtcaactggt   159900
ctacctttcc ctacaagtct gtcacagctt cttgttagca atccctatgg ttgcccaaaa   159960
gcattttcag agcctgcata agactgcatc ttgtagaaaa tttgcagttt caatctgccc   160020
tccctctgcc gggtgttccc attgtattgc attcagcagg cagggagaga ctgctattag   160080
gtctgttcct gagtgactgc tttctgtctc agactgtttg gtgtctgtag gaggtagtgg   160140
ggtgggcagt aacgaggtct cctgtatatt ccacccctac gaagcctgtg tgtttggttt   160200
atgaactaag ctcaaaagca ccacaggggt aagactgcag tacatgacac catggaaaag   160260
agggagcacc cagaccccca aattaagaag agcagtgtag agaacagaga cctggagagc   160320
agagatagaa actgttagga tcagattata gtgttacacc agggctcccc aggcctctca   160380
catattgaaa tgtacttgtc catctttctc caggccagga aatgagagtc tcaaagccat   160440
gttattctgc cttttaaac tatcatcctg taatcaaagt aatgatggca gcgtgtccca    160500
ccagagcggg agcccagctg ctcaggagtc atgcttagga tggatcccct tctcttctgcc  160560
gtcagagttt cagctgggtt ggggtggatg cagccacctc catgcctggc cttctgcatc   160620
tgtgatcatc acggcctcct cctgccactg agcctcatgc cttcacgtgt ctgttccccc   160680
cgcttttcct ttctgccacc cctgcacgtg ggccgccagg ttcccaagag tatcctaccc   160740
atttccttcc ttccactccc tttgccagtg cctctcaccc caactagtag ctaaccatca   160800
cccccaggac tgacctcttc ctcctcgctg ccagatgatt gttcaaagca cagaatttgt   160860
cagaaacctg cagggactcc atgctgccag ccttctccgt aattagcatg gccccagtcc   160920
atgcttctag ccttggttcc ttctgcccct ctgtttgaaa ttctagagcc agctgtggga   160980
caattatctg tgtcaaaagc cagatgtgaa acatctcaa taacaaactg gctgctttgt    161040
tcaatgctag aacaacgcct gtcacagagt agaaactcaa aaatatttgc tgagtgaatg   161100
aacaaatgaa taaatgcata ataaataatt aaccaccaat ccaacatcca gacacatagt   161160
gattttaatt atttaagagt agtttagcat atattgcttt atgatttaat taaaaatctc   161220
caaaatatat gccaaagaag tagaatgaga aaaatgtata tttctctttc acttcctaca   161280
gatgcactgg gccaggtctt gaaggctgtc caacgaatgg gtaagtgttc acagctctgt   161340
gtcacatgga cctcgtcaag aatgaccaca ctgctgtggg tgaagatgct ttcctgcatt   161400
tctgactgtc ctctgtcctg atcaagtttc tatggctctg gccagccta ccctcagcca    161460
gggtttctgc agagactgcc cagctggttc cacgtggctc cacgtgccaa ctttgtcctc   161520
agtggaggga aagttggaca cacagtgctg gggctgctcc ctgctccgcc gttgctcgat   161580
gcatggcctc cctctgaatt ccttggttcc actggttttg ctgggtcctt ctgtgcctct   161640
agctcctctt ttttctgtc cacttacccc attggtccca tcacaagcct gtgtgtgagt    161700
ggcctttctg ttcgatgaca acctccagca tagggagtg tttctccttg ctttctttcc    161760
cagacacact gcccagcaaa ggcaaaaggg cttccttcaa catcagctct ggccagtttg   161820
```

```
ccagagcaaa gccctgagaa aagcaaggtt gaaaagtctt attcaaactc accaggaaag   161880
agtggtgtta ctctcgatgg cgtctagcca ggaatcatgg aattatacac cgagcacctg   161940
tttgccattt tggatgtttc caaacatgaa ccaaacttcc aggcccctct gccatctctg   162000
gtaacattta caaagtccct tcctcaccac tgcccttcct tcattttggc atgctcctcc   162060
gcccccgagt tgacagccat agctctctct cctgccacca gtgtcacatg atcgaggaag   162120
aaggcaactt caaaaagact gggtccccct tccactcccat ctcttcagtg agctgctagg   162180
acacccagca gaacttcccc actccacact gcaatctcag ggatcttagt cacggggctt   162240
tccaccatgt ctccacctgg aaaccagtca tggccattcc ttcttacatc tgctcttttc   162300 catcttttc ttctcctcct gttcacccgc ccttactctt gtggcgccct atggatatgc   162360
gctccatagc aaatgattct ttatatctta cggtattcta gtgagctggc acatgtggct   162420
tctggtttcc tctctctgga actagacatg acctctgtgg gagggaggat taaatgcacc   162480
ctacagtctg aggctgcatg atgacatcac tcatcacaat gatgctttct atgtctgaat   162540
cctattcctt tataacccct ttcaagctcg ttcagagagt atttcacaca atccatgtgc   162600
tcatcttaaa agccaaggac ccagaggagt ctcagcattg ccaaaaagtc ccttcaccca   162660
gcctggccag aggcagtgcc tggtccatgt gtatggacta tggcacttca attgcatgga   162720
aatactcttg gaatgaacaa aataccaatc catgaaaaag cattattgaa gtctaagtta   162780 tttttgaat catattttgt taatcaacaa attgaaaaat actcattata tggagaggtc   162840
cagataaagc ctcaatttta aaaatgagg aaaagtgtgc ctggtagggg actggggaga   162900
gcttgagaaa gttggaaacg ttgccttaga agcctgtttt ttctccttt agaagctaca   162960 tagtgtctca ctttccaaga tcattctaca agatgtcagt gcactgaaac atgcagggc   163020 gtgttgagtg ccaaggccat ggaatctgtc agcaacctca cccttccttg ttcctccacc   163080
tcattccagg cctaagatcc cgtccatcgc cactgggatg gtgggggccc tcctcttgct   163140
gctggtggtg gccctgggga tcggcctctt catgcgaagg cgccacatcg ttcggaagcg   163200
cacgctgcgg aggctgctgc aggagaggga ggtgagtgcc agtcctgggt gggctcagga   163260
gccctcgcac cccgacagga acaagggcca gccccgagaa cgggccatta gcagttgtgt   163320
atgttagata cataattgta ttatgatgca gaaagaatct ctgaatgtgc agttataccc   163380
agttggtgac atgttggtac atccatccga ggaaatggca atgttctag gctgcaccct   163440 tcaatgtcca caaagctgtg tggcatctgc ttaggacccg gtgcctgtgt gtgcatagga   163500
gggaggccag gaagcctggc tgttgatccc atgctggcac tgtggcgaag gcgagagatt   163560
cctgctttgg aaaacaccat tgtccacaca gtggctttgt ccatgatgga cttcgccaca   163620
gcccagtcct gtgctggaag ccatgttctc tggaaagagc aacccagcgg ctcataagca   163680
taagcgcgtg tgatgtgccc caaccaaacg accgccatgc acaacttccc taccggagtt   163740
ttcaatccag ttaataggcg tggaaacaga catagaaatt gtgtttgttg aaaggtagct   163800
gttcagttaa agaacacctg tatcagagcc tgtgtttcta ccaacttctg tcaagctctg   163860
tagagaaggc gtacatttgt ccttccaaat gagctggcaa gtgccgtgtc ctggcaccca   163920
agcccatgcc gtggctgctg gtcccctgc tgggccatgt ctggcactgc tttccagcat   163980
ggtgagggct gaggtgaccc ttgtctctgt gttcttgtcc cccccagctt gtggagcctc   164040
ttacacccag tggagaagct cccaaccaag ctctcttgag gatcttgaag gaaactgaat   164100
tcaaaaagat caaagtgctg ggctccggtg cgttcggcac ggtgtataag gtaaggtccc   164160
tggcacaggc ctctgggctg ggccgcaggg cctctcatgg tctggtgggg agcccagagt   164220
```

```
ccttgcaagc tgtatatttc catcatctac tttactcttt gtttcactga gtgtttggga  164280
aactccagtg ttttccccaa gttattgaga ggaaatcttt tataaccaca gtaatcagtg  164340
gtcctgtgag accaattcac agaccaaagg cattttatg aaaggggcca ttgaccttgc   164400
catggggtgc agcacagggc gggaggaggg ccgcctctca ccgcacggca tcagaatgca  164460
gcccagctga aatgggctca tcttcgtttg cttcttctag atcctctttg catgaaatct  164520
gatttcagtt aggcctagac gcagcatcat taaattctgg atgaaatgat ccacacggac  164580
tttataacag gctttacaag cttgagattc ttttatctaa ataatcagtg tgattcgtgg  164640
agcccaacag ctgcagggct gcggggggcgt cacagccccc agcaatatca gccttaggtg 164700
cggctccaca gccccagtgt ccctcacctt cggggtgcat cgctggtaac atccacccag  164760
atcactgggc agcatgtggc accatctcac aattgccagt taacgtcttc cttctctctc  164820
tgtcataggg actctggatc ccagaaggtg agaaagttaa aattcccgtc gctatcaagg  164880
aattaagaga agcaacatct ccgaaagcca acaaggaaat cctcgatgtg agtttctgct  164940
ttgctgtgtg ggggtccatg gctctgaacc tcaggcccac cttttctcat gtctggcagc  165000
tgctctgctc tagaccctgc tcatctccac atcctaaatg ttcactttct atgtctttcc  165060
ctttctagct ctagtgggta taactccctc cccttagaga cagcactggc ctctcccatg  165120
ctggtatcca ccccaaaagg ctggaaacag gcaattactg gcatctaccc agcactagtt  165180
tcttgacacg catgatgagt gagtgctctt ggtgagcctg gagcatgggt attgttttttg 165240
gtatttttg gatgaagaaa tggaggcata aagaaattgg ctgaccctta tatggctggg   165300
atagggttta agccccttgt tatttctgac tctgaaactt gcattcaatt cactccacca  165360
agttatctca tctttgaaat ggcttttttt aaaggtgcct agaatatgat ggcgtgcagt  165420
ctataaactg ttgcccacct tctgtacttt ctctcagaat aattcacatt cttctccagt  165480
gtctgttgat tgttactttg tggaataagt tcttggaaaa ttccacaaga ttattgttat  165540
cttcttacta ccaattctat tgaactttct ccaccttctc tgggccttcc ccagccagtg  165600
gtgggaagat gctggctgga gtctgacaga gcctcttcta cactggcctg ggcttgctgt  165660
gagttggtgg aaacctttgc tcttgtccca acacagagca agtgaaagag gaggtcaagg  165720
ggctcaggca gcggactagg gaagcagaat cgaggaaaag gaaaaatggc tgacttatta  165780
cctcaaaact ctagagaatt tagttgatct tacagccaag aaggacaaaa gccagagagt  165840
aatatcctcc gcctcatgtc taacccacag aatacatagc aagtaaagag aacatgggcc  165900
tttataaaaa tgtcttaaga tacaattttt taattggagg aaatctacag tttaattttc  165960
tctgggcagc ttttcttcct tttattatag tagggaaat cccatgttga tatacttcta   166020
aatgaaagat gatgaattga tataatacaa taaaaaatct gtaaaattga tgatatactt  166080
atcaagaaaa attagctttc atttttaacgg tttacaaatt gagtcaagtc ctagtaacaa  166140
aatgttaagt ctattaacat aaccacaaga aatacaggaa gacgggcaat ctgtgaagcc  166200
tttcacttac aatctctggc ccctcacctg tgctgtgtag gaaaatcttt gtgcacaatt  166260
tgcttcctta attcattttt tattcattca acacattcta ataaattata caaaatcatg  166320
ttgaaatgtg aatttcagtg gtatttataa atgcagtgtg aggagggttt ggatgtattc  166380
taagacaata gttgtgcttt gggaaggaag cagtgttcac tgaaaagtgc ccccaggacc  166440
ttttaattgg aggaaatatg cttctgtgga gttggaaatg gggtagaaga tagataaggt  166500
caaggcttaa aagttaagtg cacccaacat ctgaagcgtc catgggcctg gcatggtggc  166560
```

```
tttcgcctgt aatcccagca ctttgggagg ctgaggcagg aggatccctt gagcttagga    166620
gtttgagacc agcctgggca acatactgag acccagtctc tacaaaaaat aaaaaattag    166680
ctgggtgtgg tgtctcatgc ctgtagtccc agccactcag gagatgggaa gatggcttga    166740
gtccaggaga tctaggctgc agtgagctaa aatctcacca ctgcactcca gcctgggtga    166800
caaagcaaga ccctgctcaa aaaaatagtt agatataaat attaatatag atacctatat    166860
atatctgaat atagatatct atatatactc tgtatatagt tatttagata tataaatata    166920
tatgatatat atttagagag atatatattt agagagatat atatttagag atttatatat    166980
attttatata tatttagaga tatatatctc taaatatata tctctctcta aatatatata    167040
tatctctctc taaatatata tatatcccta aatatattaa ataaataaaa gaaataaaag    167100
aaagctcagt ttggcctcct gcttgtcctg tctcctcatc ccctcttccc cctccatcat    167160
tttatttcct tgccccatgt ttcttcactg cggccatgtc cccctcctc tccaatgatg    167220 gatgtcatgt ctgctgcagt cagagggcga caagcctgga gtgttccctg aagcctgtgg    167280
tttgtggttt gtcctgcagc tcaggctgcc caggcctcac cagcaatcct ggcgggcagg    167340
gcaccacact gggatggaga gggggaagct ggaggaggca ctttctggta aagaaagcaa    167400
aagccagcag tgcccaggcc aatttcaaca gggagttaaa tagcaccta atcctgtggc     167460 aggacagctc atggggccat gtgtgctctt agaaagactc acatgcacgc atgcacggca    167520
gcaatgactc catactcacg ttccctgca gacaccaggc ccccacagcc ggcacacaca    167580
ctgcagcccc agttccatgt tgctagcagt ggcttagtga atgagtaaag ttcttaaaat    167640
gcaggggaca cctgcccttc attcataagg ctggacgtac acctctcctt aaggagttca    167700
agagctagtg gaatcccaat tcatacggta gagccattca cagatgagag agacaagcca    167760
gaaggaagga accaaaagtc atgtcagcag ttaggacaaa ataacaggct ttcaaggtca    167820
caaagcctca gggacactcc tgcggtggga ctgggctagg agccatgggg gctccaactg    167880
tgcgctctgc ctgccagcct gtgggtgctg ggctccacg aagattgttg tggaatacca     167940
agcatgcttg ctgtaggtca cggtgcacgt ttactacttc caagacaaac agccgagaac    168000
aaagctcgct ttagcttctg cgtacaccga acgggacaca cgactgaaca gcgttcccat    168060
tgtgcctgct gggtggggag gaagtgatgg cccagtgggt ctatcagatg ttagtaggat    168120
ggggcctggc ggggctccag gctctgtgtg gccgacaccc acgcccccg ctctgctccc     168180 cattcccagc cccaggtcag ccctgcgagg ccctgcagca gatgggctgc tcaaactgct    168240
ctggtttgca gattttctt ccctctcaaa tgaatacaat atgttttcaa gtctcaacca     168300
gatcttgaga aaataggaag agccagaggg tttctttggt gttatggttg tacagcttcc    168360
cagactccgg gggagagatg tgatttgtgc tttctggcaa tcccatggcg tattaaattt    168420
tcataggctt tccagtttaa atttagggta ggcaatggaa gggaacgcaa aacagatttc    168480
taggtgtact gtgtgtgtgt ctcccacgtc taaagtctgt taactggagc acccaacagg    168540
ccccacaggc tgccttcaca cagaggacct ggggcgcctc cgacccattg gggtgagcag    168600
tgggccatgg agggagccag ggtcaggaga cctggttgtg ggcctgacct gaccctgctc    168660
agggtggcct caggtgggcc gttcacctcg tcagcctcag cttaccctct gactacagtg    168720
acctcagaca aaatacgctt cctggccctg tccagttctg acttttata aacaagcact      168780 tatccaagtt aaagggatat tttcaatatc tactgagtcc acagatatta aatatctcct    168840 ctcttctttta aaattgtggc attatctttta gaatataaaa ggaaataac acacactctc     168900 cttgaaaata gagagcctaa acactctgca ggaaatattt aaagctatag ttttttgtttg     168960
```

```
tttgtcttga atgcaagtgg cctggacttt gacttgcttt gagtctttga ccttcatgac 169020
ttcagtacag ttcaaccctg acagttttga agtaggtatg tgcctagatc tgccctagtc 169080
cctgctggaa tgttgaagaa gcaaaggtcc aggccctcag agcacttgcc acgtacttgc 169140
caacagatac ggggcggaga cttgagtcaa cgtaagagca agtgtgtgcc gggtgatccg 169200
acactgcaga gcgccagcta gaccctaagc gtgtgctagg ggctgaccaa gccgttcttt 169260
cctcaaaaac ttggtgggga gggtattttt aaaatcacac aaatatttaa gtacagatta 169320
tgatgactgc ctcaaagcag tggctcttca gcttcatcaa gcttcagagt ccagagggtt 169380
tgttcatatg gaaggctagg cctgtctcct gcatttcacc ctcttggcct gggggcggga 169440
cccaagaatg tgtggctcta aaaggttccc aggcaatgct gaggctgctt tctgaaggaa 169500
aaactgcaag ataccaggag agtttcattt agattgaaga gtcgaggaag gctcctctga 169560
gaaagagtct gctaaggaag gaggaggtgg gttctgggga cagaggttct cccgtgggta 169620
agggtggagg gaagctctcc tggggagaag gtgggcagga ggaccagagg ctggagggag 169680
gagggcagtc agcctcgggg cttcccagga acagggacgg ccagggcagg gtttagggca 169740
aggaaagcgt gtgagcatat ttgtatttta gtaaatattt acagtttgcc ctccatgtct 169800
gcagtttcat atccatggat tcaatcaacc acaatgaaaa acgttgggga aaaaaattgc 169860
atcggtactg aacatatacg gactttttt cttgtcatta ttccctaaac aatacagcat 169920
aacaattatt cacatagcat ttgcactgta ttaggtacta taggtaatca ggagatgctg 169980
tagatgggag gatgtctgta ggttacacac aaatgctgtg ccactttata tcagggcttt 170040
gagcatcctc acattttgat atttaaggga ggtcctggaa ccaattcccc agatactgag 170100
ggtccactgt ctgtgtcccc tcgccccacc ttgcctttgt ctcctgtctc ctatctccac 170160
cctgcctccc gccagcctgt tgctcctgac ctgcccgggc accctggagc agcaccctat 170220
ctcagagcct ggctcagtgt gttcacttct gcagagaaac taacttgccc aagtccacac 170280
tcaaaacata ggcattgctg agatgtgaaa agcagctgtg gatgctttct gctacagtct 170340
gtgtgttctt ttccatatct gaataaaagg tcaccaccat ttgtatttta aagagaaaga 170400
gaatttatgg gtgaaaattg gggattccct cattctcagt cagacagaaa agagggcccc 170460
attgtgtgcc tgattgcaaa taaatttagc ttcctcagcc caagaatagc agaagggtta 170520
aaataaagtc tgtatttatg gctctgtcaa aggaaggccc ctgccttggc agccagccgg 170580
aattagcagg gcagcagatg cctgactcag tgcagcatgg atttcccata gggagcctgg 170640
gggcacagca cagagagacc acttctcttt agaaatgggt cccgggcagc caggcagcct 170700
ttagtcactg tagattgaat gctctgtcca tttcaaaacc tgggactggt ctattgaaag 170760
agcttatcca gctactcttt gcagaggtgc tgtgggcagg gtcccagcc caaatgccca 170820 cccatttccc agagcacagt cagggccaag cctggcctgt ggggaaggga ggcctttctc 170880
cctgctggct cggtgctccc cggatgcctt ctccatcgct tgtcctctgc agcacccaca 170940
gccagcgttc ctgatgtgca gggtcagtca ttacccaggg tgttccggac cccacacaga 171000
ttcctacagg ccctcatgat attttaaaac acagcatcct caaccttgag gcggaggtct 171060
tcataacaaa gatactatca gttcccaaac tcagagatca ggtgactccg actcctcctt 171120
tatccaatgt gctcctcatg gccactgttg cctgggcctc tctgtcatgg ggaatcccca 171180
gatgcaccca ggagggcccc tctcccactg catctgtcac ttcacagccc tgcgtaaacg 171240
tccctgtgct aggtcttttg caggcacagc ttttcctcca tgagtacgta ttttgaaact 171300
```

```
caagatcgca ttcatgcgtc ttcacctgga aggggtccat gtgcccctcc ttctggccac    171360
catgcgaagc cacactgacg tgcctctccc tccctccagg aagcctacgt gatggccagc    171420
gtggacaacc cccacgtgtg ccgcctgctg ggcatctgcc tcacctccac cgtgcagctc    171480
atcacgcagc tcatgcccct cggctgcctc ctggactatg tccgggaaca caaagacaat    171540
attggctccc agtacctgct caactggtgt gtgcagatcg caaaggtaat cagggaaggg    171600
agatacgggg aggggagata aggagccagg atcctcacat gcggtctgcg ctcctgggat    171660
agcaagagtt tgccatgggg atatgtgtgt gcgtgcatgc agcacacaca cattcctttta   171720 ttttggattc aatcaagttg atcttcttgt gcacaaatca gtgcctgtcc catctgcatg    171780
tggaaactct catcaatcag ctacctttga agaattttct ctttattgag tgctcagtgt    171840
ggtctgatgt ctctgttctt atttctctgg aattctttgt gaatactgtg gtgatttgta    171900
gtggagaagg aatattgctt cccccattca ggacttgata acaaggtaag caagccaggc    171960
caaggccagg aggacccagg tgatagtggt ggagtggagc aggtgccttg caggaggccc    172020
agtgaggagg tgcaaggagc tgacagaggg cgcagctgct gctgctatgt ggctggggcc    172080
ttggctaagt gtccccctt ccacaggctc gctccagagc cagggcgggg ctgagagagc     172140
agagtggtca ggtagccctg cctgggtgct ggagacaggc acagaacaac aagccaggta    172200
tttcacagct ggtgcggacc cagaaagact tctgcttttg ccccaaaccc ctcccatctc    172260
catcccagtc ttgcatcagt tatttgcact caacttgcta agtcctattt ttttctaaca    172320
atgggtatac atttcatccc attgacttta aaggatttgc aggcaggccc tgtctctgag    172380
aatacgccgt tgcccgtcat ctctctccga cagcagggca gggggtccag agatgtgcca    172440
gggaccagag ggagggagca gacacccacc cggcctgggc aggtcctcct cattgcttgc    172500
atccgcctgg ttagcagtgg cagtcagtcc tgccgagtca ttcgtgaggc gctcacccaa    172560
ctccaggcag atgtaaaagg tgacctacaa gaagacaaac aaaaacatct ggagcgctct    172620
tatgccagca tctgcccttg acaccaccag gcaggctgtt gctgggagcc gtggtgcttg    172680
ggtaagctcc ttcccatggc agagctcctg gacgcattg tagaagcagg gaccacctcc     172740
caggataacc agatagcagc acaccctgca cagccccttt tactccagca tcatcgggca    172800
ttgatatctc agctgcagcc acaggcggcc cccagcaccc caggaagtgg ggagcgctca    172860
tgcttctctg agcacaaaaa tcactgaata ttttttgccat tctcatggtc ataacccggg   172920
ccacagagta gaacactcct atcactgttg ttagacagtg gtcctgggag agggtcttgt    172980
gtgcctcgga tgccagggcc tcttttatt gggaggtgct tgttatttct gtgtgtggct     173040
gcatttgttt cccaagactg ccacaacaaa tcatcaccaa cttggtagct caacatagca    173100
cagctttatt ccctcctggc tctggaggcc aggtgtctaa aaggccatgc tcccacaatg    173160
gttctgagga ggatccttcc tgcctctctg gcttctggtg gctccagcat ccctgggctg    173220
tggctgcacc tccccatgtc aacctccgtc ttcacaaggc ttttcctgt gtctctgcaa     173280 ccacaggccc ctctcctttc tcttaataaa gataccagtc attgagtttg aaaattgcta    173340
agagagtctg ttgtaaatct tcttagcaca aaaaaaaatg acagatatgt gaagtggtag    173400
atatattaat tagtttgatt tgatcactcc gctatgtgta taaatgtcaa acaaacatt     173460 gcactccata aatatatata ttaaaaaaga tcccagtcat tgcatttagg acccacccta    173520
aatccaggat gatttcattt caagactttt aactagattt gcaaaacccc atttccaaat    173580
aaggtcacat tctgcagttt tgggtagacg tgaaatgtgg agacactgtg caacccactg    173640
tcttggggag ggggtggtca gcctggggca gatgttgctg ggtgtggagc tacatccact    173700
```

```
catgccctga cctggaaccc agacctgctt ccccagctct cctcctggtt atctgaagca   173760
gggaatggag agcactgccc tccttgccca ggcagtctct atcacctggt tttagtttct   173820
tcttagcaca tattgcccca gaatatctgg ttggtttatg gcttacttga gtttgtgcct   173880
acctgtccca accgggaggt gagccctggc tattccccaa acccggccct gcatgtggga   173940 gctgccttc ctccgttcat cagagggggc aacagtcca cagctgttct taatcatctc    174000
ccagtaaccc ccagctccac aaaggtgact ccttacatgg tggagaggtg gtcgggccat   174060
ccgtgtgaaa tgtgtatgtg accgttttcc ttaaggggca cgtagtcttg gcaggtttcg   174120
ctcaatatag gatgagctca ggactccagt ggactgtgga ttcagatctg gattctggcg   174180
cattcgccgt gtgaacgggg gcacgttgct ggcctgtctg cgcctcgtct cccgactgtg   174240
gagtgtgttc tgcccctttgt ctttctggga ggtagggagg gcagtgagcc ccttcgcatc   174300
gcccaccaca ggcccagcac atggctgatc cccactgagt gttcttttcc tcctttgatc   174360 cccttggct gacctaggtt ggagcagcca ctaaaatata cccagaaaca tcttcctaat    174420
ctacatctgt gccaaccctc attccctggc gcagcatgac catcacatgc ccgccattgt   174480
tcctgatctc tgctgctcat gacctgctct ccagcgctcc ttctcatgct cacattccag   174540
ttggcctgac ctagataagt ggaggtttat ttgaccccaa aaattagcct tctacaaacg   174600
aatataatag tgtccattac agagaataaa cttagtgcgt gtcccattta agcaagaagtt  174660 actgaaagcc tgagtttaag tttccagggc ctgaaagttt tccatgacag ttttctgcat   174720
aatattacct acaatttcaa tctgttattt aaagccattc ttgtgtttgt tgtactttga   174780
ttagctttat tttgatttga agtccttta cattacgggc agttaacgct ttgtctctgt    174840
tagatttgct ttttagttca caagagaaac ctcattcctc tgtatttgaa tagttgcaat   174900
gatggaacag ctgtccctgg agggaaatga aaacagtgat tcccccaaatt gtgacaatag  174960 aaatttgctc ttgggttact tacaatgtat ctgagtatta aaaaattttc tttttaaacg   175020
tttgaagtaa aactacccag aaacacttag tggctgacca gaaactaaac tcctggcatc   175080
ctcaaaatgg gatttattgg cttataaatg tcctgtgttg actcacaaag gcacaaacta   175140
tctaggtaag ttttcttcta aatgttgatg ggagagctgg ccactgttat gcaagtttca   175200
ttgtcctgac taaactgcca aagagattac ataaaattat atcaactaga caaaaggaaa   175260
aaggaaaaaa aacagaggtg tcttgggagg aatccatatg agaccagtag accatgagag   175320
agacatccct tgccatctac aaggaaaatg gattttgttc tccatatgca aaaccatctc   175380
aggagcttgc ggagacacca cttgcttact agccagaaag agcaggtgcc tcctaaattc   175440
cccacacagg agctcacagt ggctttcatg cactgggatt aagttagact taagaaagcc   175500
tgtctactct tcctgggatt tacaagccag ctagtaaatc ccagaataaa tcacacggca   175560
cagtcatcca aagatcccgt catccgtgcc gtttggaaag ccctgctcct gtgccaccct   175620
ctccccgtgg agcctcccat gcccaggact gcagagtcct gccattcaga ctgcaactca   175680
tctcacattc ttccaaacta tttggacaac agagctttct catcacctaa tgcagattac   175740
agtctcacag aattgagtgt tcaggcagac actgatgtgg ttctgtagta cagcaaacaa   175800
tatcagttta cagtcctgag gccaggcctg gtgaacaacg cacggtagcg gtggggcagg   175860
gttctcagaa tgaaactggc ttacacatgg cactctctga ccacaactgt ataagcacca   175920
aactacactt agttccatct atgaggtaaa atttaatgca gatgaacatc aaagaaaacg   175980
tcaaaggctc ctttttacaa gtacgtgggc tacttaattt ggtccaagtc cattttaaaa   176040
```

```
agccctaggt gctttcacgg ctctgctact gacaagaagc cccagtgcct gtgagctgct   176100
aatgggaggg agaggaagat gagctgagtg ggccgggcta tcccgtccac accgggagac   176160
agggaaggag actccaagct ggtggtgcca gcacattcca ggccactcag gcctattcct   176220
aggtgccagg tcacgaaaac cacgctgaca gatcgtgctg tgtgcgtgtc atagcacaca   176280
agcaggactg tgagagagtg aaagtgacac tgggtggagc actgaggaag gccacagtg   176340
tgttggtgga gataggctgt catggagaag agaccctggc ttgctctaca ttgcttccaa   176400
tgcaactgca aggcaggtcc cagagggctc cggccttcgt catccaggtt tgctccctcc   176460
cctcatggct ttcccatcct cagatgagga ctcggcagag cctacccctg ctgactaact   176520
gtggcccag ggtggtgact cagccctgca cctcctgatc ccgtctgcac tgggccagag   176580
aggatgactt acccagcacg ttcacatcac acagctttgt ggattcctag gtccaaggac   176640
cagagatttc agttatgtga gttatttttt ttatttgttc ttgcgtattc cacaaagggt   176700
cgcagctaaa cttaacctaa tgatcacttt agtatatcac taaaaagaca aagctcacag   176760
tgctgttgaa gcacattcat catctttaga cattttgact agttatttct taagcattta   176820
cctgctagtg ttaagcatca catgaaatac atatagaagt aagacaaaat ttcttatctc   176880
cccaagtttg ccaacaaata cagagcagga agggaagcag gtcagagcag gaggcgcagc   176940
tatagtgagg ccaccatgca aggcacaggg agggtgagct ccaagtttga atggaatggg   177000
tctgtcagcc aagcccctg gctctgggaa gatagcagtg aacaagccag atggcccctc   177060
accctccaga gccgtgagtc ctgcagacca acagcgtga caggtccttt ccctgtccag   177120
gaggcctctg tgggtgagag ttggctgcgg acagggcgtg aaggcacttg agggtgggga   177180
agtgactctg actgggagat gctgaggaca gggaggaaac caccagataa gggacactgg   177240
ggaggagggg tggaccctc agggccaagc acatggagcc tcatcacaaa ggcaagatgg   177300
tggccaaatt caaggtcgct gcaaaaggaa tggagaagag agaatagatt tggcatttgg   177360
aggaaatggt gacaatcatg agcacctacc cgggactctc catgggtgct atctctacat   177420
aaactcattc caccctctga ttaatccatt ctacatatgg ggaaacaaag gcatgcggtg   177480
tttacgtcac ttgccaagat ctcaggattt gatccaggtg gcctggttcc atggtgcagc   177540
ctctcagcct gcatggatgc cccagctcag agcatgactc tcaggacagg gtcccagca   177600
gccctccctc cctgagcagc agggtgcccg tgctgcacca cttctgtcta ggaataggac   177660
attctgacac tttcctgcct cttccgaggt ctagcactta ctctatgcct gcctgggaag   177720
gtggcaagct ggcctgagga acagactctt ccatttttta gggagctcaa ggccacagat   177780
gctctgagat ctggagtcca gagacaggag cggaggcttc tcctggtgac cactctgctt   177840
aaaaacttca tcagatccgt agtttcagag cccccctgaa ccccatccct tacctctacc   177900
agttgcaggt gggtctctgg ggtggggctg ccctccccac cagcacccca agggctaaaa   177960
ggttgagggg agaacaccat catttgtaca gggggatc                          177998
```

<210> SEQ ID NO 27
<211> LENGTH: 21
<212> TYPE: DNA
<213> ORGANISM: Homo sapiens
<220> FEATURE:
<221> NAME/KEY: misc_feature
<223> OTHER INFORMATION: EGFR exon 1 forward primer

<400> SEQUENCE: 27
ctcctcgggg agcagcgatg c                                              21

-continued

<210> SEQ ID NO 28
<211> LENGTH: 20
<212> TYPE: DNA
<213> ORGANISM: Homo sapiens
<220> FEATURE:
<221> NAME/KEY: misc_feature
<223> OTHER INFORMATION: EGFR exon 9 reverse primer

<400> SEQUENCE: 28
ccacacagca aagcagaaac                                             20

<210> SEQ ID NO 29
<211> LENGTH: 26
<212> TYPE: DNA
<213> ORGANISM: Homo sapiens
<220> FEATURE:
<221> NAME/KEY: misc_feature
<223> OTHER INFORMATION: EGFR patient 1 breakpoint forward primer

<400> SEQUENCE: 29
catgatgttt aattattaga ggactc                                      26

<210> SEQ ID NO 30
<211> LENGTH: 18
<212> TYPE: DNA
<213> ORGANISM: Homo sapiens
<220> FEATURE:
<221> NAME/KEY: misc_feature
<223> OTHER INFORMATION: EGFR patient 1 breakpoint reverse primer

<400> SEQUENCE: 30
aagcaaggca aacacatc                                               18

<210> SEQ ID NO 31
<211> LENGTH: 24
<212> TYPE: DNA
<213> ORGANISM: Homo sapiens
<220> FEATURE:
<221> NAME/KEY: misc_feature
<223> OTHER INFORMATION: EGFR patient 7 breakpoint forward primer

<400> SEQUENCE: 31
tctaggccgc aatgtggaca atac                                        24

<210> SEQ ID NO 32
<211> LENGTH: 24
<212> TYPE: DNA
<213> ORGANISM: Homo sapiens
<220> FEATURE:
<221> NAME/KEY: misc_feature
<223> OTHER INFORMATION: EGFR patient 7 breakpoint reverse primer

<400> SEQUENCE: 32
acagtggctc atgcctgtaa tctc                                        24

<210> SEQ ID NO 33
<211> LENGTH: 26
<212> TYPE: DNA
<213> ORGANISM: Homo sapiens
<220> FEATURE:
<221> NAME/KEY: misc_feature
<223> OTHER INFORMATION: Fusion of exon 1 and exon 2 in WT EGFR

<400> SEQUENCE: 33
ggaggaaaga agtttgccaa ggcacg                                      26

```
<210> SEQ ID NO 34
<211> LENGTH: 29
<212> TYPE: DNA
<213> ORGANISM: Homo sapiens
<220> FEATURE:
<221> NAME/KEY: misc_feature
<223> OTHER INFORMATION: Fusion of exon 7 and exon 8 in WT EGFR

<400> SEQUENCE: 34
tgaagaagtg tccccgtaat tatgtggtg                                    29

<210> SEQ ID NO 35
<211> LENGTH: 28
<212> TYPE: DNA
<213> ORGANISM: Homo sapiens
<220> FEATURE:
<221> NAME/KEY: misc_feature
<223> OTHER INFORMATION: Exemplary fusion of exon 2 and exon 8 in
      patient with EGFRvIII mutant gene

<400> SEQUENCE: 35
ggaggaaaag aaaggtaatt atgtggtg                                     28
```

METHODS FOR DETECTION AND QUANTIFICATION OF EGFRVIII IN THE PERIPHERAL BLOOD OF GBM PATIENTS

RELATED APPLICATION

This application claims priority under 35 U.S.C. § 119(e) to U.S. Provisional Application Ser. No. 61/972,461, filed Mar. 31, 2014, which application is hereby incorporated by reference in its entirety.

TECHNICAL FIELD

The presently disclosed subject matter relates to methods and kits for monitoring the therapy of a patient suffering from glioblastoma multiforme (GBM). More specifically, the presently disclosed subject matter relates to methods and kits for monitoring the therapy of a GBM patient that is positive for the epithelial growth factor receptor vIII (EGFRvIII) gene.

BACKGROUND OF THE INVENTION

Glioblastoma multiforme (GBM) is the most aggressive brain tumor in adults and remains incurable despite multi-modal intensive treatment regimens. Brain tumors can be difficult to biopsy due to their high-risk location relative to vital structures of the brain or patient related co-morbidity. A very limited number of patients are re-biopsied or re-resected when they relapse after the initial therapy. The management of these patients also poses many problems as follow up of patients with brain tumor is limited to radiological techniques such as magnetic resonance imaging (MRI). Even with the addition of the last generation of imaging studies (spectro-MRI, PET-CT), clinical assessment of tumor progression versus pseudo-progression remains difficult. This can pose serious delays in treatment decision and result in harm to the patient. Management of patients with brain tumor is problematic as it is limited to radiological techniques and clinical assessment of tumor progression versus pseudo-progression remains difficult.

The use of tumor-specific rearrangements to monitor the status of the disease may improve the clinical management of brain tumor patients. EGFRvIII is a truncated extracellular mutant of the epithelial growth factor receptor (EGFR) commonly found in GBMs that confers enhanced tumorigenic behavior. GBM patients testing positive for EGFRvIII have a bleaker prognosis than those who don't. Virtually no EGFRvIII-positive patient survives two years, versus about 15% of those who are EGFRvIII-negative. EGFRvIII is tumor specific and is present in about one third of brain tumor cases. Thus, it potentially represents an ideal mutation to follow and quantify in the peripheral blood of patients on treatment. However, detecting this mutation in the genomic DNA is challenging as the deletion breakpoint is different from one patient to another. Thus, the need exists for new methods and kits that allow for the detection and monitoring of EGFRvIII in patients suffering from GBM.

SUMMARY

Accordingly, it is an object of the present invention to provide method for monitoring the therapy of a patient suffering from GBM, comprising: (a) subjecting a sample from the patient comprising genomic DNA to long range polymerase chain reaction amplification of epithelial growth factor receptor vIII (EGFRvIII) gene, wherein the long range polymerase chain reaction amplification utilizes a plurality of forward primers corresponding to a DNA sequence in intron 1 of an epithelial growth factor receptor (EGFR) gene and a reverse primer that corresponds to a DNA sequence in exon 8 of an EGFR gene, such that if the sample comprises genomic DNA comprising EGFRvIII, a PCR product is formed, and if the test sample does not comprise genomic DNA comprising EGFRvIII, a PCR product is not formed, wherein the plurality of forward primers are comprised within the base pairs defining intron 1 of the EGFR, each primer being separated by at least 5 kb from each other, and wherein the presence of PCR product is indicative of a presence of EGFRvIII in the test sample, and the absence of PCR product is indicative of an absence of EGFRvIII in the test sample; (b) identifying deletion breakpoints in the PCR product and designing amplification primers that hybridize to priming sites that flank the breakpoints, wherein the amplification primers are designed to yield a PCR fragment of about 300 base pairs; and (c) amplifying DNA from body fluid samples of said patient using the amplification primers to form an amplified DNA fragment of EGFRvIII.

In another embodiment, a kit is provided, the kit comprising a plurality of forward primers corresponding to a DNA sequence in intron 1 of an EGFR gene and a reverse primer that corresponds to a DNA sequence in exon 8 of an EGFR gene, wherein the plurality of forward primers are comprised within the base pairs defining intron 1 of the EGFR gene, each primer being separated by at least 5 kb from each other.

In another embodiment, a kit is provided, the kit comprising one or more amplification primers that hybridize to priming sites that flank breakpoints in EGFRvIII, wherein the one or more amplification primers are designed to yield a PCR fragment of about 300 base pairs.

These and other objects, features, embodiments, and advantages will become apparent to those of ordinary skill in the art from a reading of the following detailed description and the appended claims.

BRIEF DESCRIPTION OF THE DRAWINGS

FIG. 1 depicts the data analysis pipeline used that allows detection of structural variations, single nucleotide polymorphisms, as well as copy number variations.

FIG. 2. A schematic representation and detection of EGFRvIII deletion. FIG. 2A depicts that genomic DNA structure of EGFRvIII mutant gene compared to wild type EGFR gene. FIG. 2B depicts EGFRvIII protein showing the ligand binding domain deletion.

FIG. 3. Detection of EGFRvIII genomic deletions and determination of the breakpoints.

FIG. 4. Confirmation of the EGFRvIII deletion using next generation sequencing.

FIG. 5. Detection and tracking of the EGFRvIII deletion in the plasma.

DETAILED DESCRIPTION

Figure 1:
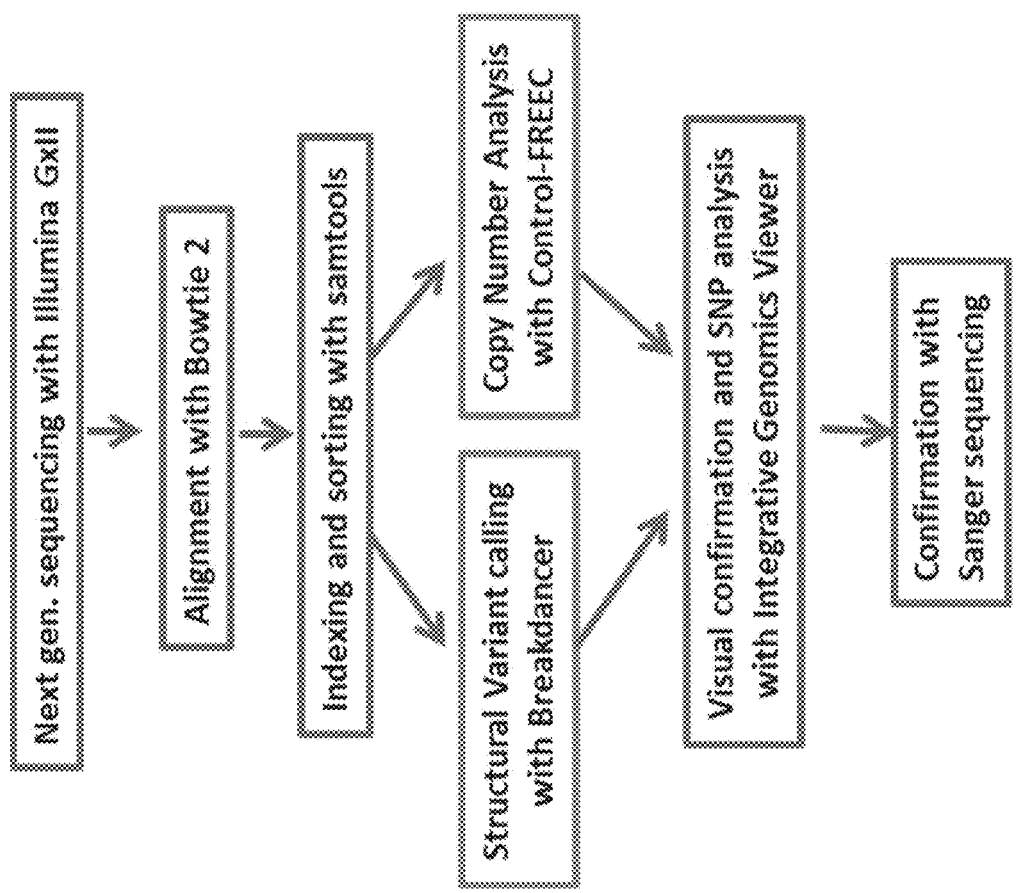
FIG. 1. Whole genome sequencing data analysis pipeline.

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not necessarily limited to these preferred aspects.

Unless defined otherwise, all technical and scientific terms used herein have the same meaning as commonly understood by one of ordinary skill in the art to which the presently-disclosed subject matter belongs.

There is an urgent need for sensitive personalized biomarkers to accurately monitor residual and recurrent tumors and enhance the clinical management of GBM patients. No biomarkers are currently available to follow brain tumor patients on treatment. There is a strong interest in exploiting somatic mutations, which occur exclusively in the tumor, to develop such biomarker. One such mutation is the EGFRvIII deletion. Approximately 33% of all high-grade gliomas express EGFRvIII, and it is a bona fide tumor-specific antigen with potent oncogenic properties (20). It results from an in-frame deletion of 801 bp spanning exons 2 to 7 of the coding region of EGFR and leads to ligand-independent tyrosine kinase activity that activates persistent downstream phosphatidylinositol 3-kinase (PI3-K) pathway. The use of genomic DNA to detect the EGFRvIII mutation is complex due to the presence of several recombination sites in intron I (123 kB) and in intron 7 of EGFR gene. These sites are involved in DNA recombination events that generate genomic deletions of varying sizes leading to structural differences between GBM patients. Thus, detecting this mutation in the genomic DNA is challenging as the deletion breakpoint is different from one patient to another, although the mRNA is similarly spliced in every patient and the resulting truncated protein is the same in every patient.

To address this problem, we used a long range PCR amplification strategy that allows detection of all possible EGFRvIII deletions. The presently disclosed data demonstrates that our long range PCR strategy can be successful in detecting EGFRvIII deletion without the need to sequence the whole genome of the patient, which can be costly and time consuming. These deletions were confirmed using next generation sequencing in one of the EGFRvIII patients. Additionally, we developed a strategy to detect EGFRvIII mutation in the circulating tumor DNA and investigated the utility of tracking the tumor-derived EGFRvIII mutation in the peripheral blood as a way to monitor GBM tumor dynamics in patients on treatment. The presently-disclosed data also demonstrates that quantification of the EGFRvIII mutation in the plasma can be a useful tool to monitor brain tumor dynamics in patients on treatment. We collected blood just before surgery and 3 weeks after surgery. The blood was used to isolate both plasma for circulating DNA extraction and white blood cells (WBC) for extracting the constitutional DNA control. Genomic DNA (gDNA) from the tumor was extracted, and together with gDNA from WBC, was used to determine the location of the EGFRvIII deletion. The deleted area was confirmed using next generation, paired end sequencing. Sanger sequencing was used to determine the breakpoints and primers spanning the breakpoints were used to PCR amplify through the deleted fragment in the gDNA from both tumor and plasma. The data suggest that the amount of circulating mutant EGFRvIII DNA correlates with the status of the tumor and could be used as a noninvasive biomarker to monitor disease status in patients on treatment.

In some embodiments of the presently-disclosed subject matter, a method for monitoring the therapy of a patient suffering from glioblastoma multiforme (GBM) is provided. In certain embodiments, the method comprises subjecting a sample from the patient comprising genomic DNA to long range polymerase chain reaction amplification of epithelial growth factor receptor vIII (EGFRvIII) gene. A "patient" refers to an individual that is suffering, or suspected to be suffering, with cancer. In specific embodiments, the individual is suffering, or suspected to be suffering, from GBM. The term "samples" refers to any biological material collected from an individual, and can include whole blood, plasma, serum, lymph, spinal fluid, tissue, and in particular, tumor containing tissue, such as tissue derived from a biopsy or obtained after surgery.

PCR amplification is a well-known tool in the art for amplification of nucleotide sequences. In certain embodiments, the PCR is real time PCR technique allowing simultaneous detection of the amplified product. Real time PCR techniques are well known in the art. The primers used in PCR are designed to anneal to the denatured target DNA sequence strands in a position and orientation such that the extended primers are complementary copies of the target DNA sequences. On subsequent amplification cycles, the extended primers can also serve as targets for amplification. Long range PCR is also well-known in the art, and utilizes amplification conditions which improve target strand denaturation (e.g., higher denaturation temperatures, addition of cosolvents), and which protect DNA from degradation; utilizes longer extension times; and minimize incorporation of erroneous nucleotides by utilizing polymerases having exonuclease activity to reduce mismatches, thereby enabling amplification of extended strands of DNA. Long range PCR has been used for the sequencing and analysis of EGFRvIII deletions (Frederick. L, Eley. G, Yang-Wang. X, James. C (2000); "Analysis of genomic rearrangements associated with EGFRvIII expression suggests involvement of Alu repeat elements". *Neuro Oncology;* 2000; 2:159-169), the entire teachings of which are incorporated herein by reference.

In some embodiments of a method for monitoring the therapy of a patient suffering from glioblastoma multiforme (GBM), the long range polymerase chain reaction amplification utilizes a plurality of forward primers corresponding to a DNA sequence in intron 1 of an epithelial growth factor receptor (EGFR) gene and a reverse primer that corresponds to a DNA sequence in exon 8 of an EGFR gene. DNA/RNA is within the scope of our recitations if they are within 98, 95, 90, or 80% sequence homogeneity with the sequences set forth as SEQ ID NO 26 (*homo sapiens* EGFR sequence, GenBank Accession #AC006977), as well as the sequence for intron 1, exon 1, intron 7, and exon 8 of human EGFR, as is known in the art (see for e.g., Reiter, J. L. et al (2001); "Comparative Genomic Sequence Analysis and Isolation of Human and Mouse Alternative EGFR Transcripts Encoding Truncated Receptor Isoforms". Genomics; 2001; 71: 1-20), the entire teachings of which are incorporated herein by reference).

Figure 3A:
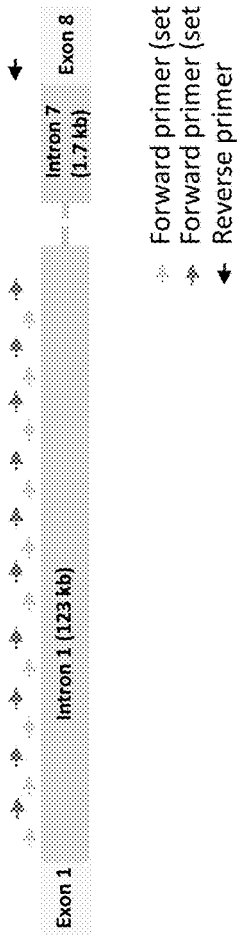
FIG. 3A depicts a schematic representation of the EGFRvIII genomic DNA showing the loss of exons 2 through 7, the location of Alu sites in introns 1 and 7 involved in recombination, and a schematic of the forward primers used in the long-range PCR-based strategy that span the whole intron 1 and a reverse primer in exon 8.

In certain embodiments, the plurality of forward primers is comprised within the base pairs defining intron 1 of the EGFR, with each primer being separated by at least 5 kb from each other (as is schematically depicted in FIG. 3A). As is known in the art, a primer refers to an oligonucleotide that is capable of serving as an initiation point for nucleic acid synthesis during PCR or long-range PCR, under appropriate conditions. Primers can be prepared by a variety of methods that are well known in the art, including chemical synthesis. As is known in the art, a forward primer is a primer that hybridizes to the non-coding strand of the target DNA and forms the 5' end of the amplified product of the coding strand), and a reverse primer is a primer that hybridizes to the coding strand of the target DNA and forms the 5' end of the amplified product of the non-coding strand. A primer "corresponding to" a DNA sequence is a primer that has the same nucleotide sequence as the DNA sequence, or that is sufficiently complementary to the DNA sequence that it hybridizes under PCR (including long-range PCR, real time PCR, etc.) conditions to the DNA sequence.

In certain embodiments of a method for monitoring the therapy of a patient suffering from glioblastoma multiforme (GBM), if the sample comprises genomic DNA comprising EGFRvIII, a PCR product is formed, and if the sample does not comprise genomic DNA comprising EGFRvIII, a PCR product is not formed. In some embodiments, the presence of PCR product is indicative of a presence of EGFRvIII in the test sample, and the absence of PCR product is indicative of an absence of EGFRvIII in the sample. Thus, in certain embodiments, the primers are designed such that no PCR products are produced in the absence of EGFRvIII. For example, the primers will yield PCR products of a certain size in the presence of the EGFRvIII, and will yield no PCR products in the absence of EGFRvIII. Alternatively, the primers can be designed such that the PCR products obtained from the primers will differ in size, depending on the presence or absence of EGFRvIII. That is, in the presence of EGFRvIII, the primers will yield PCR products of a certain (first) size, and in the absence of the EGFRvIII, the same primers will yield PCR products of a (second) size that is detectably different from the size of the PCR products in the presence of EGFRvIII (the first size). The detection of EGFRvIII is indicative of the presence of precancerous or cancerous lesions.

The term, "PCR products," refers to copies of the target DNA sequences that are produced during PCR amplification (i.e., DNA which has been amplified during the PCR process). If no DNA has been amplified during PCR, no PCR products will be generated. Analysis of the PCR products includes detecting the presence (or absence) of detectable PCR products; in a preferred embodiment, analysis of the PCR products includes determining the size of any detectable PCR products. A detectably different size indicates that the differences in the sizes of the products can be identified, using standard techniques as known in the art. The PCR products can be detected by a variety of methods that are well known in the art. For example, gel electrophoresis (e.g., agarose or acrylamide gel electrophoresis), or HPLC, can be used to separate PCR products based on the size of the DNA, and can followed by detection of the size fractionated DNA by methods such as staining (e.g., with ethidium bromide), or hybridization of labeled probes. Detection can also be conducted directly during amplification, such as with real-time PCR and melt curve analysis using cyber green as a labeling agent.

In some embodiments of a method for monitoring the therapy of a patient suffering from glioblastoma multiforme (GBM), the plurality of forward primers comprise one or more primers for detecting breakpoints in EGFRvIII selected from the primers set forth in Table 1. "Breakpoints" are one or more boundaries of a somatic rearrangement, and such breakpoints can be specific markers for the tumor. Identifying a boundary can be accomplished by a number of techniques known in the art. For example, one technique involves sequencing and/or analyzing two different portions or ends of a single fragment of genomic DNA from a tumor. The two portions or ends may be separated by any distance, from immediately adjacent up to 1 kb, 1.5 kb, 2 kb, or 3 kb, for example. The ends may not be the literal ends of a fragment, but may be close to the ends or merely two non-overlapping portions. The sequence of the two ends may be determined separately, for example from either end, or the sequence can be determined in one direction and analyzed for separate, non-overlapping segments of differing copy numbers.

In some embodiments of a method for monitoring the therapy of a patient suffering from glioblastoma multiforme (GBM), the method further comprises identifying deletion breakpoints in the PCR product and designing amplification primers that hybridize to priming sites that flank the breakpoints. The amplification primers are designed to yield a PCR fragment of about 300 base pairs. The identification and design of amplification primers that hybridize to priming sites that flank breakpoints is described in detail, for example in U.S. Pub. No. 2013/0120645, the entire teachings of which are incorporated by reference herein.

In certain embodiments, the method further comprises amplifying DNA from body fluid samples of said patient using the amplification primers to form an amplified DNA fragment of EGFRvIII. The term "body fluid" can include whole blood, plasma, serum, and spinal fluid. In more particular embodiments, the method further comprises determining the amount or proportion of the amplified DNA fragment of EGFRvIII in the body fluid samples of said patient. Thus, the methods can be used to obtain qualitative or quantitative results. The quantitative results can be absolute amounts or relative amounts, for example, compared to a non-rearranged sequence on the same or a different chromosome. In particular embodiments, the DNA is circulating DNA, plasma DNA, or serum DNA.

In further embodiments of a method for monitoring the therapy of a patient suffering from glioblastoma multiforme (GBM), the method comprises a streamlined assay based on high-throughput real-time q-PCR. For example, a glass microfluidic chip can be used to carry out continuous-flow, droplet-based PCR reactions. To generate droplets, a syringe pump is used to infuse the aqueous sample into a channel on the chip. To carry out PCR, the chip is mounted on two static heaters that divide it into two thermal zones, a 95° C. zone and a 67° C. zone. The droplets are conveyed through the chip by the flow of oil, and the static thermal zones provide hot start activation and 35 cycles of two-step PCR. The PCR microchip is stationed above an optical system that combines a video camera with a two-wavelength laser excitation and detection system. Using this optical system, droplets are interrogated at specific neckdowns, 100-µm-long regions of the chip where the channel width and depth decrease, forcing droplets into a single file. Since the diameter of the droplets is the same as the width and depth of the neckdowns, only a single droplet can fit through a neckdown at one time, and no droplets can be missed by the lasers. A fluorescent dye, such as Alexa Fluor 594, provides a constant signal in each droplet that is used for droplet detection. In addition to the Alexa dye, a FAM-labeled Taqman probe that is specific to a region of the amplified EGFRvIII sequence is added to the reaction mix. Fluorescence of the FAM dye on the probe is detected under the fluorescence resonance energy-transfer process when released from its proximity to a quencher by the exonuclease activity of the DNA polymerase, providing a fluorescence intensity increase proportional to the EGFRvIII DNA concentration in the droplet, allowing quantification of the EGFRvIII mutant.

The methods can be used for a variety of purposes. For example, patients can be monitored over time to see if a tumor is in remission or is progressing, the methods can be used before, during, and/or after a therapy regimen, the methods can be used to assess surgical efficacy, and the methods can be used to monitor for relapse or recurrence. In some embodiments, the presence of an amount of amplified DNA fragment indicates residual GBM. In certain embodiments, the step of determining is performed with bodily fluid samples obtained from the patient at a plurality of times. In additional embodiments, the plurality of times is during anti-tumor therapy, before and after surgery, during patient treatment to monitor a patient undergoing anti-EGFRvIII therapy, or the plurality of times are to monitor a patient in remission or relapse of GBM. "Therapy" is defined to include a patient undergoing diagnosis for detection of EGFRvIII, as well as patients undergoing surgical tumor resection, and novel anti-EGFRvIII treatments, including but not limited to, vaccines, antibody-toxin conjugates, EGFRvIII-specific tyrosine kinase inhibitors, as well as other treatments that target EGFRvIII or EGFRvIII protein. Therapy also includes patients being monitored over time to see if a tumor is in remission or is progressing. The methods can be used before, during, and/or after a therapy regimen.

Other deletions commonly present in brain tumors can be used the same way we used the EGFRvIII deletion. One such deletion is the CDKN2A in the 9p21.3 region which occurs in approximately 31% to 50% of GBMs and the ERRFI deletion in the 1p36.23 region which occurs in about 35% of GBM tumors. Besides large deletions, single nucleotide mutations in genes such as IDH1, Tp53, and PIK3CA are also common in brain tumors and can be quantified in the plasma.

In further embodiments of the presently-disclosed subject matter, a kit is provided. In certain embodiments, the kit comprises a plurality of forward primers corresponding to a DNA sequence in intron 1 of an EGFR gene and a reverse primer that corresponds to a DNA sequence in exon 8 of an EGFR gene. The plurality of forward primers are comprised within the base pairs defining intron 1 of the EGFR gene, each primer being separated by at least 5 kb from each other. In certain embodiments, the kit further comprises a forward primer for exon 1 of EGFR. In more particular embodiments, the forward primer for exon 1 has the nucleotide sequence (5'-CTCTTCGGGGAGCAGCGATGC-3'). In other particular embodiments of the kit, the reverse primer that corresponds to a DNA sequence in exon 8 of EGFR has the nucleotide sequence (5'-CTTCCTCCATCTCATAGCTGTCGG-3"). In certain embodiments of the kit, the plurality of forward primers are selected from primers set forth in Table 1.

In further embodiments of the presently-disclosed subject matter, a kit is provided that comprises one or more amplification primers that hybridize to priming sites that flank breakpoints in EGFRvIII, wherein the one or more amplification primers are designed to yield a PCR fragment of about 300 base pairs. Thus, the primers to be used in plasma are typically designed within 150 base pairs from each side of the breakpoint.

Preferably, the kits further contain nucleic acid polymerase (including long range high fidelity polymerase), dNTP, buffer, and any other reagents necessary to perform PCR, long range PCR, and RT-PCR, as is known in the art. If required, the kits can further contain a sample containing EGFRvIII as a positive control and/or instructions to use the kit, how to prepare the samples, what kind of samples to use, how to analyze and interpret the results, etc. especially, the test kit can comprise instructions, how to use the test kit for detection of the presence or absence of cancer cells expressing EGFRvIII.

Thus, the test kits according to the present invention, allow determining the absolute concentration or the relative concentration or the presence or absence the amplified DNA fragment of EGFRvIII. The test kit can be used to diagnose the absence or presence of cells expressing EGFRvIII. Further, the test kit can be used to predict the occurrence or to predict the grade or stage of the cancer and/or to predict and/or monitor the success of an anti-therapy EGFRvIII for said cancer and/or predict and/or monitor a relapse of said cancer.

EXAMPLES

The following examples are given by way of illustration and are in no way intended to limit the scope of the present invention.

Example 1

Materials and Methods

Patients and Tumor Samples

Eleven patients newly diagnosed with GBM and planned for surgery, consented to obtain tumor tissue as well as immediate pre-operative blood and 3 weeks delayed post-operative blood. Blood samples were processed immediately for plasma separation and white blood cell (WBC) isolation. Plasma, WBCs and tumor tissue snap-frozen in OCT were stored at −85° C. until used.

RNA Extraction and RT-PCR Amplification

Total RNA was extracted from about 3 mm$^2$ sections using "illustra triplePrep Kit" (GE Healthcare Bio-Sciences Corp). Complementary DNA (cDNA) was reverse transcribed from RNA in 20 µL volume reactions using the "iScript cDNA Synthesis Kit" (Bio-Rad Laboratories, Inc, Hercules, Calif.) according to the manufacture's protocol. The resulting cDNA was used in PCR amplifications in 50 µL volume reactions using "GoTaq Green Master Mix" from Promega Corporation (Madison, Wis.) to determine the EGFRvIII status for each tumor tissue. A forward primer from exon 1 (5'-CTCTTCGGGGAGCAGCGATGC-3') and a reverse primer from exon 9 (5'-CCACACAGCAAAGCA-GAAAC-3') of EGFR gene were used in the reaction (IDT Integrated DNA Technologies", Coralville, Iowa). Approximately, 30 ng of cDNA and 130 ng of primers were used in the PCR reaction. Reaction profiles consisted of a 5-minute sample denaturation at 94° C., followed by 35 cycles of 30-second denaturation at 94° C., 30-second annealing at 59° C., and 50-second extension at 72° C. followed by a final 7 minutes synthesis step at 72° C. Products of the reaction were then electrophoresed in 1% agarose gel and stained with ethidium bromide. The resulting gel bands were excised, purified using "Wizard SV Gel and PCR Clean-Up System from Promega Corporation (Madison, Wis.) and were subject to Sanger sequencing using the same forward and reverse primers that yielded the hand to validate the EGFRvIII status.

Genomic DNA Extraction and Long Range PCR Amplification

Genomic DNA (gDNA) was extracted from frozen tumor tissue using "illustra triplePrep Kit" (GE Healthcare BioSciences Corp). For long range PCR amplification, two sets of forward primers: set A containing 13 primers and set B containing 12 primers were designed to be 5 kb apart from each other and spanning the length of intron 1 of EGFR gene, as depicted in FIG. 3A. Table 1 lists all the primers used and their location in the genome. Exon 1 forward primer, 5'-CTCTTCGGGGAGCAGCGATGC-3', is included in both set A and set B. Sequence numbering is based upon GenBank Accession #AC006977 (SEQ ID NO 26). The reverse primer was placed in exon 8. PCR reactions on gDNA were carried out using "GoTaq Green Master Mix" from Promega Corporation (Madison, Wis.) supplemented with 0.5 µL of Crimson LongAmp Taq DNA polymerase (2,500 U/ml) from New England BioLabs Inc. The following PCR steps were used: 5-minute sample denaturation at 94° C.; followed by 45 cycles of 30-second denaturation at 94° C., 45-second annealing at 57° C., and 6 minute extension at 68° C.; followed by a final 10-minutes synthesis step at 68° C. Approximately 10.5-12 ng of gDNA and 0.1 µg/µL of primers were used in each reaction. The PCR products gel were purified using "Wizard SV Gel and PCR Clean-Up System" and were subject to Sanger sequencing to determine the deletion breakpoint.

TABLE 1

Exon 1 forward primer:

1. GTC GGG CTC TGG AGG AAA AGA AAG (exon-1) (9449-9472)

Set A Primers

1. GAG TCG AAT TCC CAA CTG AGG GAG (12373-12396)
2. GTG GAG GCT AAA TGG GCC TTA AGG (22461-22484)
3. CTG ATT GAA CCT TCC CAG AGC TGG (32458-32481)
4. GTA TCT GCC CAG AAA GCT CTA CCG (39336-39359)
5. CTG CCT TGC ATG AGA CAC ACA TTC (42376-42399)
6. CCC CCA TGT ACC CCT TTC TTA ACC (52517-52540)
7. CTA CAT GCC CCT CCC TTT CCT TTC (72411-72434)
8. GTA TTT GAG AAG CCC AGG AGT GCC (82388-82411)
9. GAC CCC TAC TGG AAA GAT TCC CAC (92309-62332)
10. CCA GCT TAG ACA GCA GTT CTG CAG (102263-102286)
11. GCC TCA CAT CGT TAG TGT TCC CTC (112426-112449)
12. CAT CTT GGG CTA GGG GTG GAT ATG (122310-122333)

TABLE 1-continued

Set B Primers

1. CCT TAA GGA CAG GCA AAG GTG TCC (18526-18549)
2. CTG ACC CCT AAG GAG CCT GTA ATC (27420-27443)
3. CCC TGC TCA GAA TGT AGG CCT TAC (38416-38439)
4. GAA GAT TGC TTG TGT CTG CGT GTC (58623-58646)
5. GTG TTC CTG TCC TGG GGT ATT TGG (68243-68266)
6. CCC ATG AAA GAG TGC ACA GTC CAG (78406-78429)
7. CCT CTC ATA CAG ACC CCA GAG TTG (88182-88205)
8. TGT TCG GAA CTG TCC ATG TTC ACG (98393-98416)
9. TGA TGC TGG GAA GAC TGG AGT TAG (108003-108026)
10. TAC GAC GTG TGT TCT GTG ACT CAC (118642-118665)
11. GAA GTC CTA AGT CAT AGG GCC TGC (128343-128366)

Exon 8 reverse primer

5'-CTT CCT CCA TCT CAT AGC TGT CGG-3' (145985-146008)

Circulating DNA Extraction and PCR Amplification Through the EGFRvIII Deletion

Circulating DNA was extracted from plasma (including exosomes) using NucleoSpin Plasma XS kit from Macherey-Nagel GmbH&Co. Bethlehem, Pa. About 0.4 to 0.5 its of DNA was constantly obtained from 1 mL of plasma and 24 ng of circulating DNA was sufficient to detect the deletion by PCR. For deletion detection, primers flanking the breakpoints were designed to yield a fragment of about 300 bp. Thus, the primers to be used in plasma are designed within about 150 base pairs from each side of the breakpoint. The following primers were used to amplify through the breakpoint for patient 1: forward: 5'-CAT GAT GTT TAA TTA TTA GAG GAC TC-3' and reverse: 5'-AAG CAA GGC AAA CAC ATC-3' and for patient 7: forward: 5'-TCT AGG CCG CAA TGT GGA CAA TAC-3' and reverse: 5'-ACA GTG GCT CAT GCC TGT AAT CTC-3'. These primers were used to detect the deletion in the genomic DNA extracted from both the tumor and the plasma.

Whole Genome Sequencing

Randomly fragmented gDNA (~500 bp) was size-selected for the construction of the paired end tagged (PET) libraries (Quail, M. A., Swerdlow, H. & Turner, D. J. Improved protocols for the illumina genome analyzer sequencing system. *Curr Protoc Hum Genet* 2009; Chapter 18, Unit 18 12). The libraries were paired-end sequenced using an Illumina HiSeq platform with a readout length of 100 bp (Axeq Technologies, Macrogen Inc. Rockville, Md.). About 34-37 gigabases (Gb) of sequence were mapped to the human reference sequence (RefSeq), with an average mapping coverage of 22-25 fold. The raw sequence data were aligned to a human RefSeq (hg19) using the Bowtie 2 Aligner (Langmead, B., Trapnell, C., Pop, M., & Salzberg, S. L. Ultrafast and memory-efficient alignment of short DNA sequences to the human genome. *Genome biology* 2009; 10: R25). Four different types of tumor-specific genomic structural variations (SVs), i.e. deletion (DEL), inversion (INV), intra- and interchromosomal translocation (ITX and CTX), were detected using Control-FREEC software (Boeva, V., Popova, T., Bleakley, K., et al. Control-FREEC: a tool for assessing copy number and allelic content using next-generation sequencing data. *Bioinformatics* (Oxford, England), 2012; 28:423-5) and confirmed using the integrative genomics viewer (IGV) (Robinson, J. T. et al. Integrative genomics viewer. *Nat Biotechnol* 2011; 29, 24-26). Further Sanger sequencing was used to validate two of these SVs for each tumor. The data analysis pipeline used in this study is represented in FIG. 1.

Example 2

Detection of GBM Patients Carrying the EGFRvIII Deletion

Figure 2C:
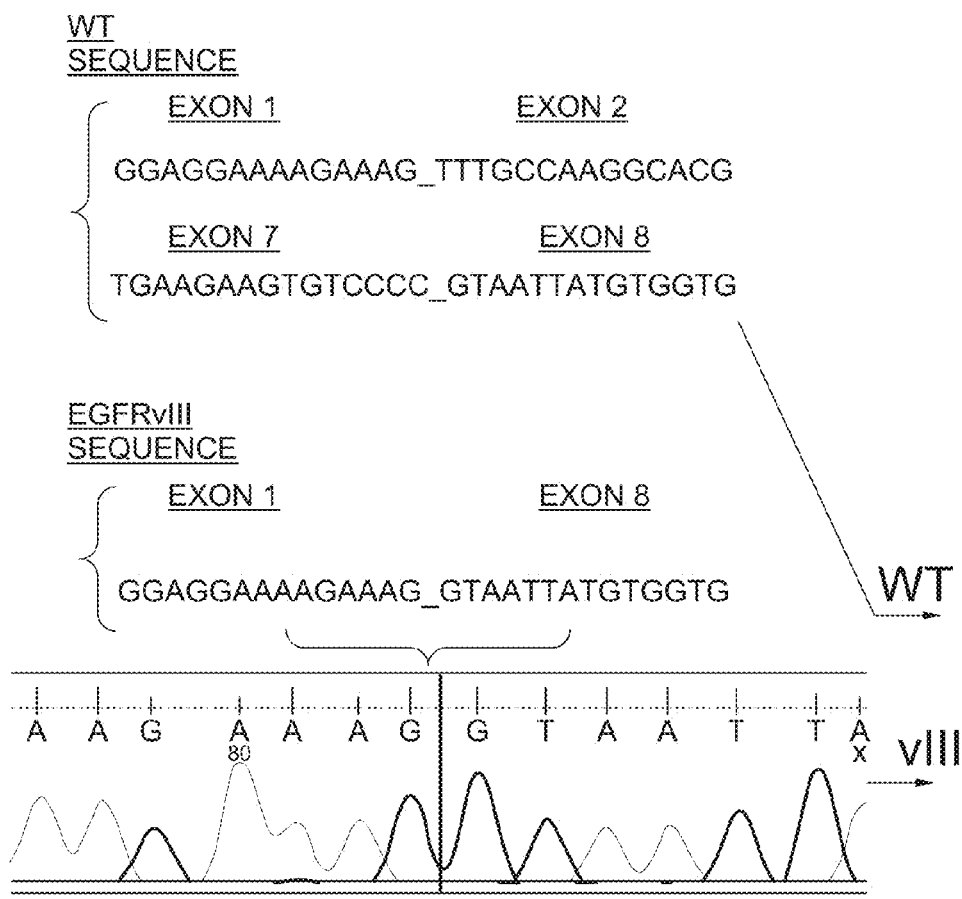
FIG. 2C depicts sequencing result of wild type and mutant genes showing the fusion of exon 1 to exon 8 in the EGFRvIII cDNA.
Figure 2D:
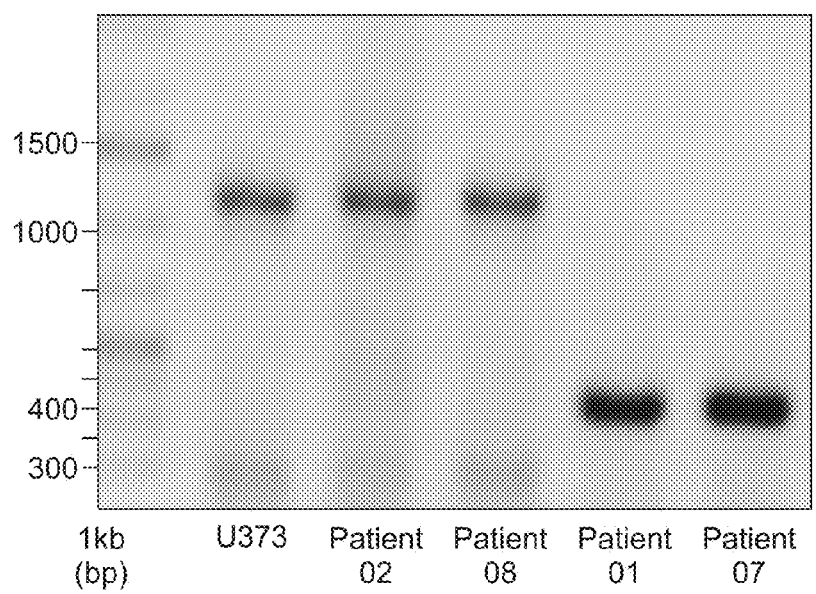
FIG. 2D. depicts detection of EGFRvIII patients using RT-PCR.

The EGFRvIII variant is the result of a deletion of exons 2 to 7 and results in a fusion of exon 1 and exon 8 (FIG. 2A). This deletion leads to the loss of 267 amino acids from the extracellular domain of the EGFR (FIG. 2B) and renders the mutant protein unable to bind to its ligand. To detect GBM patients that carry the EGFRvIII deletion, RNA was isolated from the tumors of 11 patients and was subject to a reverse transcription PCR (RT-PCR) to generate cDNA. Using a sense primer in exon 1 and an antisense primer in exon 9, PCR amplification shows that two patients (18%) carry the EGFRvIII deletion. The wild type (WT) EGFR resulted in a band of approximately 1150 bp; while the mutant variant resulted in a band of about 320 bp due to the presumed fusion of exon 1 and exon 8 (FIG. 2D). Sanger sequencing confirmed the fusion of exon 2 and exon 8 in patients 1 and 7, while the other patients are wild type, similar to the EGFR gene in the U373 GBM cell line control (FIG. 2C). Although EGFRvIII tumors are usually heterogeneous and contain EGFR wild type as well (as in tissue from patient 282 control), we only obtained the PCR band corresponding to the mutant EGFRvIII in the tumors (FIG. 2D).

Example 3

Figure 3D:
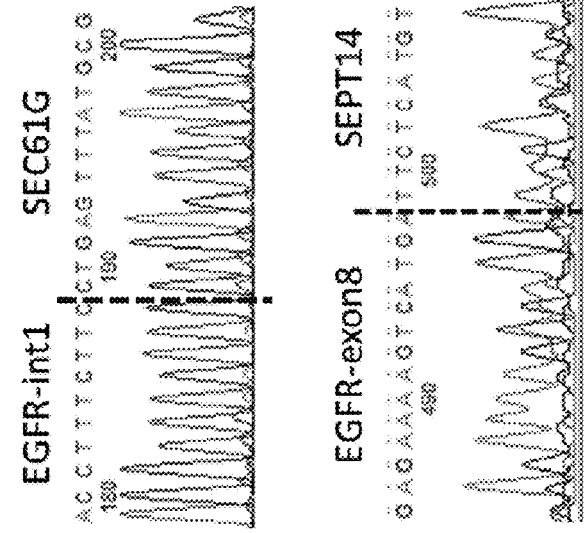
FIG. 3D shows Sanger sequencing demonstrating that EGFRvIII deletion can also involve intergenic recombinations.
Figure 3C:
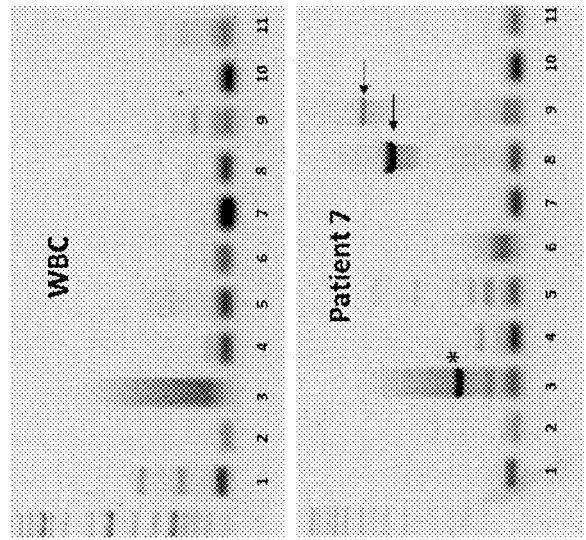
FIG. 3B and FIG. 3C depict the result of long range PCR amplifications showing specific bands in patients 1 and 7, respectively, but not in WBCs. The desired bands produced using Set B of primers are shown. Asterisk indicates a nonspecific band.
Figure 3B:
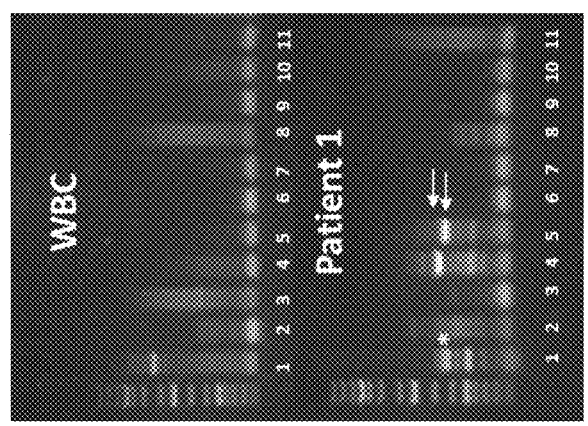

Detection of EGFRvIII Deletions in the Genomic DNA and Determination of the Breakpoints The use of genomic DNA to detect the EGFRvIII deletion is complex due to the presence of 11 Alu sites (27) in intron I (123 Kb) and one Alu site in intron 7 of EGFR gene (Reiter, J. L. et al (2001); "Comparative Genomic Sequence Analysis and Isolation of Human and Mouse Alternative EGFR Transcripts Encoding Truncated Receptor Isoforms". Genomics; 2001; 71: 1-20). These Alu sites are involved in DNA recombination events that generate genomic deletions of varying sizes leading to different EGFRvIII deletions in GBM patients. While these deletions are different at the genomic level, the mRNA is spliced the same way leading to the same truncated protein in all patients. We therefore developed a long range PCR-based strategy that uses forward primers that span the whole intron 1 and a reverse primer in exon 8 (FIG. 3A). These primers that are designed to be five kilo bases apart from each other allowed for amplification of several PCR products in the patient's genomic DNA but not in the constitutional DNA from white blood cells (WBC), indicating potential EGFRvIII deletions (FIGS. 3B and 3C). These PCR products were Sanger sequenced and their EGFRvIII status confirmed. We obtained two confirmed populations of EGFRvIII deletions for patients 1 (FIG. 3B) and 7 (FIG. 3C), and one population in patient 9 (data not shown). Surprisingly, in patient 7, one of the deletions didn't involve a direct recombination between intron 1 and intron 7 in EGFR but it involved adjacent sequences to the EGFR gene, namely the area containing SEPT14 and SEC61G genes (FIG. 3D). Patients 1 and 9, however, showed an intragenic recombination between intron 1 and intron 7 (data not shown). These recombinations and the resulting EGFRvIII deletions were confirmed using next generation sequencing of patient 7's normal and tumor DNA.

Example 4

Figure 4A:
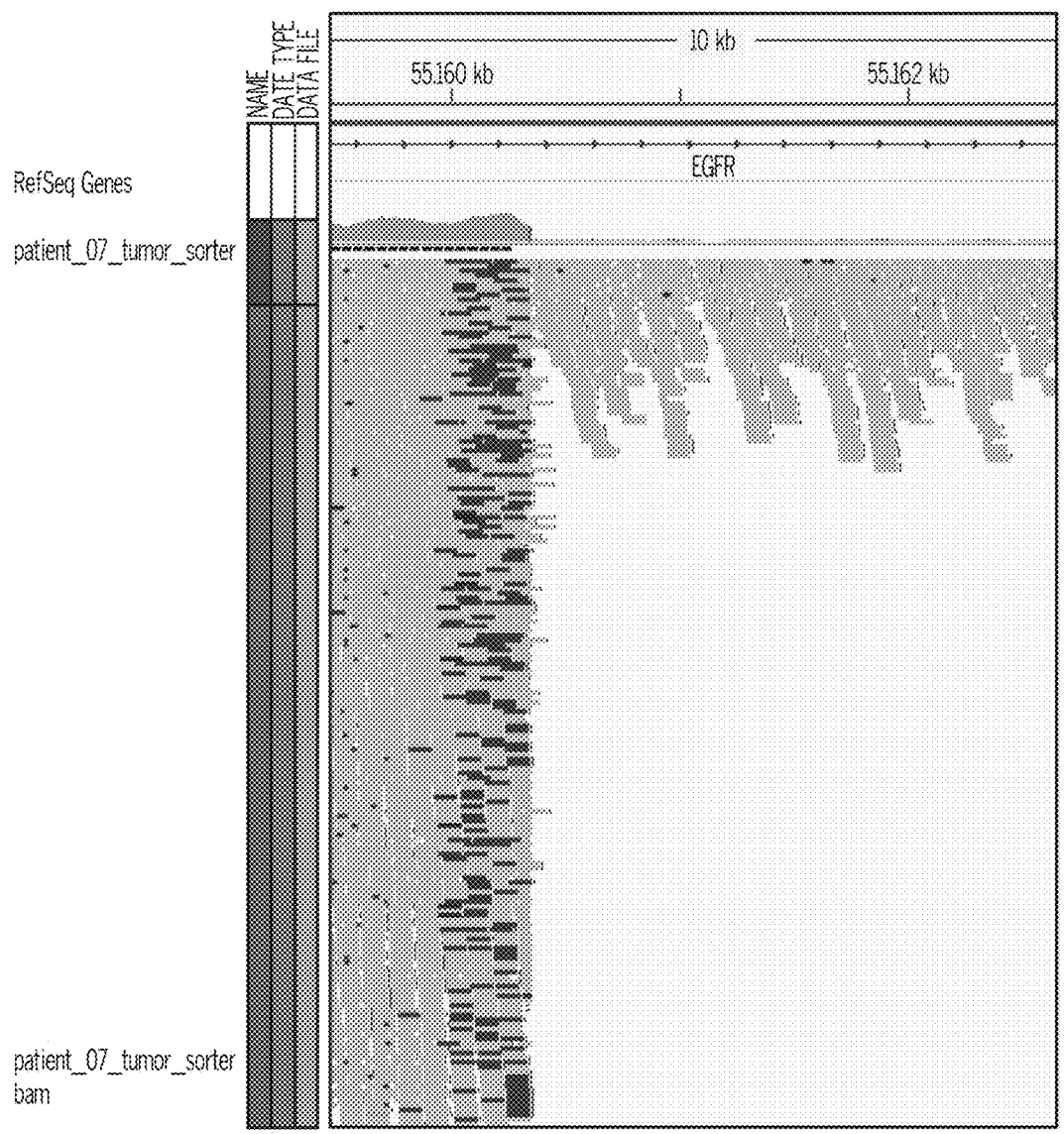
FIG. 4A & FIG. 4B depict two EGFRvIII deletions, starting at two different locations in intron 1, that were detected in patient 7.
Figure 4B:
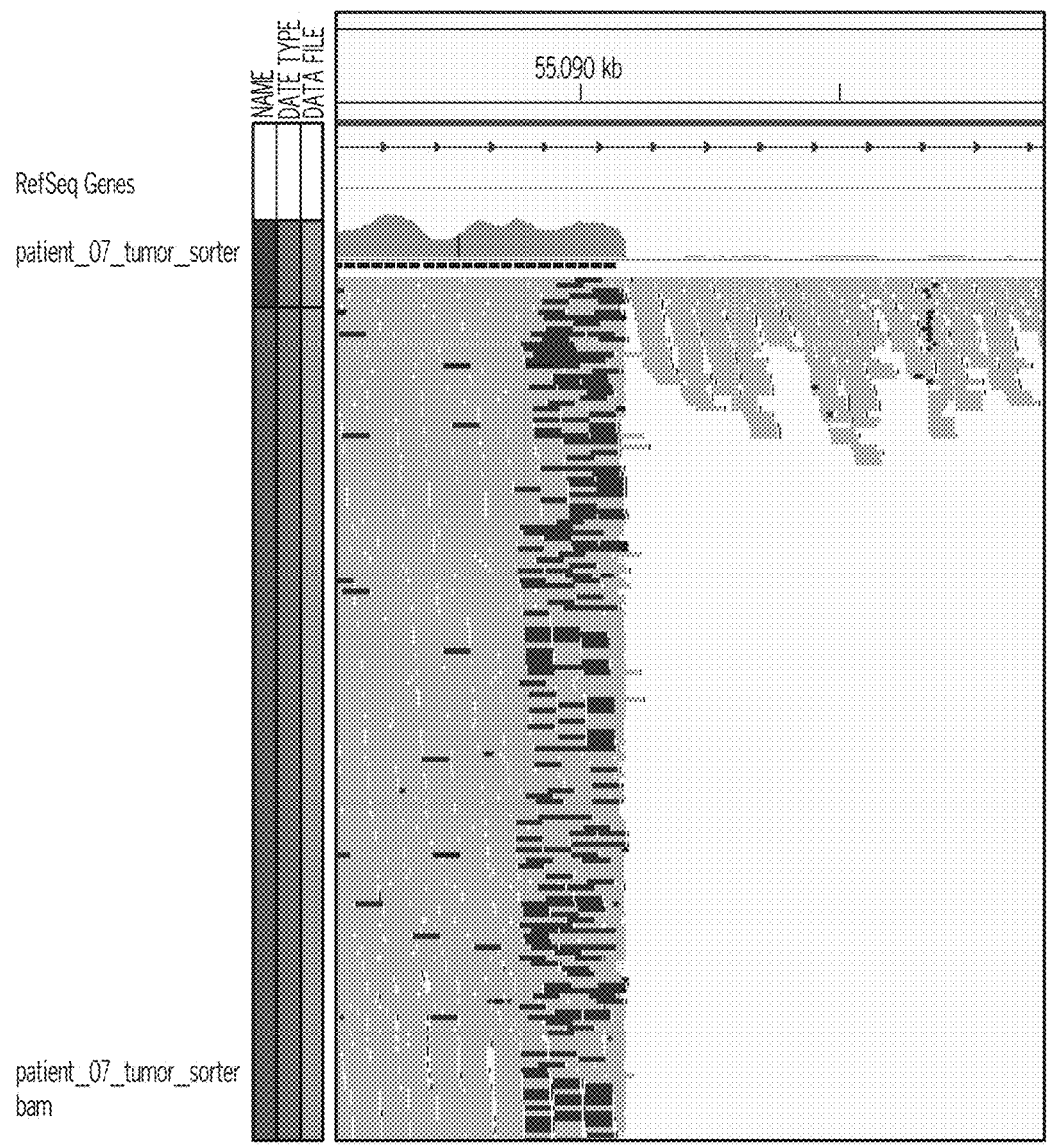
Figure 4C:
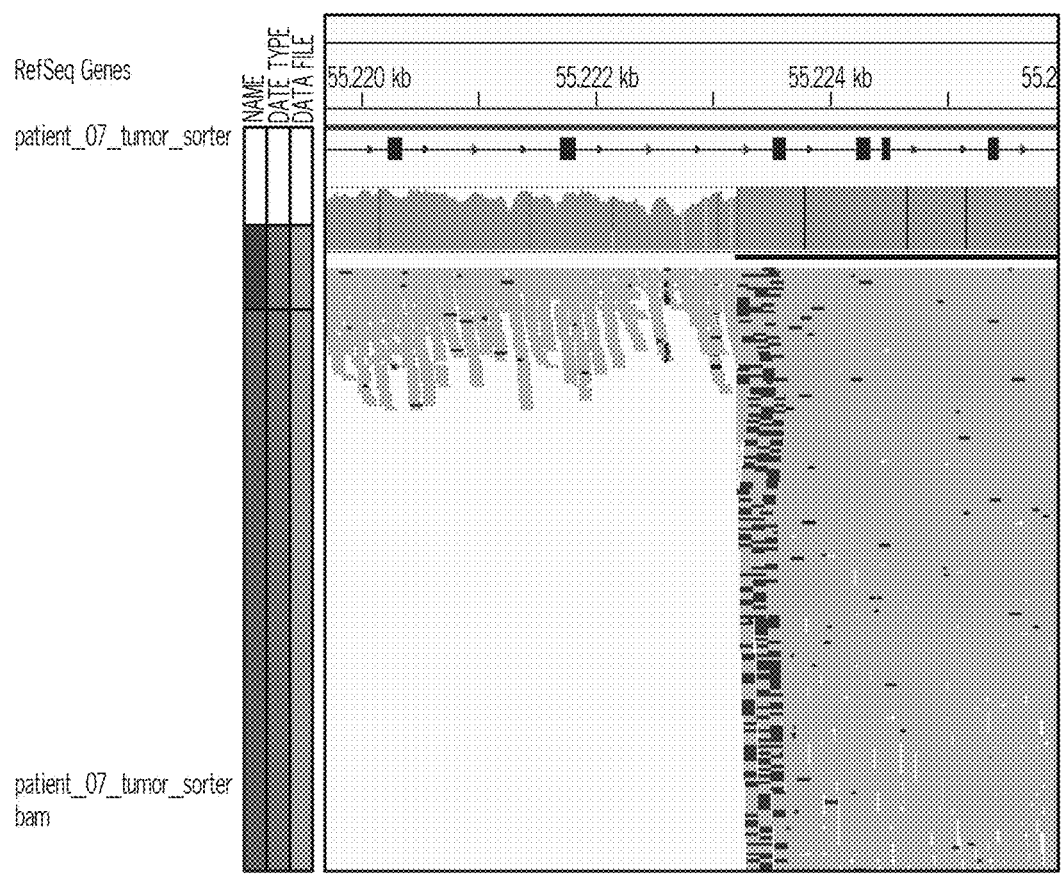
FIG. 4C depicts that both deletions in patient 7 end at one site in intron 7.
Figure 4D:
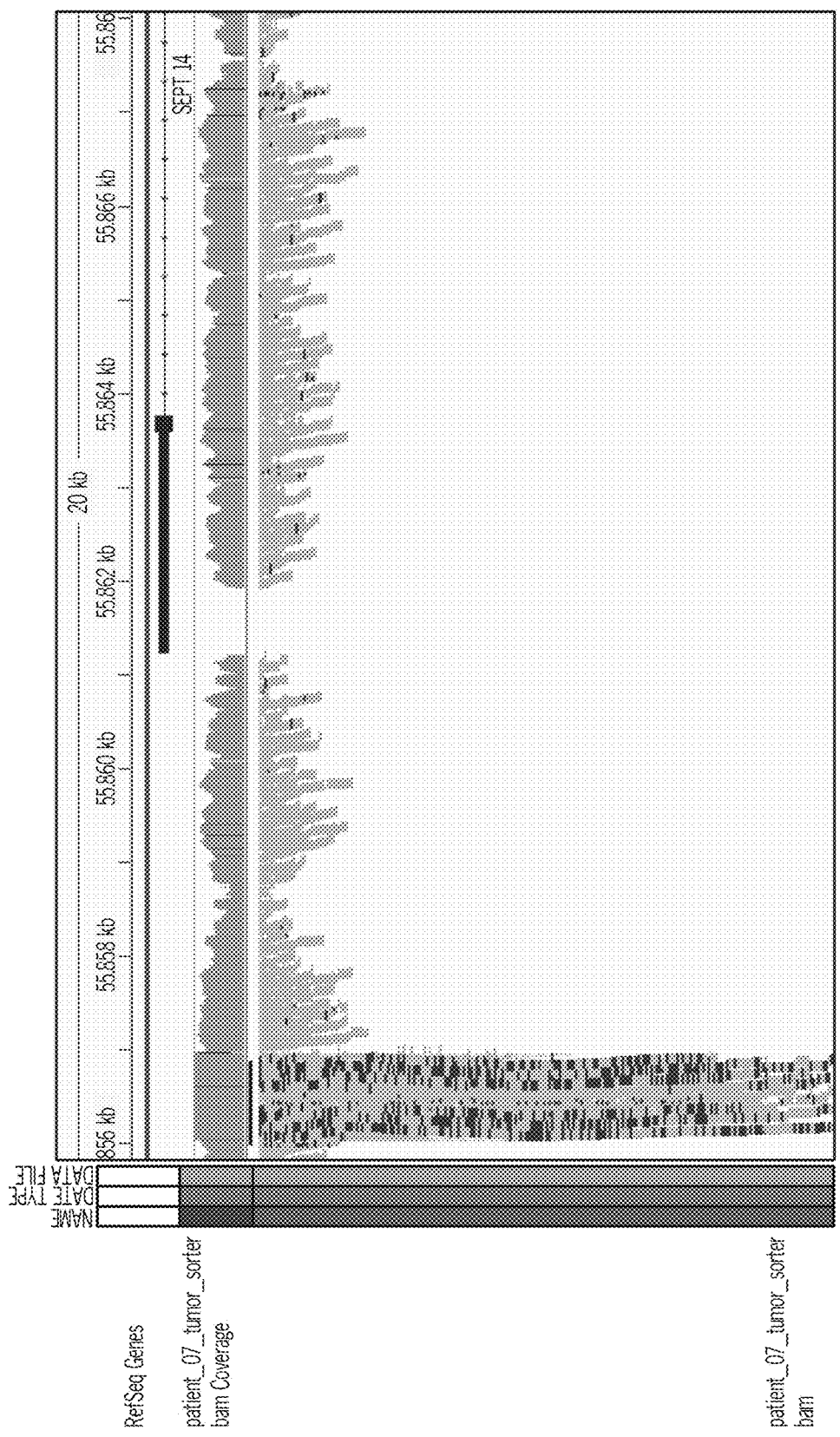
FIG. 4D and FIG. 4E depict that one of the deletions in patient 7 involved an intragenic recombination with SEPT14 and Sec61G genes, two genes adjacent to EGFR.
Figure 4E:
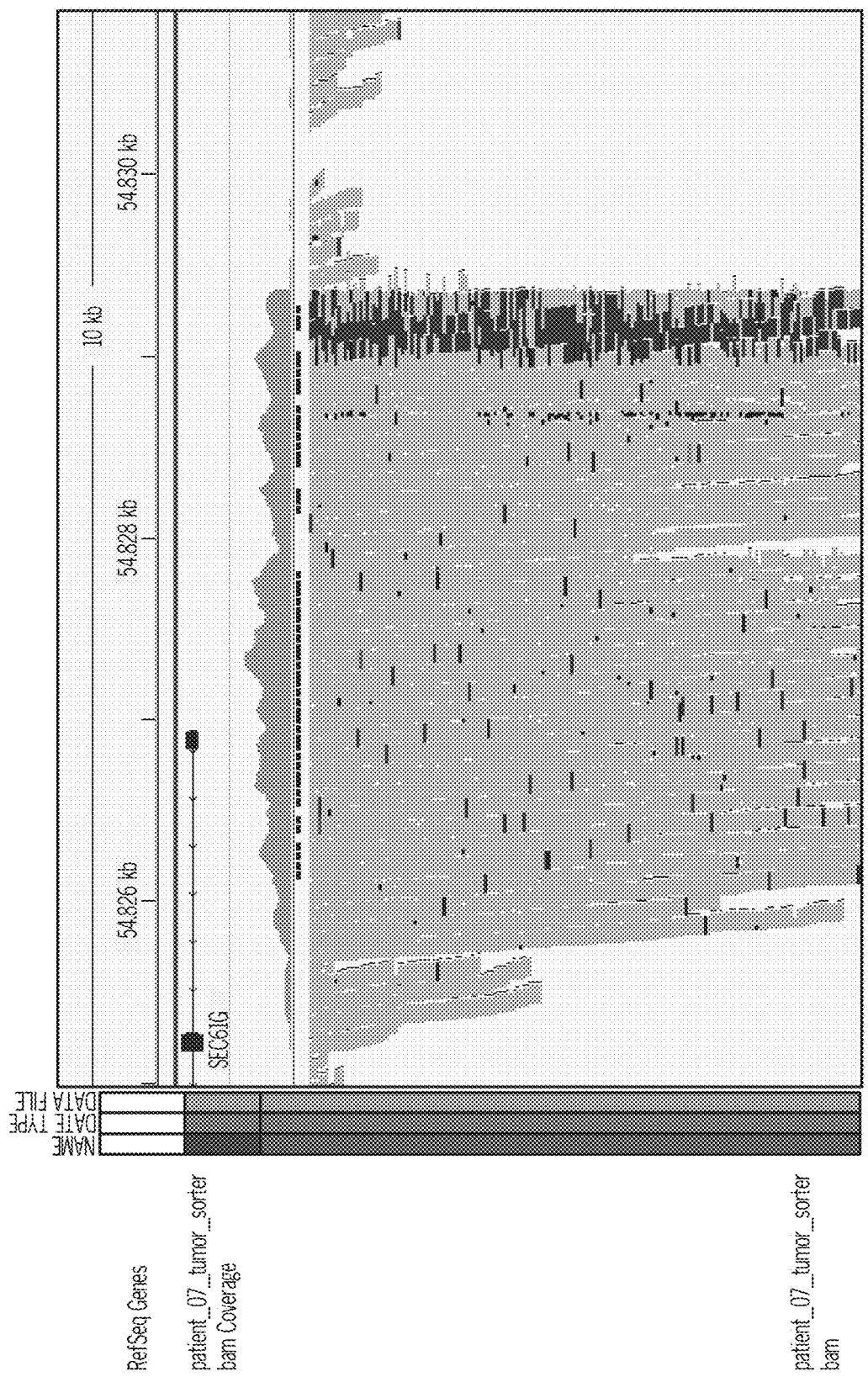

Confirmation of the EGFRvIII Deletions Using Next Generation Pair-End Sequencing To confirm the identity of EGFRvIII deletions detected by our long range PCR amplification technique, and to check whether other deletions were missed using our strategy, genomic DNA from patient 7 and the corresponding normal DNA from WBC were subjected to whole genome sequencing using the Illumina GAII platform. Four different types of tumor-specific genomic structural variations (SVs), i.e. deletion (DEL), inversion (INV), intra- and interchromosomal translocation (ITX and CTX), were detected using Control-FREEC software (Boeva, V., Popova, T., Bleakley, K., et al. Control-FREEC: a tool for assessing copy number and allelic content using next-generation sequencing data. *Bioinformatics* (Oxford, England), 2012; 28:423-5) and confirmed using the integrative genomics viewer (IGV) (Robinson, J. T. et al. Integrative genomics viewer. *Nat Biotechnol* 2011; 29, 24-26). As was seen with the long range PCR amplification, two separate deletions in intron I were detected and confirmed using IGV (FIG. 3). FIGS. 4A and 4B show the start of the deletions in intron 1, while FIG. 4C shows the end of the deletions in intron 7. Not only were we able to detect the start and end of each deletion, but we were also able to confirm the involvement of the region around SEPT14 gene and SEC61G in the recombination as indicated by the rearrangement of these two domains in this patient (FIGS. 4D and 4E). These findings confirm that our long range PCR strategy is efficient in detecting EGFRvIII deletions with very high confidence and can be used to detect the deletion in the genomic DNA without the need to sequence the whole genome, which can be costly and time consuming.

Example 5

Tracking of the EGFRvIII Deletion in the Peripheral Blood

Figure 5A:
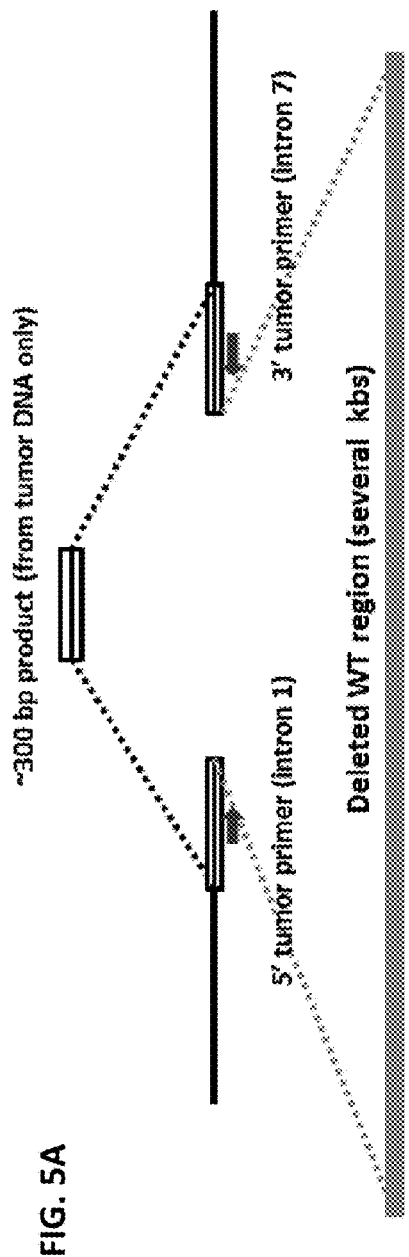
FIG. 5A depicts the detection strategy of the EGFRvIII deletion by PCR.
Figure 5C:
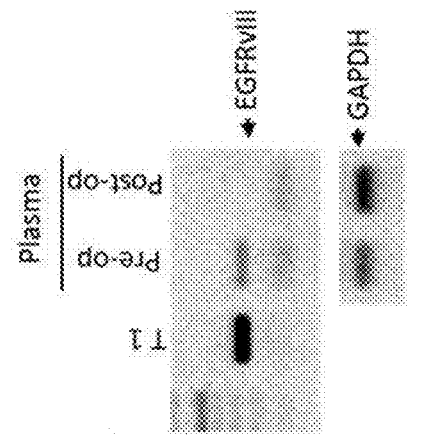
FIG. 5C depicts detection of the EGFRvIII deletion in the plasma of patient 7 before and after surgery.
Figure 5D:
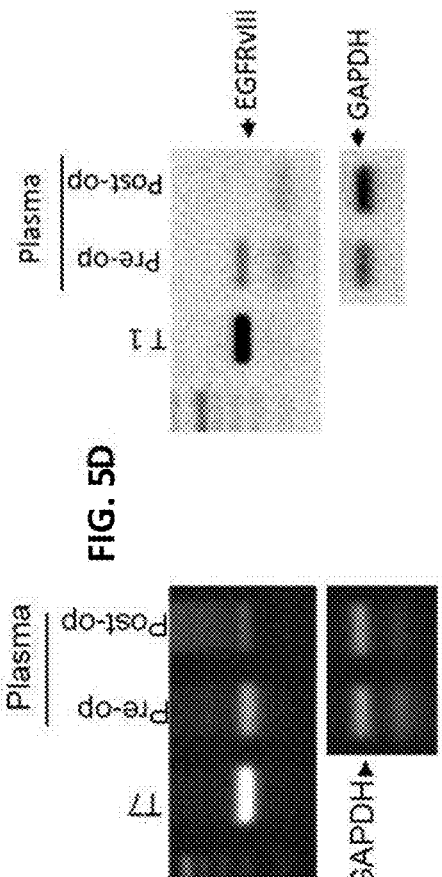
FIG. 5D depicts detection of the EGFRvIII deletion in the plasma of patient 1 before and after surgery. The quality of the circulating tumor DNA is variable between patients due to a difference in time between the blood draw and DNA extraction.
Figure 5B:
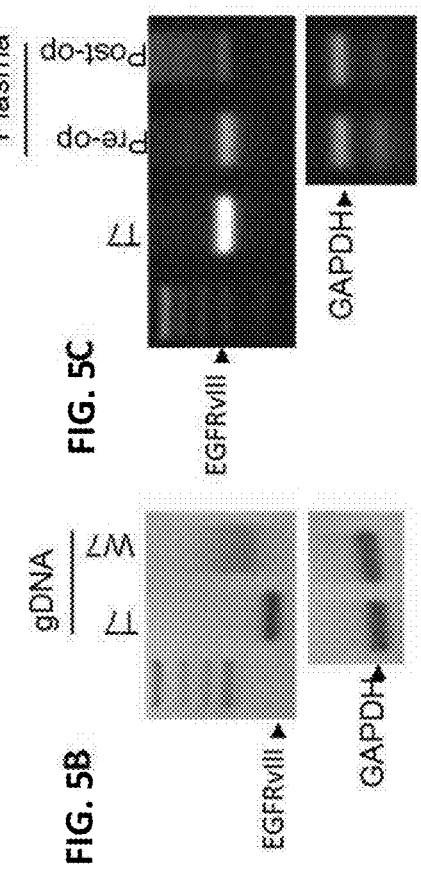
FIG. 5B depict PCR amplification of the deletion from genomic DNA using primers adjacent to the breakpoint.

To track the EGFRvIII deletion in the peripheral blood of the patients that carry this mutation and evaluate whether the mutation can be used to monitor the status of the tumor, blood was collected from the patients shortly before surgery and at three weeks after surgery. Primers were designed around the deletions to generate a PCR fragment of about 300 bp when the deletion is present. In the wild type EGFR, the fragment is too large to be detected by conventional and therefore, no PCR product is expected (FIG. 5A). As predicted, PCR amplification from genomic tumor DNA (gDNA) produced the expected size band while the wild type DNA from WBCs didn't (FIG. 5B). GAPDH was used as control. To check whether the amount of detected mutant DNA in the plasma can reflect the status of the tumor, we amplified the mutant DNA from the plasma of patient 7 (FIG. 5C) and patient 1 (FIG. 5D). Patient 7 had an incomplete resection of the tumor while patient 1 had a complete resection. Very consistent with the tumor status in these two patients, patient 1 plasma had no circulating tumor DNA (FIG. 5D), while patient 7 showed a residual amount of tumor DNA reflecting the incomplete resection of the tumor in this patient (FIG. 5C). These data show that this strategy is promising in detecting EGFRvIII in genomic DNA and in tracking these deletions in the peripheral blood.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed:

1. A method for monitoring the therapy of a patient suffering from glioblastoma multiforme (GBM), comprising:

(a) subjecting a tumor sample from the patient comprising genomic DNA to long range polymerase chain reaction amplification of epithelial growth factor receptor vIII (EGFRvIII) gene, wherein the long range polymerase chain reaction amplification utilizes a plurality of primers, the primers comprising:
   a plurality of forward primers corresponding to a DNA sequence in intron 1 of an epithelial growth factor receptor (EGFR) gene and comprising a combination of primers of Set A and Set B in Table 1, a forward primer that corresponds to a DNA sequence in exon 1 of an EGFR gene and comprises the nucleotide sequence (5'-GTCGGGCTCTCGAGGAAAAGAAAG-3') (SEQ ID NO: 1), and a reverse primer that corresponds to a DNA sequence in exon 8 of an EGFR gene and comprises nucleotide sequence (5'-CTTCCTCCATCT-CATAGCTGTCGG-3') (SEQ ID NO: 2), such that if the sample comprises genomic DNA comprising EGFRvIII, a PCR product is formed, and if the sample does not comprise genomic DNA comprising EGFRvIII, a PCR product is not formed, wherein the plurality of forward primers corresponding to a DNA sequence in intron 1 of an epithelial growth factor receptor (EGFR) gene are comprised within the base pairs defining intron 1 of the EGFR, each primer being separated by at least 5 kb from each other, and wherein the presence of PCR product is indicative of a presence of EGFRvIII in the sample, and the absence of PCR product is indicative of an absence of EGFRvIII in the sample;

(b) identifying deletion breakpoints in the PCR product and designing amplification primers that hybridize to priming sites that flank the breakpoints, wherein the amplification primers are designed to yield a PCR fragment of about 300 base pairs;

(c) amplifying DNA from body fluid samples of said patient using the designed amplification primers from step (b) to form an amplified DNA fragment of EGFRvIII; and (d) determining the amount or proportion of the amplified DNA fragment of EGFRvIII from step (c) in the body fluid samples of said patient.

2. The method of claim 1, wherein the sample DNA is circulating DNA.

3. The method of claim 1, wherein the sample DNA is plasma DNA.

4. The method of claim 1, wherein the sample DNA is serum DNA.

5. The method of claim 1, wherein amplifying according to step (c) comprises amplifying bodily fluid samples obtained from the patient at a plurality of times.

6. The method of claim 5, wherein the plurality of times are during anti-tumor therapy.

7. The method of claim 5, wherein the plurality of times are before and after surgery.

8. The method of claim 5, wherein the monitored therapy of the patient suffering from GBM comprises anti-EGFRvIII therapy.

9. The method of claim 5, wherein the patient suffering from GBM comprises a patient in remission or suffering from relapse of GBM.

10. The method of claim 1, wherein the presence of an amount of amplified DNA fragment in step (c) indicates residual GBM.

* * * * *